US007731953B2

(12) United States Patent
Leonard et al.

(10) Patent No.: US 7,731,953 B2
(45) Date of Patent: Jun. 8, 2010

(54) METHODS FOR USE OF TSLP AND AGONISTS AND ANTAGONISTS THEREOF

(75) Inventors: Warren J. Leonard, Bethesda, MD (US); Akhilesh Pandey, Pikesville, MD (US); Amin Al-Shami, Bethesda, MD (US); Rosanne Spolski, Ellicott City, MD (US)

(73) Assignees: The United States of America as represented by the Department of Health and Human Services, Washington, DC (US); Whitehead Institute of Biomedical Research, Cambridge, MA (US)

( * ) Notice: Subject to any disclaimer, the term of this patent is extended or adjusted under 35 U.S.C. 154(b) by 0 days.

(21) Appl. No.: 11/762,357

(22) Filed: Jun. 13, 2007

(65) Prior Publication Data

US 2007/0237787 A1 Oct. 11, 2007

Related U.S. Application Data

(63) Continuation of application No. 11/084,408, filed on Mar. 18, 2005, now abandoned.

(60) Provisional application No. 60/555,898, filed on Mar. 23, 2004.

(51) Int. Cl.
*A01N 63/00* (2006.01)
*C12N 5/071* (2010.01)
(52) U.S. Cl. .................................. 424/93.71; 435/372.3
(58) Field of Classification Search ....................... None
See application file for complete search history.

(56) References Cited

U.S. PATENT DOCUMENTS

| 6,555,520 B2 | 4/2003 | Sims et al. |
| 2003/0186875 A1 | 10/2003 | De Waal Malefyt et al. |
| 2007/0020262 A1 | 1/2007 | De Waal Malefyt et al. |

FOREIGN PATENT DOCUMENTS

| WO | WO 00/29581 | 5/2000 |
| WO | WO 02/068646 | 9/2002 |
| WO | WO 03/032898 | 4/2003 |
| WO | WO 03/065985 A2 | 8/2003 |

OTHER PUBLICATIONS

Burgers, 2004, Best practice and Res. Clin. Obst. and Gyn. vol. 19: 277-291.*
Ziegler et al., 2006, Nat. Immunol. vol. 7: 709-714.*
Leonard et al., Nat. Immunol. vol. 3: 605-607.*
Goldrath, 2002, Microbes and Infection. vol. 4: 539-545.*
Al-Shami et al., "A role for thymic stromal lymphopoietin in CD4(+) T cell development," *J. Exp Med.* 200(2), 159-168 (2004).
Busse et al., *Am. J. Respir. Crit. Care Med.*, 164, S12-S17 (2001).
Gilliet et al., "Human dendritic cells activated by TSLP and CD40L induce proallergic cytotoxic T cells," *J. Exp. Med.* 197(8), 1059-1063 (2003).
Isaksen et al., "Uncoupling of proliferation and Stat5 activation in thymic stromal lymphopoietin-mediated signal transduction," *J. Immunol.*, 168(7), 3288-3294 (2002).
Osborn et al., "Overexpression of murine TSLP impairs lymphopoiesis and myelopoiesis," *Blood*, 103(3), 843-851, 2004.
Park, et al., "Cloning of the murine thymic stromal lymphopoietin (TSLP) receptor: Formation of a functional heteromeric complex requires interleukin 7 receptor," *J. Exp. Med.*, 192(5), 659-669 (2000).
Quentimeier et al., "Cloning of human thymic stromal lymphopoietin (TSLP) and signaling mechanisms leading to proliferation," *Leukemia*, 15(8), 1286-1292 (2001).
Reche et al., "Human thymic stromal lymphopoietin preferentially stimulates myeloid cells," *J. Immunol.*, 167, 336-343 (2001).
Roberts et al., Eur. Respir., 14, 275-282 (1999).
Rolland et al., *Expert Opinion on Investigational Drugs*, 9, 515-527 (2000).
Sims et al., "Molecular cloning and biological characterization of a novel murine lymphoid growth factor," *J. Exp. Med.*, 192(5), 671-680 (2000).
Soumelis et al., "Human epithelial cells trigger dendritic cell-mediated allergic inflammation by producing TSLP," *Nat. Immunol.*, 3(7), 673-680 (2002).
Watanabe et al., "Human thymic stromal lymphopoietin promotes dendritic cell-mediated CD4+T cell homeostatic expansion," *Nature Immunol.*, 5(4), 426-434 (2004).
Rochman et al., "Cutting Edge: Direct Action of Thymic Stromal Lymphopoietin on Activated Human CD4+T Cells," *J. Immunol.*, 178, 6720-6724 (2007).
Soumelis et al., "Human thymic stromal lymphopoietin: a novel epithelial cell-derived cytokine and a potential key player in the induction of allergic inflammation," *Springer Seminars in Immunopathology*, 25, 325-333 (2004).

* cited by examiner

*Primary Examiner*—Amy E Juedes
(74) *Attorney, Agent, or Firm*—Leydig, Voit & Mayer

(57) ABSTRACT

Methods are disclosed herein for specifically inducing proliferation of CD4+ T cells. The methods are of use in treating immunodeficiencies, such as an immunodeficiency produced by infection with an immunodeficiency virus, such as infection with a human immunodeficiency virus (HIV). The methods include contacting isolated mammalian CD4+ T cells with an effective amount of a thymic stromal derived lymphopoietin (TSLP) polypeptide or a therapeutically effective amount of nucleic acid encoding the TSLP polypeptide, thereby inducing proliferation of the T cells. Methods are also disclosed for treating an IgE mediated disorder, such as asthma. The methods include administering to a subject a therapeutically effective amount of a TSLP antagonist. Transgenic mice are also disclosed herein. The somatic and germ cells of these mice include a disrupted thymic stromal lymphopoietin receptor (TSLP) gene, the disruption being sufficient to inhibit the interaction of TSLP with its receptor, and a disrupted $\gamma_c$ gene, the disruption being sufficient to reduce signaling through the $\gamma_c$. The mice exhibit diminished thymic cellularity. Methods of using these mice for drug screening are also disclosed.

9 Claims, 17 Drawing Sheets

Table 3: Absence of TSLPR blocks the development of lung inflammation and infiltration of inflammatory cells.

| | Analysis | Score | Monocytes | Lymphocytes | Neutrophils | Eosinophils |
|---|---|---|---|---|---|---|
| WT+PBS | Normal lungs | 0-1 | 87±4 % | 13±4% | 0 % | 0 % |
| KO+PBS | Normal lungs | 0-1 | 95±3 % | 5±3 % | 0 % | 0 % |
| WT+OVA | High perivascular and peribronchial inflammation | 3-3.5 | 42±2 % | 21±3 % | 16±4% | 21±4 % |
| KO+OVA | Slight inflammation | 0.5-1.5 | 87±2 % | 11±2 % | 1±1 % | 1±1 % |

Balb/c WT and TSLPR KO mice were sensitized (i.p.) and challenged (i.t. and i.n.) with OVA or PBS (i.p.). Levels of inflammation in the lungs observed in Figure 4 by PAS staining as well as the distribution of infiltrating leukocytes in BAL. TSLPR KO mice challenged with OVA showed weak inflammation with little infiltration of inflammatory cells as compared to WT animals.

FIG. 17

METHODS FOR USE OF TSLP AND AGONISTS AND ANTAGONISTS THEREOF

CROSS-REFERENCE TO RELATED APPLICATIONS

This application is a continuation of U.S. patent application Ser. No. 11/084,408, filed Mar. 18, 2005, which claims the benefit of U.S. Provisional Patent Application No. 60/555,898, filed Mar. 23, 2004, which is incorporated by reference in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 10,214 Byte ASCII (Text) file named "701665ST25.TXT," created on Jun. 11, 2007.

FIELD

This disclosure relates to the field of immunology, specifically to the use of thymic stromal lymphopoietin (TSLP), or TSLP agonists, to induce T cell proliferation and to treat immunodeficiency disorders. This disclosure also relates to the use of TSLP antagonists to treat an IgE-mediated disorder, such as asthma or rhino-conjunctivitis.

BACKGROUND

In recent years, a novel murine growth factor, designated thymic stromal lymphopoietin (TSLP), has been isolated. TSLP has been demonstrated to have a role in B cell development and maturation. The cytokine activity of murine TSLP is very similar to that of IL-7, which is required during proliferation and survival of pre-B cells (Friend et al., *Exp. Hematol.*, 22:321-328, 1994). In addition, mature B lymphocytes fail to develop in the absence of either IL-7 or murine TSLP. It has further been shown that murine TSLP can replace IL-7 in sustaining B cell proliferative responses (Ray et al., *Eur. J. Immunol.* 26:10-16, 1996). Studies with IL-7 receptor (IL-7R) knockout mice indicate that IL-7, TSLP, or both, play a role in controlling the rearrangement of the T cell receptor-gamma (TCR.gamma) locus (Candeias et al., *Immunology Letters* 57: 9-14, 1997). Human TSLP has been cloned and sequenced (see U.S. Pat. No. 6,555,520). There is a need to determine the role in of TSLP human T cell development and maturation.

The primary immunologic abnormality resulting from infection by HIV is the progressive depletion and functional impairment of T lymphocytes expressing the CD4 cell surface glycoprotein (Lane et al., *Ann. Rev. Immunol.* 3:477, 1985). CD4 is a non-polymorphic glycoprotein with homology to the immunoglobulin gene superfamily (Maddon et al., *Cell* 42:93, 1985). Together with the CD8 surface antigen, CD4 defines two distinct subsets of mature peripheral T cells (Reinherz et al., *Cell* 19:821, 1980), which are distinguished by their ability to interact with nominal antigen targets in the context of Class I and Class II major histocompatibility complex (MHC) antigens, respectively (see Swain, *Proc. Natl. Acad. Sci.* 78:7101, 1981). For the most part, CD4 T cells display the helper/inducer T cell phenotype (Reinherz, supra), although CD4 T cells characterized as cytotoxic/suppressor T cells have also been identified (Thomas et al., *J. Exp. Med.* 154:459, 1981; Meuer et al., *Proc. Natl. Acad. Sci. USA* 79:4395, 1982). The loss of CD4 helper/inducer T cell function probably underlies the profound defects in cellular and humoral immunity leading to the opportunistic infections and malignancies characteristic of the acquired immunodeficiency syndrome (AIDS) (Lane et al., *Ann. Rev. Immunol.* 3:477, 1985). Studies of HIV-I infection of fractionated CD4 and CD8 T cells from normal donors and AIDS patients have revealed that depletion of CD4 T cells results from the ability of HIV-I to selectively infect, replicate in, and ultimately destroy this T lymphocyte subset (Klatzmann et al., *Science* 225:59, 1984).

The widespread use of highly active antiretroviral therapy (HAART) has dramatically improved the clinical course for many individuals infected with HIV (Berrey et al., *J Infect Dis* 183(10):1466, 2001). However, toxicities associated with long term HAART have put a high priority on the design and development of less toxic therapies. Among the "next generation" of anti-viral inhibitors is T-20 (Wild et al., *Proc Natl Acad Sci USA* 91(26):12676, 1994; Wild et al. *Proc Natl Acad Sci USA* 89(21):10537, 1992). However, there remains an acute need for additional therapeutic agents that can be used alone or in combination with HAART to increase CD4 activity and treat HIV-infected individuals.

SUMMARY

Methods are disclosed herein for specifically inducing proliferation of $CD4^+$ T cells. These methods are of use in increasing the absolute number of $CD4^+$ T cells, and in increasing the CD4/CD8 ratio. The methods are of use in treating immunodeficiencies, such as an immunodeficiency produced by infection with an immunodeficiency virus, such as infection with a human immunodeficiency virus (HIV). The methods include contacting isolated mammalian CD4+ T cells with an effective amount of a thymic stromal derived lymphopoietin (TSLP) polypeptide or a therapeutically effective amount of nucleic acid encoding the TSLP polypeptide, thereby inducing proliferation of the T cells.

Methods are also disclosed for the treatment of an inflammatory disorder such as asthma, allergic rhinitis, allergic dermatitis, and allergic conjunctivitis. In one embodiment, the inflammatory disorder is an IgE-mediated disorder, such as a pulmonary IgE mediated disorder. For example, the disorder can be asthma. The methods include administering to a subject with an IgE-mediated disorder a therapeutically effective amount of an antagonist of TSLP, thereby ameliorating a sign or a symptom of the disorder.

Transgenic mice are also disclosed herein. The somatic and germ cells of these mice include a disrupted thymic stromal lymphopoietin receptor (TSLP) gene, the disruption being sufficient to inhibit the interaction of TSLP with its receptor, and a disrupted $\gamma_c$ gene, the disruption being sufficient to reduce signaling through the $\gamma_c$. The mice exhibit diminished thymic cellularity. Methods of using these mice for drug screening are also disclosed.

The foregoing and other features and advantages will become more apparent from the following detailed description of several embodiments, which proceeds with reference to the accompanying figures.

BRIEF DESCRIPTION OF THE FIGURES

FIG. 1A is a schematic diagram of the TSLPR targeting strategy. The 6 kb BglII to Nhe I 5' and 3 kb Pvu II 3' flanking regions of the TSLPR gene were cloned 5' and 3' to the Neo gene. The targeting vector was linearized, electroporated into ES cells, and transfected clones were screened using 5' and 3' probes (filled squares). FIG. 1B is a digital image of a Southern hybridization of the ES clones. The restriction enzymes and fragment sizes are indicated (+/+ for wild-type, +/− for heterozygote). FIG. 1C is a digital image of the genotyping of the mice, which was performed as described in the Material and Methods (left panel). RT-PCR was performed using TSLPR internal primers to detect the TSLPR mRNA transcript thymus (right panel). FIG. 1D is a bar graph showing that TSLP significantly increased anti-CD3ε-induced proliferation of WT splenocytes (p<0.001) but not of TSLPR KO splenocytes. Results are expressed as mean fold induction ±SEM (n=14). FIGS. 1E, 1F and 1G are plots of flow cytometric analysis showing no difference in the CD4/CD8 profile of the total thymus (FIG. 1E, upper panel), the CD25/CD44 profile of DN thymocytes (FIG. 1E, lower panel), or in spleen (FIG. 1F) and bone marrow (BM) (FIG. 1G) of wild-type and TSLPR deficient mice. Antibodies for the $CD4^+$ and $CD8^+$ surface markers were used to evaluate the T cell populations in the thymus (FIG. 1E) and spleen (FIG. 1F, upper panel) while antibodies for $B220^+$ and surface $IgM^+$ were used to evaluate B cells populations in the spleen (FIG. 1F, lower panel) and BM (FIG. 1G).

FIG. 2A is a graph of the absolute number of thymocytes, splenocytes and BM cells in WT mice injected daily with PBS, IL-7, or TSLP for 1 and 3 weeks. One week of treatment with TSLP and IL-7 increased thymic cellularity (means ±SEM of $204±46×10^6$ and $195±22×10^6$ [p=0.01 and p=0.001, respectively] versus $139±13×10^6$ for PBS treated mice). One week of treatment with TSLP and IL-7 also increased splenic cellularity (means ±SEM of $126±23×10^6$ and $118±13×10^6$ [p=0.004 and p=0.002, respectively] versus $80±12×10^6$ for the PBS treated mice). No significant difference was observed in the BM. After 3 weeks of treatment with TSLP or IL-7, the changes in cellularity of thymus, spleen, and BM were not significant. FIG. 2B is a plot of the results from flow cytometric analysis of the BM 1 and 3 weeks after injection of WT mice with PBS, IL-7, or TSLP. FIG. 2C is a table listing the percentages of populations shown in FIG. 2B.

FIG. 3A is a graph showing that TSLPR KO treated with control or anti-IL-7 mAbs displayed lower thymic cellularity (p<0.001 for both mAbs) and splenic cellularity (p=0.03 for anti-IL-7 and p=0.02 for control mAb) when compared to WT littermates. FIG. 3B is a set of graphs of the absolute numbers of thymic subpopulations, except for DN cells, were decreased in TSLPR KO mice as compared to WT mice (p<0.05). FIG. 3C is a graph of the absolute numbers of $CD4^+$ and $CD8^+$ T cells and B cells in spleens of irradiated animals. Mice lacking TSLPR had fewer lymphocytes than WT mice, when experiments were performed with either control or anti-IL-7 mAbs (p<0.05). FIG. 3D is a set of plots showing B220 versus CD19 flow cytometric analysis of spleen and bone marrow from WT (upper panel) and TSLPR KO (lower panel) mice.

FIG. 4A is a graph showing $\gamma_c$/TSLPR double KO (DKO) mice had lower thymic, spleen and BM cellularities than did $\gamma_c$ KO mice (thymus: mean ±SEM of $12.3±6.7×10^6$ for $\gamma_c$ KO mice versus $5.7±4.5×10^6$ for $\gamma_c$/TSLPR DKO mice [p=0.009]; spleen: mean ±SEM of $43±17.7×10^6$ for $\gamma_c$ KO mice versus $26.8±13.7×10^6$ for $\gamma_c$/TSLPR DKO mice [p=0.02]; bone marrow: mean ±SEM of $23.4±15.5×10^6$ for $\gamma_c$ KO mice versus $14.3±7.6×10^6$ for $\gamma_c$/TSLPR DKO mice [p=0.047]). All mice were age-matched and no sex-related differences were noted. FIG. 4B is a plot of the results obtained from flow cytometric analysis of bone marrow (B220 versus CD43, upper panel) and peritoneal cavity lymphocytes (B220 versus CD5, lower panel). FIG. 4C is a graph showing similar levels of IgM in the serum of $\gamma_c$ KO and $\gamma_c$/TSLPR double KO mice. FIG. 4D is a graph showing injection of 0.5 μg/day of TSLP (open rectangles) enhances lymphoid cellularity in $\gamma_c$ KO mice. Treatment for 1 and 3 weeks showed an enhanced cellularity in thymus (mean ±SEM of $7.8±2.9×10^6$ for PBS-injected mice versus $32±10×10^6$ for TSLP-injected [p<0.0001] after 1 week treatment and a mean ±SEM of $3.5±2×10^6$ for PBS-injected mice versus $12.2±4×10^6$ for TSLP-injected [p=0.001] after 3 weeks) and spleen (mean ±SEM of $8±4×10^6$ for PBS-injected mice versus $14±5.4×10^6$ for TSLP-injected [p=0.003] after 1 week treatment and a mean ±SEM of $15±4×10^6$ for PBS-injected mice versus $52±12×10^6$ for TSLP-injected [p<0.0001] after 3 weeks). No change was seen in the BM. All mice were age-matched and no sex-related differences were noted. $\gamma_c$/TSLPR DKO mice did not respond to TSLP injections (filled triangles). FIG. 4E is a set of digital images showing thymic size in $\gamma_c$ KO mice after 1 week treatment with PBS or TSLP (upper panel) and a histological analysis of these tissues by H&E staining (lower panel).

FIG. 5A is a set of plots of the results from flow cytometric analysis of $\gamma_c$ KO thymus, spleen, and BM 1 and 3 weeks after injection of PBS or TSLP. FIG. 5B is a table showing B cell populations in BM from FIG. 1A, subpanels vii, viii, xv, and xvi. FIG. 5C is a graph showing that TSLP injections induced an increase in $CD4^+$ T cells (mean ±SEM of $2.36±1.48×10^6$ for control mice versus $12.7±6.7×10^6$ for TSLP treated mice [p<0.0001] for a 5.4 fold increase), $CD8^+$ T cells (mean ±SEM of $0.63±0.43×10^6$ for control mice versus $2.4±1.7×10^6$ for TSLP treated mice [p=0.01] for a 3.8 fold increase) as well as B cells (mean ±SEM of $4.6±1.2×10^6$ for control mice versus $27±7×10^6$ for TSLP treated mice [p<0.0001] for a 5.9 fold increase) in the spleen of $\gamma_c$ KO mice, 3 weeks following injection. FIG. 5D is a set of plots of the results from flow cytometric analysis of splenic $CD4^+$ T cells in $\gamma_c$ mice treated with PBS or TSLP for 3 weeks. TSLP increased the absolute numbers of $CD44^{high}$ $CD62L^{low}$ (mean ±SEM of $2.3±1.2×10^6$ for control $\gamma_c$ mice versus $11.3±4.1×10^6$ for TSLP treated mice [p=0.0004] for 4.9 fold increase), $CD44^{high}$ $CD62L^{high}$ (mean ±SEM of $0.4±0.2×10^6$ for control $\gamma_c$ mice versus $3.2±1.1×10^6$ for TSLP treated mice [p=0.0003] for an 8 fold increase) and $CD44^{low}$ $CD62L^{high}$ (mean ±SEM of $0.08±0.06×10^6$ for control $\gamma_c$ mice versus $0.9±0.16×10^6$ for TSLP treated mice [p<0.0001] for an 11 fold increase). FIG. 5E is a set of plots of the results of experiments wherein $\gamma_c$ KO mice were treated with PBS or TSLP for 1 week, injected with BrdU 10 and 16 hours before sacrifice. BrdU incorporation was measured by intracellular staining using PE-labeled BrdU of the thymocytes subpopulations. The number indicates the percent of $BrdU^+$ cells within the gated region.

FIG. 6A is a bar graph showing the in vitro proliferation of purified $CD4^+$ and $CD8^+$ SP thymocytes from WT mice. Results are expressed as mean ±SEM for 4 experiments. TSLP increased anti-CD3ε induced proliferation of CD4$^+$ SP cells (p=0.02) but did not significantly affect CD8$^+$ SP expansion to anti-CD3ε (p=0.07). IL-7 significantly enhanced anti-CD3ε induced expansion of both CD4$^+$ and CD8$^+$ SP thymocytes (p<0.0001 for both). FIG. 6B is a bar graph showing in vitro proliferation of purified CD4$^+$ and CD8$^+$ splenocytes (prepared by positive selection) treated as described above. TSLP significantly increased anti-CD3ε-induced proliferation of mature CD4$^+$ T cells (p=0.0002) but not of CD8$^+$ T cells (p=0.1). IL-7 significantly enhanced anti-CD3ε induced expansion of both CD4$^+$ and CD8$^+$ mature T cells (p=0.008 and p=0.0005 respectively). FIG. 6C is a set of plots showing the results obtained when CD4$^+$ thymocytes and splenic T cells were labeled with CFSE and cultured for 1 week with anti-CD3ε with or without TSLP, and cells were analyzed by flow cytometry. As evaluated by decreased CFSE staining, TSLP increased anti-CD3ε-induced proliferation of CD4$^+$ but not of CD8$^+$ T cells. WT corresponds to the "open" curve, whereas TSLPR KO mice are shown in solid black.

FIG. 7A is a bar graph demonstrating the in vitro survival of purified CD4$^+$ and CD8$^+$ SP thymocytes from WT mice. The percent viable cells (mean ±SEM for 4 experiments) was determined after 1 week by trypan blue exclusion. TSLP increased anti-CD3ε induced survival of CD4$^+$ cells (p=0.02) but did not significantly affect CD8$^+$ survival (p=0.24). IL-7 significantly enhanced anti-CD3ε induced survival of both CD4$^+$ and CD8$^+$ thymocytes (p=0.03 and p<0.0001, respectively). FIG. 7B is a bar graph showing the results obtained from an in vitro survival assay of purified CD4$^+$ and CD8$^+$ splenic T cells from WT mice. The percentage of viable cells was determined by trypan blue exclusion. Results are expressed as mean ±SEM for 5 experiments. TSLP significantly increased anti-CD3ε induced survival of CD4$^+$ T cells (p<0.0001) but not of CD8$^+$ T cells (p=0.21). IL-7 significantly enhanced anti-CD3ε induced survival of both CD4$^+$ and CD8$^+$ T cells (p<0.001 and p<0.0001, respectively). FIG. 7C is a set of plots showing purified CD4$^+$ and CD8$^+$ splenocytes cultured as indicated were stained with Annexin V and 7-AAD.

FIG. 8A is a graph showing that after 1 week, TSLPR KO CD4$^+$ T cells expanded less than CD4$^+$ T cells from WT mice (p=0.008). CD8$^+$ T cells from WT or TSLPR mice expanded to a similar degree. FIG. 8B is a set of plots showing that examination of the CFSE dilution on day 3 by flow cytometry revealed that WT CD4$^+$ T cells were expanding more rapidly than TSLPR KO CD4$^+$ T cells. No differences were observed for CD8$^+$ T cells.

FIG. 11A is a graph of the results of in vitro antigen recall response. CD4$^+$ T cells and APC from immunized WT and TSLPR KO mice were cultured with 200 μg/ml of OVA for 48 hours before being pulsed with $^3$H thymidine. Replacing WT-APC with TSLPR KO-derived APC reduced the antigen-driven proliferation of WT CD4$^+$ T cells. However WT-APC did not rescue the defected expansion of TSLPR KO CD4$^+$ T cells. Shown are means ±SEM for 7 experiments. For the plots shown in FIG. 11B, splenic CD11c$^+$ cells were sorted from the spleens of WT Balb/c animals and incubated overnight with 5 μg/ml of OVA$^{323-339}$ peptide alone or with TSLP. TSLP treatment increased the surface levels of CD80, MHC class II, and CD86 as compared to peptide alone. For the bar graph shown in FIG. 11C, sorted splenic DC were incubated with 5 μg/ml of OVA$^{323-339}$ peptide alone or with TSLP before being washed, treated with mitomycin C, and cultured with purified CD4$^+$ T cells from DO11.10 RAG2$^{-/-}$ mice at a 1:10 ratio. Antigen presentation of DC was significantly enhanced by TSLP treatment (means ±SEM for 5 experiments). For the results graphed in FIG. 11D, CD4$^+$ T cells and DC were purified from DO11.01/WT and DO11.10/TSLPR KO unmanipulated mice, and these were cultured together in the indicated combinations at a ratio of 1:10 DC:T cell, with 5 μg/ml of OVA$^{323-339}$ peptide. Proliferation after 48 hours was examined by measuring $^3$H-thymidine incorporation. Replacing WT-APC with TSLPR KO-derived DC moderately but significantly reduced the antigen-driven proliferation of DO11.10 Tg/WT CD4$^+$ T cells (p=0.04). WT-DC provided no significant enhancement over the weak expansion of DO11.10/TSLPR KO CD4$^+$ T cells. Shown are means ±SEM for 7 experiments. In this figure, * indicates statistical significance p<0.05.

FIG. 12D is a bar graph showing that no significant difference was observed in the levels of IL-12 (p35) mRNA examined by RTPCR in CD11c$^+$ DC that were incubated overnight with 5 µg/ml of OVA$^{323\text{-}339}$ peptide alone or with TSLP. For the plots shown in FIG. 12E, total splenocytes from DO11.10/WT and DO11.10/TSLPRKO mice were cultured for 4 days with 5 µg/ml of OVA$^{323\text{-}339}$ peptide before being activated with PI for 5 h. KJ1-26$^+$ TSLPR KO T cells produced more IFN-γ than DO11.10/WT cells. For the bar graph shown in FIG. 12F, RNA was extracted from DO11.10/WT and DO11.10/TSLPRKO total splenocytes that were cultured for 4 days with 5 µg/ml of OVA$^{323\text{-}339}$ peptide. RTPCR revealed significantly lower levels of IL-4 transcripts in the spleens of TSLPR KO mice ($p<0.05$).

FIG. 14A is a set of bar graphs showing serum levels of OVA-specific immunoglobulin in PBS and OVA treated mice. OVA-TSLPR KO displayed significantly less IgE and more IgG2a than WT treated littermates. FIG. 14B is a set of bar graphs showing cytokine levels in the lungs as determined by RT-PCR. The results are expressed as means ±SEM for 4 experiments; * indicates statistical significance $p<0.05$.

FIG. 17 is Table 3.

SEQUENCE LISTING

Figures 1, 1A, 1B, 1C, 1D, 1E, 1F, 1G:
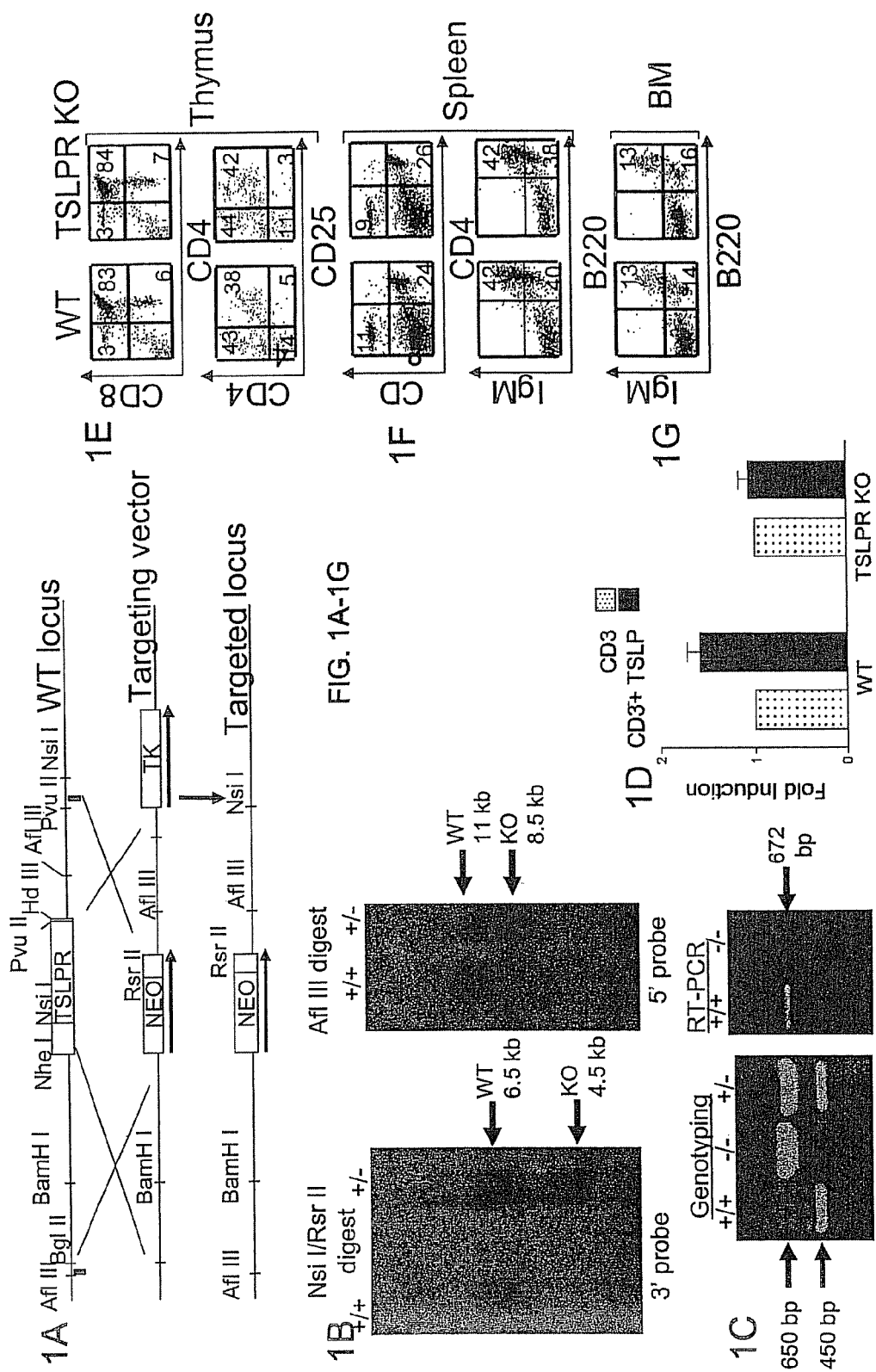
FIGS. 1A-1G are a graphs and digital images of results obtained from TSLPR KO mice.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-5 are amino acid sequences of TSLP polypeptides.

SEQ ID NOs: 6-10 are the nucleic acid sequences of primers or probes.

SEQ ID NO: 11 is an exemplary sequence of a polynucleotide encoding TSLP.

DETAILED DESCRIPTION

I. Abbreviations $\gamma_C$: common cytokine receptor gamma (γ) chain
Ab: antibody
APC: antigen presenting cell
CDR: complementarity-determining regions
CFSE: carboxy fluorescein diacetate succinimide ester
DC: dendritic cell
DN: double negative
DP: double positive (for example CD4$^+$CD8$^+$)
ES: embryonic stem cells
FACS: fluorescence activated cell sorting or scanning
HIV: human immunodeficiency virus
Hr or h: hour
IFN: interferon
Ig: immunoglobulin
IL: interleukin
i.p.: intraperitoneal
i.v.: intravenous
JAK: Janus Activated Kinase
kb: kilobases
KO: knock-out
min: minutes
NK: natural killer cell
OVA: ovalbumin
PBS: phosphate buffered saline
PCR: polymerase chain reaction
S.D.: standard deviation
sec: seconds
SCID: severe combined immunodeficiency disease
SP: single positive (for example, either CD4$^+$ or CD8$^+$)
STAT: Signal Transducer and Activator of Transcription TCR: T cell receptor
TG or Tg: transgenic
TSLP: thymic stromal lymphopoietin
TSLPR: thymic stromal lymphopoietin receptor
μg: microgram
vs.: versus
WT: wild-type II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Agent: Any polypeptide, compound, small molecule, organic compound, salt, polynucleotide, or other molecule of interest.

Agonist/Antagonist: An agent that has affinity for and stimulates physiologic activity at cell receptors normally stimulated by naturally occurring substances, thus triggering a biochemical response. A TSLP receptor agonist has affinity for the TSLP receptor and stimulates an activity induced by the binding of TSLP with its receptor. For example, a TSLP/TSLP receptor agonist is a molecule that binds to the TSLP receptor and induces intracellular signaling. In contrast, an "antagonist" is an agent that inhibits activity of a cell receptor normally stimulated by a naturally occurring substance. Accordingly, a TSLP/TSLP receptor antagonist binds to TSLP or to the TSLP receptor and inhibits binding of TSLP to the TSLP receptor and/or inhibits an activity normally induced by binding of TSLP with its receptor. For example, a TSLP/TSLP receptor antagonist can bind to TSLP or to the TSLP receptor and diminish or prevent binding, for example, by blocking binding, of TSLP to the TSLP receptor. Alternatively, a TSLP/TSLP receptor antagonist can bind to the TSLP receptor and diminish or prevent downstream signaling that would normally be induced by the binding of TSLP with its receptor. Agonists and antagonists can include a variety of classes of molecules including polypeptides, such as ligand-like polypeptides, antibodies, and fragments or subsequences thereof. Agonists and antagonists can also include fusion polypeptides, antibodies, peptides (such as peptides of less than about 20 amino acids in length), and small molecules. Exemplary antagonists include: neutralizing antibodies specific for TSLP and the TSLP receptor, soluble TSLP receptor molecules, and TSLP receptor fusion proteins, such as TSLPR-immunoglobulin Fc molecules or polypeptides that encode components of more than one receptor chain, that thereby mimic a physiological receptor heterodimer or higher order oligomer. If the receptor is a includes more than one polypeptide chain, a single chain fusion can be utilized.

Animal: A living multicellular vertebrate organism, a category which includes, for example, mammals and birds. A "mammal" includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope (e.g., as an antigen, such as TSLP or a fragment thereof, or a TSLP receptor of a fragment thereof). This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, Pierce Catalog and Handbook, 1994-1995 (Pierce Chemical Co., Rockford, Ill.); Kuby, J., *Immunology*, 3$^{rd}$ Ed., W. H. Freeman & Co., New York, 1997.

Typically, an immunoglobulin has a heavy and a light chain. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical.

Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (e.g., see U.S. Pat. No. 5,585,089).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. An "antigen presenting cell" is a cell that presents an antigen to the immune system. There are three general classes of antigen presenting cells (APCs): macrophages, dendritic cells, and B cells, although neutrophils can also present antigens. Processing and surface presentation of antigen by APCs can be thought of as a first step in the normal immune response. The antigen can be any antigen, including but not limited to an antigen of a bacterial, virus, fungus, or any other infectious organism.

Anti-Inflammatory Agent: Any of various medications that decrease the signs and symptoms (for example, pain, swelling, or shortness of breath) of inflammation. Corticosteroids are exemplary potent anti-inflammatory medications. Non-steroidal anti-inflammatory agents are also effective exemplary anti-inflammatory agents and do not have the side effects that can be associated with steroid medications.

Asthma: A clinical syndrome characterized by recurrent episodes of airway obstruction that resolve spontaneously or as a result of treatment. The resolution of the airway obstruction is a feature that distinguishes it from forms of chronic obstructive pulmonary disease. Asthma is also associated with hyperresponsiveness of the airways to a variety of inhaled stimuli; this condition is manifested as an exaggerated bronchoconstrictor response to stimuli that have little or no effect in normal subjects. Asthma is sometimes referred to as reactive airway disease.

Episodic airway narrowing constitutes an "asthma attack," and results from obstruction of the airway lumen to airflow. Three distinct pathological processes account for the obstruction: (1) constriction of airway smooth muscle, (2) thickening of airway epithelium, and (3) the presence of liquids within the confines of the airway lumen. It has been hypothesized that constriction of airway smooth muscle is due to the local release of bioactive mediators or neurotransmitters. During an asthma attack, patients experience shortness of breath accompanied by cough, wheezing and anxiety. Dyspnea may occur with exercise. In one embodiment, asthma is diagnosed by the presence of symptoms (such as recurrent cough, wheezing or dyspnea), and the presence of reversible airflow limitation (such as diminished forced expiratory volume in one second (FEV1), or in peak expiratory flow rate either spontaneously or with an inhaled short-acting beta2-agonist), or increased airway responsiveness to methacholine).

Bronchodilator: An antispasmodic or other agent that dilates a bronchus or bronchiole. Bronchodilators relax the smooth muscles of the airways, allowing the airway to dilate. Bronchodilator medicines do not counteract inflammation.

CD4: Cluster of differentiation 4 polypeptide, a T cell surface protein that mediates interaction with the MHC Class II molecule. CD4 also serves as the primary receptor site for HIV on T cells during HIV infection.

The known sequence of the CD4 precursor has a hydrophobic signal peptide, an extracellular region of approximately 370 amino acids, a highly hydrophobic stretch with significant identity to the membrane-spanning domain of the Class II MHC beta chain, and a highly charged intracellular sequence of 40 resides (Maddon, *Cell* 42:93, 1985).

CD8: Cluster of differentiation 8 polypeptide, a T cell surface protein that mediates interaction with MHC Class I molecule. CD8 occurs either as a disulfide-linked homodimer or homomultimer of two 34 kDa subunits (CD8α) or as a heterodimer complexed with another protein named CD8β, of which there are multiple forms arising by alternative splicing of its mRNA.

T cell progenitors in the thymus initially do not express CD8 or CD4. These progenitors develop into mature T cells in several steps. Immature thymocytes coexpress CD8 and CD4 (DP or CD4$^+$CD8$^+$ cells), and these cells give rise to mature T cells which are either CD4$^+$CD8$^-$ or CD4$^-$CD8$^+$ (also called SP cells). Those T cells that recognize self-MHC are selected to mature by a process known as positive selection in which Class I MHC generates an instructive signal that directs differentiation to a CD8 lineage.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Chronic Bronchitis: A long-standing inflammation of the airways that produces a lot of mucus, causing wheezing and infections. It is considered chronic if a subject has coughing and mucus on a regular basis for at least three months a year and for two years in a row.

Chronic Obstructive Pulmonary Disease (COPD): COPD refers mainly to two closely related respiratory disorders that cause gradual loss of pulmonary function: chronic bronchitis and emphysema associated with airflow obstruction. A subject with COPD sometimes has both chronic bronchitis and emphysema, or may just have one of these diseases. Chronic bronchitis is a long-standing inflammation of the airways that produces a lot of mucus, causing wheezing and infections. It is considered chronic if a subject has coughing and mucus on a regular basis for at least three months a year and for two years in a row. Emphysema is a disease that destroys the alveolae and/or bronchae. Simply put, the lungs lose elasticity. This causes the air sacs to become enlarged, thus making breathing difficult.

In the beginning stages of COPD, a subject may have only a mild shortness of breath and occasional coughing spells. Initial symptoms can include a general feeling of illness, increasing shortness of breath, coughing and wheezing. But, as the disease progresses, symptoms become increasingly more severe.

The majority of COPD subjects have a history of smoking. In addition, untreated or under-treated asthma may lead to irreversible lung damage. These subjects may have symptoms somewhat similar to COPD.

Comprises: A term that means "including." For example, "comprising A or B" means including A or B, or both A and B, unless clearly indicated otherwise.

Conservative substitutions: Modifications of a polypeptide that involve the substitution of one or more amino acids for amino acids having similar biochemical properties that do not result in change or loss of a biological or biochemical function of the polypeptide. These "conservative substitutions" are likely to have minimal impact on the activity of the resultant protein. Table 1 shows amino acids that may be substituted for an original amino acid in a protein, and which are regarded as conservative substitutions.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In one embodiment, one or more conservative changes, or up to ten conservative changes, can be made in a polypeptide without changing a biochemical function of the polypeptide. More substantial changes in a biochemical function or other protein features may be obtained by selecting amino acid substitutions that are less conservative than those listed in Table 1. Such changes include, for example, changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Cytokine/Interleukin (IL): A generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many growth factors and cytokines act as cellular survival factors by preventing programmed cell death. Cytokines and interleukins include both naturally occurring peptides and variants that retain full or partial biological activity. Although specific cytokines/interleukins are described in the specification, they are not limited to the specifically disclosed peptides.

Cystic Fibrosis: A disease that most commonly affects the lungs and digestive systems, especially the pancreas. It causes the exocrine glands, which produce mucus and sweat, to produce abnormal secretions. Cystic fibrosis causes the cells in the lung tissue to produce an abnormal amount of thick, sticky mucus that clogs the airways of the lungs, resulting in pulmonary obstructions and life-threatening bacterial infections.

DNA: Deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Deletion: The removal of a sequence of DNA, the regions on either side being joined together.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expectorant: A drug or chemical substance that induces the ejection of mucus, phlegm and other fluids from the lungs and air passages, for example by coughing.

Expiratory Flow Rate: The rate at which air is expelled from the lungs during exhalation. A subject's maximum expiratory flow is measured by a simple pulmonary test; in performing the test, a subject first takes as deep a breath as possible, then exhales as rapidly and as completely as possible into a machine known as a spirometer, which measures the rate of exhalation. Forced expiratory flow 25-75 (FEF 25-75) is a measurement of the forced expiratory flow determined over the midportion of a forced exhalation. An increase in the forced expiratory flow (FEF) or FEF 25-75 reflects a decrease in bronchoconstriction and an improvement in pulmonary function.

Forced Expiratory Volume (FEV): The forced expiratory volume is the volume of air resulting from the forced expiratory flow test in which a subject first inspires maximally to the total lung capacity, then exhales as rapidly and as completely as possible. The forced expired volume in one second (FEV1) represents the maximum expiratory air volume a subject can produce during a one-second interval. An increase in FEV or FEV1 reflects a decrease in bronchoconstriction and an improvement in pulmonary function.

Forced Vital Capacity (FVC): The volume of air resulting from the forced expiratory flow test in which a subject first inspires maximally to the total lung capacity, then exhales as rapidly and as completely as possible. An increase in FVC reflects a decrease in bronchoconstriction and an improvement in pulmonary function.

Functional fragments, derivatives and variants of a polypeptide: Includes those fragments and variants that maintain one or more functions of the parent polypeptide. It is recognized that the gene or cDNA encoding a polypeptide can be considerably mutated without materially altering one or more the polypeptide's functions. First, the genetic code is well known to be degenerate, and thus different codons encode the same amino acids. Second, even where an amino acid substitution is introduced, the mutation can be conservative and have no material impact on the essential functions of a protein. See Stryer, *Biochemistry* 3rd Ed., 1988. Third, part of a polypeptide chain can be deleted without impairing or eliminating all of its functions. Fourth, insertions or additions can be made in the polypeptide chain, for example, adding epitope tags—without impairing or eliminating its functions (Ausubel et al., *J. Immunol.* 159:2502, 1997). Other modifications that can be made without materially impairing one or more functions of a polypeptide include, for example, in vivo or in vitro chemical and biochemical modifications or which incorporate unusual amino acids. Such modifications include, for example, acetylation, carboxylation, phosphorylation, glycosylation, ubiquination, labeling, e.g., with radionucleotides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

A functional fragment or variant of TSLP is a polypeptide which binds to the TSLP receptor and induces a biological activity of TSLP, as described in U.S. Pat. No. 6,555,520, which is incorporated herein by reference. It includes any polypeptide twenty or more amino acid residues in length. Examples of functional fragments of TSLP include an N-terminal hydrophobic region that functions as a signal polypeptide, or the cytoplasmic domain. Additional examples are amino acids 29-159 of SEQ ID NO: 1, and a fragment having an N-terminus at amino acid 35 and a C-terminus at amino acid 159. Variants include amino acid sequences that are at least about 80% identical to SEQ ID NO: 1, such as a polypeptide at least 90%, 95%, 97%, 98%, or 99% identical to SEQ ID NO: 1. Additional variants of TSLP include those resulting from alternative splicing, and proteins in which differences in amino acid sequence are attributable to genetic polymorphism (allelic variation in individuals expressing the protein). Other derivatives include fusion proteins, such as those including poly-histidine sequence or an identifiable polypeptide tag, and different glycosylation patterns. These and additional fragments, variants and derivatives of TSLP are disclosed in U.S. Pat. No. 6,555,520, which is incorporated by reference herein.

$\gamma_c$ (common cytokine receptor gamma chain): A receptor subunit that has been shown to function as an essential signal-transducing component of various cytokine receptors, including receptors for IL-4, IL-7, IL-9, IL-15 and IL-21. The $\gamma_c$ subunit, together with a ligand-specific subunit, forms high-affinity receptors for the respective cytokine.

Gene: A DNA sequence that comprises control and coding sequences necessary for the production of a polypeptide or protein. The polypeptide can be encoded by a full-length coding sequence or by any portion of the coding sequence in some embodiments, so long as at least a portion of the desired activity of the polypeptide is retained. A "foreign" or "heterologous" gene sequence is any nucleic acid that is introduced into the genome of an animal by experimental manipulations. This can include gene sequences found in that animal so long as the introduced gene contains some modification (e.g., a point mutation, the presence of a selectable marker gene, a non-native regulatory sequence, or a native sequence integrated into the genome at a non-native location, etc.) relative to the naturally-occurring gene.

Inflammatory lung disease: Many diseases of the lung are associated with lung inflammation. For example, ARDS is the rapid onset of progressive malfunction of the lungs, and is usually associated with the malfunction of other organs due to the inability to take up oxygen. The condition is associated with extensive lung inflammation and small blood vessel injury in all affected organs. ARDS is commonly precipitated by trauma, sepsis (systemic infection), diffuse pneumonia and shock. It may be associated with extensive surgery, and certain blood abnormalities.

In many inflammatory lung diseases, the inflammatory response that accompanies the underlying disease state is much more dangerous than the underlying infection or trauma. Inflammatory lung diseases can include, but are not limited to pneumonia, ARDS, respiratory distress of prematurity, chronic bronchitis, COPD, cystic fibrosis, pulmonary fibrosis, and pulmonary sarcoidosis. Asthma can be an inflammatory lung disease, but does not necessarily have an inflammatory component.

Inflammatory response: An accumulation of white blood cells, either systemically or locally at the site of inflammation. The inflammatory response may be measured by many methods well known in the art, such as the number of white blood cells (WBC), the number of polymorphonuclear neutophils (PMN) and/or neutrophils, a measure of the degree of PMN activation, such as luminal enhanced-chemiluminescence, or a measure of the amount of cytokines present. Asthma can include an inflammatory response including for example, increased numbers and/or PMNs, eosinophils or mast cells.

Inspiratory Flow Rate: The rate at which air travels into the lungs during inspiration. Inspiratory flow is measured by a simple pulmonary test; in performing the test the subject takes as deep and rapid a breath as possible from a machine known as a spirometer, which measures the rate of inspiration. An increase in inspiratory flow rate reflects a decrease in bronchoconstriction and an improvement in pulmonary function.

Interleukin-7 (IL-7): Murine IL-7 is a glycoprotein of 25 kDa that contains six cysteine residues. It is derived from a precursor protein containing a classical secretory signal sequence of 25 amino acids. The disulfide bonds are essential for the biological activity of the protein. Human IL-7 includes 152 amino acids and has a molecular weight of 17.4 kDa. The human protein is 17 amino acids longer than the murine protein (the human gene contains an additional exon). Human and murine IL-7 (129 amino acids) have 60 percent sequence identity at the protein level. The human IL-7 gene maps to chromosome 8q12-q13, has a length of approximately 33 kb, and contains six exons. The murine IL-7 gene maps to chromosome 3, has a length of approximately 56 kb and contains five exons. IL-7 plays a role in both B and T cell proliferation.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Leukotriene Antagonist/Leukotriene Formation Inhibitor: Drugs that block the effects of leukotrienes (leukotriene antagonists) or inhibit the formation of leukotrienes (leukotriene formation inhibitors). Leukotrienes are substances that are associated with an allergic response and inflammation. In the airways, they cause bronchial or alveolar narrowing and increase secretions. Drugs can interfere with leukotriene action by inhibiting their synthesis (for example, zileuton, ZYFLO®, Abbott Laboratories) or blocking the receptor to which they bind (for example, monteleukast, SINGULAIR®, Merck and Company, and others).

Lung Volume: The maximum volume the lungs can hold.

Lymphocytes: A type of white blood cell that is involved in the immune defenses of the body. There are two main types of lymphocytes: B cells and T cells.

Natural Killer Cell: A large granular lymphocyte capable of killing a tumor or microbial cell without prior exposure to the target cell and without having it presented with or marked by a histocompatibility antigen.

Neutralizing amount: An amount of an agent sufficient to decrease the activity or amount of a substance to a level that is undetectable using standard method.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

A "therapeutically effective amount" is a quantity of a chemical composition or an anti-viral agent sufficient to achieve a desired effect in a subject being treated. For instance, this can be the amount necessary to inhibit viral replication or to measurably alter outward symptoms of the viral infection, such as increase of T cell counts in the case of an HIV infection. In general, this amount will be sufficient to measurably inhibit virus (e.g., HIV) replication or infectivity. When administered to a subject, a dosage will generally be used that will achieve target tissue concentrations (for example, in lymphocytes) that has been shown to achieve in vitro inhibition of viral replication.

Pharmaceutically acceptable carriers (excipients): The pharmaceutically acceptable carriers useful with the methods described herein are conventional. *Remington's Pharmaceutical Sciences*, by E. W. Martin, Mack Publishing Co., Easton, Pa., 15th Edition (1975), describes compositions and formulations suitable for pharmaceutical delivery of the cytokines and cells disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as ADP-ribosylated proteins, ribosyl-proteins, and glycoproteins. The term polypeptide is specifically intended to cover naturally occurring proteins, such as TSLP, as well as polypeptides (for example, TSLP or a fragment thereof) that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Probes and primers: Nucleic acid probes and primers can be readily prepared based on a nucleic acid sequence. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al., in *Molecular Cloning: A Laboratory Manual*, CSHL, New York, 1989, and Ausubel et al., in *Current Protocols in Molecular Biology*, Greene Publ. Assoc. and Wiley-Intersciences, 1992.

Primers are short nucleic acid molecules, preferably DNA oligonucleotides 10 nucleotides or more in length. More preferably, longer DNA oligonucleotides can be about 15, 17, 20 or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al., in *Molecular Cloning: A Laboratory Manual*, CSHL, New York, 1989; Ausubel et al., in *Current Protocols in Molecular Biology*, Greene Publ. Assoc. and Wiley-Intersciences, 1998; and Innis et al., *PCR Protocols, A Guide to Methods and Applications*, Academic Press, Inc., San Diego, Calif., 1990. PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of the TSLP encoding nucleotide will anneal to a target sequence, such as another nucleic acid encoding TSLP, with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of the nucleotide sequence of interest.

Protein: A biological molecule expressed by a gene and comprised of amino acids. Also termed "polypeptide."

Pulmonary function: The function of the respiratory system, which can be measured through a variety of tests, including, but not limited to measurements of airflow (e.g. spirometry) or arterial blood gases. Measurements of airflow included airflow rate, peak expiratory flow rate (PEFR), forced expiratory volume in the first second ($FEV_1$), and maximal midexpiratory rate (MMEFR). A decrease in airflow rates throughout the vital capacity is the cardinal pulmonary function abnormality in asthma. Although essential for the diagnosis of asthma, it is not specific, as other obstructive diseases share this feature. The PEFR, $FEV_1$, and MMEFR can all be decreased in asthma. The severity of the attack of asthma can be assessed by objective measurements of airflow.

Purified: The term "purified" does not require absolute purity; rather, it is intended as a relative term. Thus, for example, a purified protein preparation is one in which the protein referred to is more pure than the protein in its natural environment within a cell.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Respiratory Disorder: A large variety of abnormalities arising in all the different structures of the body involved with gas exchange. These structures include the lungs, nose, oropharynx, extrapulmonary airways, thoracic cage and respiratory muscles. Respiratory disorders encompass both acute and chronic diseases. Asthma is one specific, non-limiting example of a respiratory disorder. Other specific non-limiting examples include, but are not limited to, coughs, pneumonia, bronchitis, such as chronic obstructive bronchitis, and emphysema, interstitial lung disease, cystic fibrosis and lung tumors.

Rhino-conjunctivitis: A set of conditions that affect a subject's conjunctiva and/or nasal membranes. Subjects affected with rhino-conjunctivitis include subjects that have rhinitis, conjunctivitis, and that symptoms associated with both conditions.

Allergic rhinitis is characterized by sneezing, rhinorrhea, obstruction of the nasal passages, conjunctival, nasal and pharengeal itching, and lacrimation. These symptoms all occur in a temporal relation to allergen expose. The three forms of allergic rhinitis are Allergic conjunctivitis is extremely common. Three forms are recognized with closely overlapping manifestations. Hay fever conjunctivitis has a seasonal incidence related to the release of airborne antigens. Vernal conjunctivitis is also seasonal, becoming worse in warm months. Atopic conjunctivitis occurs in subjects with atopic dermatitis and asthma. Airbourne antigens are associated with all three forms.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the human CD4 protein, and the corresponding cDNA sequence, will possess a relatively high degree of sequence identity when aligned using standard methods. This homology will be more significant when the orthologous proteins or cDNAs are derived from species which are more closely related (e.g., human and chimpanzee sequences), compared to species more distantly related (e.g., human and murine sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-244, 1988; Higgins & Sharp, *CABIOS* 5:151-153, 1989; Corpet et al., *Nuc. Acids Res.* 16:10881-90, 1988; Huang et al., *Computer Appls. in the Biosciences* 8:155-65, 1992; and Pearson et al., *Meth. Mol. Bio.* 24:307-31, 1994. Altschul et al., *J. Mol. Biol.* 215:403-410, 1990, presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

Homologs of the disclosed human CD4 protein typically possess at least 60% sequence identity counted over full-length alignment with the amino acid sequence of human CD4 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described in the NCBI website. These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al., *Molecular Cloning: A Laboratory Manual*, CSHL, New York, 1989, and Tijssen, *Laboratory Techniques in Biochemistry and Molecular Biology—Hybridization with Nucleic Acid Probes* Part I, Chapter 2, Elsevier, New York, 1993. Nucleic acid molecules that hybridize under stringent conditions to a given sequence will typically hybridize under wash conditions of 2×SSC at 50° C.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Selection markers or selectable markers: Refers to the use of a gene that encodes an enzymatic activity that confers resistance to an antibiotic or drug upon the cell in which the selectable marker is expressed. Selectable markers can be "positive;" positive selectable markers typically are dominant selectable markers, i.e. genes that encode an enzymatic activity that can be detected in any mammalian cell or cell line. Examples of dominant selectable markers include, but are not limited to, (1) the bacterial aminoglycoside 3' phosphotransferase gene (also referred to as the neo gene) which confers resistance to the drug G418 in mammalian cells, (2) the bacterial hygromycin G phosphotransferase (hyg) gene which confers resistance to the antibiotic hygromycin and (3) the bacterial xanthine-guanine phosphoribosyl transferase gene (also referred to as the gpt gene) which confers the ability to grow in the presence of mycophenolic acid. Selectable markers can be "negative;" negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. The terms are further defined, and methods further explained, by U.S. Pat. No. 5,464,764.

An animal whose genome "comprises a heterologous selectable marker gene" is an animal whose genome contains a selectable marker gene not naturally found in the animal's genome that is introduced by means of molecular biological methods. A heterologous selectable marker is distinguished from an endogenous gene naturally found in the animal's genome in that expression or activity of the heterologous selectable marker can be selected for or against.

Small Molecule: The term small molecule encompasses a wide variety of chemical compounds, including both inorganic and organic molecules. By definition, a molecule is the smallest unit of matter that can exist by itself while retaining its chemical properties. A macromolecule is a large molecule in which there is a large number of one or several relatively simple structural units, each consisting of several atoms bonded together, e.g., nucleic acids, polypeptides, polysaccharides. In the context of drug development, the term small molecule is used to refer to compounds that are not macromolecules (e.g., biological macromolecules such as nucleic acids, proteins, polypeptides, etc.). A small molecule is typically made up of a single structural and functional unit or a small number of simple structural units. Small molecules are purified or isolated from natural products, or can be produced synthetically. Frequently, small molecules are members of libraries produced by combinatorial chemistry. Typically, a small molecule is less than about 1000 Daltons.

Specific binding agent: An agent that binds substantially only to a defined target. In one embodiment, the specific binding agent is a monoclonal or polyclonal antibody that specifically binds TSLP, or its receptor. Thus a TSLP receptor specific binding agent is an agent that binds substantially to a TSLP receptor.

The term "specifically binds" refers with respect to an antigen, such as the TSLP or its receptor, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the receptor or antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to TSLP, or a cell or tissue bearing TSLP receptor as compared to a different polypeptide or to a cell or tissue lacking TSLP receptor, respectively. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

T Cell: A white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also commonly known as helper T cells, help orchestrate the immune response, including antibody responses as well as killer T cell responses. CD8+ T cells carry the "cluster of differentiation 8" (CD8) marker. In one embodiment, a CD8 T cell is a cytotoxic T lymphocytes. In another embodiment, a CD8 cell is a suppressor T cell.

Thymic Stromal Lymphopoietin (TSLP): A growth factor that binds a specific receptor and stimulates lymphocyte proliferation. TSLP is known to play a role in B cell development and maturation. Amino acid sequences of TSLP, functional variants, derivatives and fragments thereof, are provided in U.S. Pat. No. 6,555,520, which is incorporated herein by reference. Nucleic acid sequences encoding these polypeptides are also provided in U.S. Pat. No. 6,555,520.

TSLP has been shown to induce activation and phosphorylation of STAT-3 and STAT-5 but does not activate any of the four known Janus kinases. TSLP mediated activation of STAT-5 can be uncoupled from cell proliferation.

The TSLP receptor has been shown to be a member of the hematopoietin receptor superfamily. The receptor has been cloned and the murine counterpart of which has been identified as delta-1. High affinity binding sites require the presence of the alpha chain of the IL-7 receptor. The receptor complex does not involve common gamma ($\gamma_c$), a signal-transducing component of various cytokine receptors, including receptors for IL-2, IL-4, IL-7, IL-9, IL-15, and IL-21.

Treatment: Refers to both prophylactic inhibition of initial infection, and therapeutic interventions to alter the natural course of an untreated disease process, such as infection with a virus (e.g., HIV infection).

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

HIV is a retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or Western blot studies. Laboratory findings associated with this disease are a progressive decline in T-helper cells.

The treatment of HIV disease has been significantly advanced by the recognition that combining different drugs with specific activities against different biochemical functions of the virus can help reduce the rapid development of drug resistant viruses that were seen in response to single drug treatment. In addition, discontinuation of existing therapies results in a rapid rebound of viral replication, indicating the lack of complete HIV eradication by the drugs. There is therefore a continuing need for the development of new anti-retroviral drugs that act specifically at different steps of the viral infection and replication cycle.

Wild-type: The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and/or functional properties (i.e. altered characteristics) when compared to the wild-type gene or gene product. It is noted that naturally-occurring mutants can be isolated; these are typically identified by the fact that they have altered characteristics when compared to the wild-type gene or gene product.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents and other references mentioned herein are incorporated by reference in their entirety. In case of conflict, the present specification, including explanations of terms, will control. In addition, the materials, methods and examples are illustrative only and not intended to be limiting.

Methods for Inducing Proliferation of CD4+ T cells

A method is provided herein for inducing the proliferation of CD4+ T cells. In one embodiment, the method includes isolating CD4+ T cells and contacting them with a therapeutically effective amount of TSLP, or a TSLP receptor agonist, thereby inducing proliferation of the CD4+ T cells.

Amino acid sequences of TSLP, functional variants, derivatives and fragments thereof, are provided in U.S. Pat. No. 6,555,520, which is incorporated herein by reference. Nucleic acid sequences encoding these polypeptides are also provided in U.S. Pat. No. 6,555,520, which is incorporated by reference. In one specific example, a full-length TSLP polypeptide is human TSLP and has an amino acid sequence set forth as:

```
                                            (SEQ ID NO: 1)
mfpfallyvl  svsfrkifil  qlvglvltyd  ftncdfekik aaylstiskd  litymsgtks  tefnnntvscs  nrphclteiq sltfnptagc  aslakemfam  ktkaalaiwc  pgysetqina tqamkkrrkr  kvttnkcleq  vsqlqglwrr  fnrpllkqq
```

In another example, a full-length TSLP polypeptide is a murine polypeptide has an amino acid sequence set forth as:

```
mvllrslfil  qvlvrmglty  nfsncnftsi  tkiycniifh dltgdlkgak  feqiedcesk  pacllkieyy  tlnpipgcps lpdktfarrt  realndhcpg  ypeterndgt  qemaqevqni clnqtsqilr  lwysfmqspe
(mouse TSLP, GenBank Accession No. NP_607342,
SEQ ID NO: 2)
or mravtwaiva  mllprvlgai  ptrtprtggv  gdtlsvaivc hdlesvevtw  gpgsahhgls  anlslefryg  nqvpqpcphy flldsvragc  vlpmgkglle  vvlregggak  lfsrkkkasa wlrprppwnv  tlswvgdtva  vscpshsypg  leyevqhrdd fdpewqstsa  pfcnltvggl  dpgrcydfrv  ratpqdfyyg pearpskwtg  vaslqgvgpt  gsctgptlpr  tpgtptppla lacglavall  tlvlllallr  mrrvkeallp  gvpdprgsfp glfekhhgnf  qawiadsqaa  vptvpeqdkd  ddvirpqtkg vetqedddvi  apgspclggg  almsvggasf  lmgdsgyttl
(rat TSLP, GenBank Accession No. NP_604460,
SEQ ID NO: 3)
```

Additional TSLP polypeptides have the following amino acid sequence:

```
mktkaalaiw  cpgysetqin  atqamkkrrk  rkvttnkcle qvsqlqglwr  rfnrpllkqq
(human isoform 2, GenBank Accession No. AAH16720,
SEQ ID NO: 4)
```

Another TSLP polypeptide has the following amino acid sequence:

```
mkclgqskke  evsfrkifil  qlvglvltyd  ftncdfekik aaylstiskd  litymsgtks  tefnnntvscs  nrphclteiq sltfnptagc  aslakemfam  ktkaalaiwc  pgysetqina tqamkkrrkr  kvttnkcleq  vsqlqglwrr  fnrpllkqq
(GenBank Accession No. AAH40592,
SEQ ID NO: 5)
```

The polypeptide set forth as SEQ ID NO: 1 includes an N-terminal hydrophobic region (amino acids 1-28) that functions as a signal polypeptide, and a cleavage signal at amino acid 34. Thus, functional fragments of SEQ ID NO: 1 include amino acids 29-159 of SEQ ID NO: 1 and amino acids 35-159 of SEQ ID NO: 1. In addition, functional polypeptides include fusion polypeptides including poly-histidine, an antigenic epitope or a FLAG polypeptide, the sequences of which are set forth in U.S. Pat. No. 6,555,520, which is herein incorporated by reference.

A method is provided herein for stimulating T cell proliferation. The method includes contacting isolated mammalian $CD4^+$ T cells with an effective amount of a thymic stromal derived lymphopoietin (TSLP) polypeptide.

In one specific, non-limiting example, the population of T cells includes $CD4^+$ T cells as greater than 50% of the population, greater than 80% of the population, greater than 90% of the population, greater than 95% of the population, or greater than 99% of the population. A variety of methods can be used in order to purify $CD4^+$ T cells.

In one embodiment, suspension of cells is produced, and antibodies that specifically bind CD4 are reacted with the cells in suspension. Methods of determining the presence or absence of a cell surface marker, such as CD4, are well known in the art. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies, see Haugland, R. P., *Molecular Probes: Handbook of Fluorescent Probes and Research Chemicals* (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I and amino acids comprising any radionucleotides, including, but not limited to, $^{14}$C, $^{3}$H and $^{35}$S.

Fluorescence activated cell sorting (FACS) can be used to sort cells that express CD4, by contacting the cells with an appropriately labeled antibody. In one embodiment, additional antibodies and FACS sorting can further be used to produce substantially purified populations of $CD4^+$ T cells.

A FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells. (For exemplary methods of FACS, see U.S. Pat. No. 5,061,620, herein incorporated by reference).

However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures can include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g. CD4) to bind to the solid-phase linked antibodies. The bound cells are then separated from the solid phase by any appropriate method, depending mainly upon the nature of the solid phase and the antibody employed.

Antibodies may be conjugated to biotin, which then can be removed with avidin or streptavidin bound to a support, or fluorochromes, which can be used with a fluorescence activated cell sorter (FACS), to enable cell separation (see above).

Polynucleotides encoding TSLP are also of use in the methods disclosed herein (see U.S. Pat. No. 6,555,520, herein incorporated by reference). For example, one such polynucleotide includes (SEQ ID NO: 11):

as long as they encode a polypeptide that has an activity of TSLP, such as the ability to induce proliferation of a CD4$^+$ T cell. Such polynucleotides include naturally occurring, synthetic, and intentionally manipulated polynucleotides. For example, a polynucleotide encoding may be subjected to site-directed mutagenesis. The polynucleotides include sequences that are degenerate as a result of the genetic code, but encode TSLP. There are 20 natural amino acids, most of which are specified by more than one codon. Therefore, all degenerate nucleotide sequences are of use in the methods disclosed herein as long as the amino acid sequence of the TSLP encoded by the nucleotide sequence is functionally unchanged.

DNA sequences encoding TSLP can be expressed in vitro (or in vivo) by DNA transfer into a suitable host cell. Methods of stable transfer, meaning that the foreign DNA is continuously maintained in the host, are known in the art. Polynucleotide sequences encoding TSLP can be inserted into an expression vector, such as a plasmid, virus or other vehicle known in the art that has been manipulated by insertion or incorporation of the TSLP sequences. Polynucleotide sequences which encode TSLP can be operatively linked to expression control sequences. In one embodiment, an expression control sequence operatively linked to a coding sequence is ligated such that expression of the coding sequence is achieved under conditions compatible with the expression control sequences.

The polynucleotide encoding TSLP, such as human TSLP, can be inserted into an expression vector that contains a promoter sequence which facilitates the efficient transcription of the inserted genetic sequence by the host. The expression vector typically contains an origin of replication, a promoter, as well as specific genes that allow phenotypic selection of the transformed cells. Vectors suitable for use

```
  1 GCAGCCAGAA AGCTCTGGAG CATCAGGGAG ACTCCAACTT AAGGCAACAG

51 CATGGGTGAA TAAGGGCTTC CTGTGGACTG GCAATGAGAG GCAAAACCTG

101 GTGCTTGAGC ACTGGCCCCT AAGGCAGGCC TTACAGATCT CTTACACTCG

151 TGGTGGGAAG AGTTTAGTGT GAAACTGGGG TGGAATTGGG TGTCCACGTA

201 TGTTCCCTTT TGCCTTACTA TATGTTCTGT CAGTTTCTTT CAGGAAAATC

251 TTCATCTTAC AACTTGTAGG GCTGGTGTTA ACTTACGACT TCACTAACTG

301 TGACTTTGAG AAGATTAAAG CAGCCTATCT CAGTACTATT TCTAAAGACC

351 TGATTACATA TATGAGTGGG ACCAAAAGTA CCGAGTTCAA CAACACCGTC

401 TCTTGTAGCA ATCGGCCACA TTGCCTTACT GAAATCCAGA GCCTAACCTT

451 CAATCCCACC GCCGGCTGCG CGTCGCTCGC CAAAGAAATG TTCGCCATGA

501 AAACTAAGGC TGCCTTAGCT ATCTGGTGCC CAGGCTATTC GGAAACTCAG

551 ATAAATGCTA CTCAGGCAAT GAAGAAGAGG AGAAAAGGA AAGTCACAAC

601 CAATAAATGT CTGGAACAAG TGTCACAATT ACAAGGATTG TGGCGTCGCT

651 TCAATCGACC TTTACTGAAA CAACAGTAAA CCATCTTTAT TATGGTCATA

701 TTTCACAGCC CAAAATAAAT CATCTTTATT AAGTAAAAAA AAA
```

One of skill in the art, using the genetic code, can readily identify degenerate variants of SEQ ID NO: 11, which also encode TSLP. Polynucleotides include DNA, cDNA and RNA sequences which encode a TSLP. It is understood that all polynucleotides encoding TSLP are also included herein, include, but are not limited to, the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding TSLP can be expressed in either prokaryotes or eukaryotes. Hosts can include microbial, yeast, insect and mammalian organisms. Methods of expressing DNA sequences having eukaryotic or viral sequences in prokaryotes are well known in the art. For example, biologically functional viral and plasmid DNA vectors capable of expression and replication in a host are known in the art. Such vectors are used to incorporate a DNA sequence encoding TSLP. Transfection of a host cell with recombinant DNA can be carried out by conventional techniques and are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Methods of Treating an Immunodeficiency

The present methods also include administration of a therapeutically effective amount of a TSLP polypeptide disclosed herein, a TSLP receptor agonist, or a nucleic acid encoding TSLP to treat an immunodeficiency, or a disease process in which increased numbers, proliferation, or function of $CD4^+$ T cells is desired. In one embodiment, the disease is a viral disease, such as infection with an immunodeficiency virus. In one example, the immunodeficiency virus is a human immunodeficiency virus (HIV), such as HIV-1 or HIV-2. In another example, the subject has an immunodeficiency as a result of a genetic disorder, such as severe combined immunodeficiency (SCID). In a further embodiment, the subject has acquired the immunodeficiency as a result of an environmental exposure or administration of an agent. For example, the agent can be radiation or a chemotherapeutic agent. Generally, the administration of the TSLP polypeptide, TSLP receptor agonist, or nucleic acid encoding TSLP reduces a sign or a symptom of the disorder. For example, the administration can result in increased number or function of $CD4^+$ cells.

A TSLP polypeptide or TSLP agonist can be included in a pharmaceutical formulation in an amount per unit dose sufficient to evoke proliferation of $CD4^+$ cells in the subject to be treated. The response can be the reduction of any other detrimental effect of the disease (e.g., reduction in HIV protease activity, see U.S. Pat. No. 5,171,662), regardless of whether the protection is partial or complete. The composition can be administered to the subject by any suitable means. Examples are by oral administration, intramuscular injection, subcutaneous injection, intravenous injection, intraperitoneal injection, eye drop or by nasal spray.

The dose of a TSLP polypeptide or other TSLP receptor agonist can vary according to factors such as the disease state, age, sex, immune status, and weight of the individual, and the ability to elicit a desired response in the individual. Dosage regime may be adjusted to provide the optimum therapeutic response. For example, several divided doses may be administered daily or the dose may be proportionally reduced as indicated by the therapeutic situation. In therapeutic applications, compositions are administered to a subject having a disorder in a therapeutically effective amount, which is an amount sufficient to cure or at least partially arrest the disease or a sign or symptom of the disorder. Amounts effective for this use will depend upon the severity of the disorder and the general state of the patient's health. An effective amount of the compound is that which provides either subjective relief of a symptom(s) or an objectively identifiable improvement as noted by the clinician or other qualified observer.

A TSLP polypeptide or a TSLP receptor agonist can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal or anal administration is contemplated. In one embodiment, administration is by subcutaneous or intramuscular injection. To extend the time during which the peptide or protein is available to stimulate a response, a peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release.

Thus, examples of compositions include liquid preparations for orifice (e.g., oral, nasal, anal, vaginal, peroral, intragastric) administration such as suspensions, syrups or elixirs; and preparations for parenteral, subcutaneous, intradermal, intramuscular or intravenous administration (e.g., injectable administration, including the use of needleless injectors) such as sterile suspensions or emulsions, are provided. In such compositions the antigen(s) may be in admixture with a suitable carrier, diluent, or excipient such as sterile water, physiological saline, glucose or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as *Remington's Pharmaceutical Science,* 17th edition, 1985, incorporated herein by reference, may be consulted to prepare suitable preparations, without undue experimentation. The compositions can also be lyophilized.

Suitable dosages can also be determined by one of skill in the art. For example, typical dosages of a TSLP polypeptide can be from about 5 µg/ml to about 150 µg/ml, and other dosages can be from about 15 to about 150 µg/dose. Single or multiple administrations of the compositions are administered depending on the dosage and frequency as required and tolerated by the subject. In one embodiment, the dosage is administered once as a bolus, but in another embodiment can be applied periodically until either a therapeutic result is achieved. Generally, the dose is sufficient to treat or ameliorate symptoms or signs of disease without producing unacceptable toxicity to the subject.

In another embodiment, a nucleic acid encoding a TSLP polypeptide is utilized (e.g., see Robinsion et al., *Nat. Med.*, 5(5):526-34, 1999). Thus, a method is provided for treating a viral infection, such as an HIV infection or an immunodeficiency, by providing a therapeutically effective amount of a nucleic acid encoding the TSLP polypeptide. Delivery of the polynucleotide encoding the CD4 fusion polypeptide can be achieved using a recombinant expression vector such as a chimeric virus or a colloidal dispersion system, or through the use of targeted liposomes. For example, about 10 µg to about 1 mg of DNA can be utilized, such as about 10-100 µg, or about 50 µg, of a DNA construct can be injected intradermally three times at two week intervals to produce the desired therapeutic effect Various viral vectors which can be utilized for administration of nucleic acids include, but are not limited to, adenoviral, herpes viral, or retroviral vectors. In one embodiment, a retroviral vector such as a derivative of a murine or avian retroviral vector is utilized. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). In addition, when the subject is a human, a vector such as the gibbon ape leukemia virus (GaLV) is utilized. A number of additional retroviral vectors can incorporate multiple genes. The vectors can transfer or incorporate a gene for a selectable marker so that transduced cells can be identified and generated. By inserting a nucleic acid encoding a TSLP polypeptide into the viral vector, along with another gene which encodes the ligand for a receptor on a specific target cell, for example, the vector is rendered target specific. Retroviral vectors can be made target specific by attaching, for example, a sugar, a glycolipid, or a protein. Targeting can also be accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines which have deletions of the packaging signal include, but are not limited to, Q2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for therapeutic TSLP polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 µm, can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988; see also U.S. Pat. No. 6,270,795).

The composition of the liposome is usually a combination of phospholipids, particularly high-phase-transition-temperature phospholipids, usually in combination with steroids, such as cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In embodiments wherein treatment of viral disease is desired, such as treatment with an infection with an immunodeficiency virus, the administration of a TSLP polypeptide, a TSLP receptor agonist, or a nucleic acid encoding TSLP, can be combined with administration of one or more antiviral drugs useful in the treatment of viral disease. For example, a TSLP polypeptide, TSLP receptor agonist, or a nucleic acid encoding TSLP, can be administered, whether before or after exposure to the virus, in combination with effective doses of other anti-virals, immunomodulators, anti-infectives, or vaccines. The term "administration" refers to both concurrent and sequential administration of the active agents.

It should be noted that pharmaceutical compounds including a therapeutically effective amounts of TSLP antagonists can also be prepared using the information provided.

In one embodiment, a combination of TSLP, or a nucleic aid encoding TSLP with one or more agents useful in the treatment of a viral disease is provided. In one specific, non-limiting example, the viral disease is a retroviral disease, such as an HIV-1-induced, an HIV-2-induced, a SIV-induced, or a FIV induced disease. Examples of anti-virals that can be used in the disclosed method are: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo Alto, Calif.), didehydrodeoxythymidine or d4T (from Bristol-Myers-Squibb), EL10 (from Elan Corp. of Gainesville, Ga.), dideoxycytidine or ddC (from Hoffmann-LaRoche), Novapren (from Novaferon Labs, Inc. of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immuno-modulators are AS-101 (Wyeth-Ayerst Labs.), bropirimine (Upjohn), gamma interferon (Genentech), GM-CSF (Genetics Institute), IL-2 (Cetus or Hoffmann-LaRoche), human immune globulin (Cutter Biological), IMREG (from Imreg of New Orleans, La.), SK&F106528, TNF (Genentech), and soluble TNF receptors (Immunex).

Examples of some anti-infectives used include clindamycin with primaquine (from Upjohn, for the treatment of *pneumocystis* pneumonia), fluconazlone (from Pfizer for the treatment of cryptococcal meningitis or candidiasis), nystatin, pentamidine, trimethaprim-sulfamethoxazole, and many others.

"Highly active anti-retroviral therapy" or "HAART" refers to a combination of drugs which, when administered in combination, inhibits a retrovirus from replicating or infecting cells better than any of the drugs individually. In one embodiment, the retrovirus is a human immunodeficiency virus. In one embodiment, the highly active anti-retroviral therapy includes the administration of 3'axido-3-deoxy-thymidine (AZT) in combination with other agents. Examples of agents that can be used in combination in HAART for a human immunodeficiency virus are nucleoside analog reverse transcriptase inhibitor drugs (NA), non-nucleoside analog reverse transcriptase inhibitor drugs (NNRTI), and protease inhibitor drugs (PI). One specific, non-limiting example of HAART used to suppress an HIV infection is a combination of indinavir and efavirenz, an experimental non-nucleoside reverse transcriptase inhibitor (NNRTI).

In one embodiment, HAART is a combination of three drugs used for the treatment of an HIV infection, such as the drugs shown in Table 2 below. Examples of three-drug HAART for the treatment of an HIV infection include 1 protease inhibitor from column A plus 2 nucleoside analogs from column B in Table 2. In addition, ritonavir and saquinavir can be used in combination with 1 or 2 nucleoside analogs.

TABLE 2

| Column A | Column B |
| --- | --- |
| indinavir (Crixivan) | AZT/ddI |
| nelfinavir (Viracept) | d4T/ddI |
| ritonavir (Norvir) | AZT/ddC |
| saquinavir (Fortovase) | AZT/3TC |
| ritonavir/saquinavir | d4T/3TC |

In addition, other 3- and 4-drug combinations can reduce HIV to very low levels for sustained periods. The combination therapies are not limited to the above examples, but include any effective combination of agents for the treatment of HIV disease (including treatment of AIDS). Administration of these agents is thus combined with the administration of TSLP, or a nucleic acid encoding TSLP.

In another embodiment a method is provided for treating an immunodeficiency by isolating $CD4^+$ T cells, contacting the $CD4^+$ T cells with an effective amount of a TSLP polypeptide, TSLP receptor agonist, or a nucleic acid encoding TSLP, and administering them to a subject. The $CD4^+$ T cells can be autologous (from the same subject) or heterologous (from a different subject). In one embodiment, the subject is human.

Fluorescence activated cell sorting (FACS) can be used to sort (isolate) cells $CD4^+$ T cells, by contacting the cells with an appropriately labeled antibody. In one embodiment, several antibodies (such as antibodies that bind CD4, CD3, and/or CD8) and FACS sorting can be used to produce substantially purified populations of $CD4^+$ T cells. These methods are known in the art.

As noted above, FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells. (For exemplary methods of FACS, see U.S. Pat. No. 5,061,620).

However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique (see above). Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g. CD4) to bind to the solid-phase linked antibodies. The bound cells are then separated from the solid phase by any appropriate method, depending mainly upon the nature of the solid phase and the antibody employed. Antibodies may be conjugated to biotin, which then can be removed with avidin or streptavidin bound to a support, or fluorochromes, which can be used with a fluorescence activated cell sorter (FACS), to enable cell separation.

For example, cells expressing CD4 are initially separated from other cells by the cell-surface expression of CD4. In one specific, non-limiting example, CD4+ cells are positively selected by magnetic bead separation, wherein magnetic beads are coated with CD4 reactive monoclonal antibody. The CD4+ cells are then removed from the magnetic beads.

Release of the CD4+ T cells from the magnetic beads can effected by culture release or other methods. Purity of the isolated CD4+ cells is then checked with a FACSCAN.RTM. flow cytometer (Becton Dickinson, San Jose, Calif.), for example, if so desired. In one embodiment, further purification steps are performed, such as FACS sorting the population of cells released from the magnetic beads. In one example, this sorting can be performed to detect expression of CD3 and/or CD8. The purified CD4+ T cells are then contacted with a therapeutically effective amount of TSLP, or a nucleic acid encoding TSLP. Subsequently, the expanded CD4+ T cells are then administered to the subject.

In one embodiment, CD4+ T cells are also contacted with an antigen. The antigen can be any polypeptide of interest, including a viral antigen, a bacterial antigen or a fungal antigen.

Examples of viruses include: Retroviridae (for example, human immunodeficiency viruses, such as HIV-1 (also referred to as HTLV-III, LAV or HTLV-III/LAV, or HIV-III; and other isolates, such as HIV-LP; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B Hepatitis (class 1=internally transmitted; class 2=parenterally transmitted (i.e., Hepatitis C); Norwalk and related viruses, and astroviruses). Examples of bacteria include: *Helicobacter pyloris, Borelia burgdorferi, Legionella pneumophilia, Mycobacteria* sps (such as *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*. Examples of fungi include, but are not limited to, *Cryptococcus neoformans, Histoplasma capsulatum, Coccidioides immitis, Blastomyces dermatitidis, Chlamydia trachomatis, Candida albicans*. Other infectious organisms (such as protists) include: *Plasmodium falciparum* and *Toxoplasma gondii*.

In one embodiment, isolated CD4+ T cells are contacted with an effective amount of TSLP, and are also contacted with an antigen. The antigen can be any polypeptide of interest, including any viral antigen, bacterial antigen, or fungal antigen, such as an antigen from one of the infectious organisms listed above.

Methods of Treating an Inflammatory Disorder

Methods are provided herein for treating an inflammatory disorder, such as (but not limited to) asthma. The method includes administering to a subject a therapeutically effective amount of a TSLP antagonist. Methods are also provided herein for treating immune-mediated disorders of the lung, such as asthma. In one example, the disorder is asthma, wherein the asthma is antigen-mediated. Methods are also disclosed for the treatment of an inflammatory disorder such as allergic rhinitis, allergic dermatitis, and allergic conjunctivitis. In one embodiment, the inflammatory disorder is an IgE-mediated disorder, such as a pulmonary IgE mediated disorder. For example, the disorder can be asthma or the disorder can be rhino-conjunctivitis.

Asthma (sometimes referred to as reactive airway disease) is a condition of the respiratory tract characterized by reversible narrowing of the airways (bronchoconstriction) and increased sensitivity (hyperresponsiveness) of the airways to a variety of stimuli. The familiar symptoms of asthma (such as coughing, wheezing, chest tightness, dyspnea) is caused by airway smooth muscle contraction, increased bronchial mucus secretion, and inflammation. Asthma has been estimated to affect 10-20% of school-aged children around the world, and hospital admissions for asthma in children have increased dramatically in recent years, one survey for the United States indicating that hospital admissions for children under 15 with asthma increased by at least 145% between 1970 and 1984 (See, Sears, in *Asthma as an Inflammatory Disease*, O'Byrne, (ed.), Marcel Dekker, Inc.; New York, 1990, pp. 15-48). Overall, it is estimated that 10 million Americans (4% of the population) have asthma, and even more than a decade ago about $4 billion was spent in treatment per year (Altman, *New York Times*, The Doctor's World, Mar. 26, 1991).

The inflammatory response in asthma is typical for tissues covered by a mucosa and is characterized by vasodilation, plasma exudation, recruitment of inflammatory cells such as neutrophils, monocytes, macrophages, lymphocytes and eosinophils to the sites of inflammation, and release of inflammatory mediators by resident tissue cells (e.g., mast cells) or by migrating inflammatory cells. In allergen-induced asthma, sufferers often exhibit a dual response to exposure to an allergen—an "early phase" response beginning immediately after exposure and lasting until 1-2 hours after exposure, followed by a "late phase" response beginning about 3 hours after exposure and lasting sometimes until 8-10 hours or longer after exposure. Late phase response in allergen-induced asthma and persistent hyperresponsiveness have been associated with the recruitment of leukocytes, and particularly eosinophils, to inflamed lung tissue.

The causes of asthma are not completely understood, however the study of agents that trigger acute asthmatic episodes supports the theory that asthma is an immunological reaction by a subject in response to specific allergens of the subject's environment (extrinsic asthma). These "triggers" exacerbate asthma by causing transient enhancement of airway hyperresponsiveness. Triggers that have been found to induce airway hyperresponsiveness include but are not limited to, inhaled allergens, inhaled low molecular weight agents to which the subject has become sensitized (such as by previous exposure), viral or mycoplasma respiratory infections. The common feature of inducing triggers is that they are associated with airway inflammation (see, Cockcroft, in *Asthma as an Inflammatory Disease*, O'Byrne (ed.), Marcel Dekker, Inc.; New York, 1990, pp. 103-125).

Without being bound by theory, it is believed that, following exposure to a trigger, such as an allergin, antigen presenting cells (APCs), T cells, B cells, eosinophils, mast cells, and basophils, contribute to the mechanism of asthma. Specifically, the APCs present antigen to T cells which, in turn, provoke B cells to produce IgE. B cells are stimulated to produce IgE by two types of signals, IL-4 or IL-13, and direct contact from T cells (Barnes and Lemanske, *New Engl. J. Med.*, 344:350-362, 2002). The released IgE activates mast cells which, in turn, cause constriction of the airways.

In order to treat or prevent an IgE-mediated disorder, such as asthma or rhino-conjunctivitis, a therapeutically effective amount of an antagonist of TSLP is administered to the subject. Generally, this administration results in the amelioration of a sign or a symptom of the disorder.

In one embodiment an additional anti-infective agent, anti-inflammatory agent, bronchodilator, enzyme, expectorant, leukotriene antagonist, leukotriene formation inhibitor, or mast cell stabilizer is administered in conjunction with a TSLP antagonist. The administration of the additional agent and the TSLP antagonist can be sequential or simultaneous.

TSLP antagonists include small molecule antagonists, antibodies to TSLP, antibodies to the TSLP receptor, and TSLP receptor fusion proteins, such as TSLPR-immunoglobulin Fc molecules or polypeptides that encode components of more than one receptor chain, that thereby mimic a physiological receptor heterodimer or higher order oligomer, amongst others. TSLP has been shown to bind directly to a type I cytokine receptor superfamily member (which are also known as hematopoietin receptor superfamily members), TSLPR. TSLPR has been cloned. The functional high-affinity receptor for TSLP has been demonstrated to include two polypeptides, TSLPR and the IL-7 receptor alpha chain. Thus, both TSLP and IL-7 shares IL-7Ralpha as a component of their receptors. However, these receptors are distinctive in that the TSLP receptor additionally contains TSLPR whereas the IL-7 receptor additionally contains the common cytokine receptor gamma chain, which is a signal-transducing component of various cytokine receptors. TSLPR (and Fc fusions of this receptor chain) are described, for example, in Published U.S. Patent Application No. 2002/0160949, which is incorporated herein by reference.

Interference with the ligand-receptor interaction has proven to be an effective strategy for the development of antagonists. In one embodiment, a ligand mutein of TSLP is utilized which retains receptor binding activity, but fails to induce receptor signaling. In one example, the mutein is a TSLP polypeptide that binds the receptor but does not trigger signaling through the receptor. Alternatively, the antagonist can be a small molecule which interferes with the binding of TSLP to its receptor. Small molecule libraries may be screened for compounds which may block the interaction or signaling mediated by an identified ligand-receptor pairing.

In another embodiment, a TSLP antagonist is an antibody that specifically binds to a specified cytokine ligand, such as TSLP (for example, primate, human, cat, dog, rat or mouse TSLP). In another embodiment, a TSLP antagonist is an antibody that binds the TSLP receptor.

A number of immunogens may be selected to produce antibodies specifically reactive with ligand or receptor proteins. Recombinant protein, such as a recombinant TSLP polypeptide or a TSLP receptor polypeptide can be used for the production of monoclonal or polyclonal antibodies. Naturally occurring protein, can also be used either in pure or partially purified form. Synthetic peptides, made using the appropriate protein sequences, can also be used as an immunogen for the production of antibodies. Recombinant protein can be expressed and purified in eukaryotic or prokaryotic cells (see Coligan, et al. (eds.), *Current Protocols in Protein Science*, John Wiley and Sons, New York, N.Y., 1995; and Ausubel, et al., *Current Protocols in Molecular Biology*, Greene/Wiley, New York, N.Y., 1987). Naturally folded or denatured material can be used, as appropriate, for producing antibodies. Either monoclonal or polyclonal antibodies may be generated.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed if desired. Immunization can also be performed through other methods, e.g., DNA vector immunization (see, for example, Wang, et al. *Virology* 228:278-284, 1997).

Monoclonal antibodies can be obtained by various techniques familiar to researchers skilled in the art. Typically, spleen cells from an animal immunized with a desired antigen are immortalized, commonly by fusion with a myeloma cell (for example, see, Kohler and Milstein, *Eur. J. Immunol.* 6:511-519, 1976). Alternative methods of immortalization include transformation with Epstein Barr Virus, oncogenes, or retroviruses, or other methods known in the art (for example see Doyle, et al. (eds.) *Cell and Tissue Culture: Laboratory Procedures*, John Wiley and Sons, New York, N.Y., 1994). Colonies arising from single immortalized cells are screened for production of antibodies of the desired specificity and affinity for the antigen, such as a TSLP polypeptide or the TSLP receptor. Yield of the monoclonal antibodies produced by such cells may be enhanced by various techniques, including injection into the peritoneal cavity of a vertebrate host. Alternatively, DNA sequences which encode a monoclonal antibody or a binding fragment thereof can be isolated by screening a DNA library from human B cells.

Antibodies include intact molecules as well as fragments thereof, such as Fab, F(ab')$_2$, and Fv which include a heavy chain and light chain variable region and are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

In one example, the variable region is an Fv, which includes the variable region of the light chain and the variable region of the heavy chain expressed as individual polypeptides. Fv antibodies are typically about 25 kDa and contain a complete antigen-binding site with 3 CDRs per each heavy chain and each light chain. The $V_H$ and the $V_L$ can be expressed from two individual nucleic acid constructs. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

One of skill in the art will realize that conservative variants of the antibodies can be produced. Such conservative variants employed in dsFv fragments or in scFv fragments will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. U.S.A.* 69:2659, 1972). Alternatively, the variable chains can be linked by an intermolecular disulfide bond or cross-linked by chemicals such as glutaraldehyde. See, e.g., Sandhu, supra. Thus, a dsFv can be produced. In an additional example, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, 2:97, 1991; Bird et al., *Science* 242:423, 1988; U.S. Pat. No. 4,946,778; Pack et al., *Bio/Technology* 11:1271, 1993; and Sandhu, supra).

Humanized monoclonal antibodies are produced by transferring donor antibody complementarity determining regions from heavy and light variable chains of the mouse immunoglobulin into a human variable domain, and then substituting human residues in the framework regions of the donor counterparts. The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993.

Antibodies to TSLP polypeptides are known in the art. In addition, anti-TSLPR antibodies are commercially available (R & D Systems, Minneapolis, Minn., cat. no. MAB981; DNAX Research, Inc., Palo Alto, Calif.). Antibodies are also prepared against TSLP receptor or TSLP by immunization with specified epitopes, such as regions of increased antigenicity determined by the Welling plot of Vector NTI.RTM. Suite (Informax, Inc, Bethesda, Md.). The sequence of the TSLP receptor, and regions of increased antigenicity in human TSLP receptor are disclosed in U.S. Patent Publication No. 2003/0186875. Pharmaceutical compositions (see above) generally include a therapeutically effective amount of a TSLP antagonist, and can also include additional agents. The preparation of pharmaceutical compositions is disclosed above.

An effective amount of a TSLP antagonist can be administered in a single dose, or in multiple doses, for example daily, during a course of treatment. In one embodiment, a therapeutically effective amount of a TSLP antagonist is administered as a single pulse dose, as a bolus dose, or as pulse doses administered over time. Thus, in pulse doses, a bolus administration of a TSLP antagonist is provided, followed by a time period wherein no TSLP antagonist is administered to the subject, followed by a second bolus administration. In specific, non-limiting examples, pulse doses of a TSLP antagonist are administered during the course of a day, during the course of a week, or during the course of a month.

Thus, the TSLP antagonist disclosed herein may be administered to a subject for the treatment of an inflammatory disorder. The TSLP antagonist can be administered to subject to treat an IgE-mediated disorder in a subject, such as asthma, in that individual. TSLP antagonist administration can be systemic or local. Local administration of the TSLP antagonist is performed by methods well known to those skilled in the art. By way of example, one method of administration to the lungs of an individual is by inhalation through the use of a nebulizer or inhaler. For example, the TSLP antagonist is formulated in an aerosol or particulate and drawn into the lungs using a standard nebulizer well known to those skilled in the art.

In other embodiments, the administration of the TSLP antagonist is systemic. Oral, intravenous, intraarterial, subcutaneous, intraperitoneal, intramuscular, and even rectal administration is contemplated.

The effectiveness of treatment with a TSLP antagonist can be measured by monitoring sign or symptoms of the IgE mediated disorder. For monitoring asthma, pulmonary function can be assessed by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. A statistically significant increase, as determined by mathematical formulas well known to those skilled in the art, in one or more of these parameters indicates efficacy of the TSLP antagonist treatment.

The methods of measuring pulmonary function most commonly employed in clinical practice involve timed measurement of inspiratory and expiratory maneuvers to measure specific parameters. For example, FVC measures the total volume in liters exhaled by a patient forcefully from a deep initial inspiration. This parameter, when evaluated in conjunction with the FEV1, allows bronchoconstriction to be quantitatively evaluated. A statistically significant increase, as determined by mathematical formulas well known to those skilled in the art, in FVC or FEV1 reflects a decrease in bronchoconstriction, and indicates that antagonist therapy is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, a statistically significant increase, as determined by mathematical formulas well known to those skilled in the art, in the FEF 25-75 or FEV1 reflects a decrease in bronchoconstriction, and indicates that TSLP antagonist therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air-flow rate in liters per minute during a forced maximal exhalation, is well correlated with overall pulmonary function in a patient with asthma and other respiratory diseases. Thus, a statistically significant increase, as determined by mathematical formulas well known to those skilled in the art, in the peak expiratory flow following administration of a TSLP antagonist indicates that the therapy is effective.

Production of a Knock-Out Mouse

A transgenic mouse is disclosed herein whose somatic and germ cells comprise a disrupted TSLP receptor gene, the disruption being sufficient to inhibit the binding of TSLP to a TSLP receptor (TSLP$^{-/-}$). Mice that are TSLP$^{-/-}$ exhibit a diminished inflammatory response in the lungs in response to an antigen. Transgenic mice are also disclosed herein that include a disrupted TSLP receptor gene, and a disrupted $\gamma_C$ gene, the disruption being sufficient to inhibit the production of a receptor including $\gamma_C$ or to disrupt the signaling of IL-7 through the IL-7 receptor. Mice that are TSLP receptor (R)$^{-/-}$ $\gamma^{-/-}$, or that are TSLP$^{-/-}\gamma_C^{-/-}$, that have a decreased T cell activity are also encompassed by this disclosure. One of skill in the art, using the description provided herein, can readily produce these animals.

A DNA molecule containing a desired gene sequence, such as a $\gamma_C$ or a TSLP receptor gene sequence, can be introduced into pluripotent cells (such as ES cells) by any method that will permit the introduced molecule to undergo recombination at its regions of homology. Techniques that can be used include calcium phosphate/DNA co-precipitates, microinjection of DNA into the nucleus, electroporation, bacterial protoplast fusion with intact cells, transfection, polycations, e.g., polybrene, polyornithine, etc. The DNA can be single or double stranded DNA, linear or circular. Techniques for transforming mammalian cells are known, and examples for such methods are described, for instance, in Keown et al., *Meth. Enzym.* 185:527-537, 1990 and Mansour et al., *Nature* 336:348-352, 1988.

Some methods, such as direct microinjection, or calcium phosphate transformation, may cause the introduced nucleic acid molecule to form concatemers upon integration. These concatemers can resolve themselves to form non-concatemeric integration structures. An alternative method for introducing the gene to the pluripotent cell is electroporation (Toneguzzo, et al., *Nucleic Acids Res.* 16:5515-5532, 1988; Quillet et al., *J. Immunol.* 141:17-20, 1988; Machy et al., *Proc. Natl. Acad. Sci. USA* 85:8027-8031, 1988).

After introduction of the DNA molecule(s), the cells are usually cultured under conventional conditions, as are known in the art. A selectable marker (as discussed above) can be used to facilitate the recovery of those cells that have received the DNA molecule containing the desired gene sequence. For the purposes of the present disclosure, any gene sequence whose presence in a cell permits recognition and clonal isolation of the cell can be employed as a detectable marker, whether or not it conveys a survival advantage in the transgenic cell.

After selection for cells that have incorporated the desired DNA molecule, the cells are cultured, and the presence of the introduced DNA molecule is confirmed as described above. For instance, approximately $10^7$ cells are cultured and screened for cells that have undergone a second recombinational event (discussed below), resulting in the replacement of a native sequence (i.e. a gene sequence that is normally and naturally present in the recipient cell) with the desired gene sequence. Any of a variety of methods can be used to identify cells that have undergone the second recombinational event, including direct screening of clones, use of PCR, use of hybridization probes, etc.

In one embodiment, a gene is located upstream or downstream from the targeting construct that provides for identification of whether a double crossover (and therefore targeted integration, not random integration) has occurred. By way of example, the herpes simplex virus thymidine kinase (HSV-tk) gene can be employed for this purpose, since the presence of the thymidine kinase gene is detected by the use of nucleoside analogs, such as acyclovir or gangcyclovir, for their cytotoxic effects on cells that contain a functional HSV-tk gene. The absence of sensitivity to these nucleoside analogs indicates the absence of the thymidine kinase and indicates that, therefore, where homologous recombination has occurred, a double crossover event has also occurred.

Once the DNA molecule containing the construct has been introduced into the ES cells (or other pluripotent cells), the construct recombines with the wild-type TSLP receptor or the $\gamma_C$ gene through the process of homologous recombination. Homologous recombination provides a method for introducing a desired gene sequence into a plant or animal cell and producing chimeric or transgenic plants and animals having defined, and specific, gene alterations. A discussion of the process of homologous recombination can be found in Watson, J. D., In: *Molecular Biology of the Gene,* 3rd Ed., W. A. Benjamin, Inc., Menlo Park, Calif., 1977.

In brief, homologous recombination is a well-studied natural cellular process that results in the scission of two nucleic acid molecules having identical or substantially similar sequences (i.e. "homologous"), and the ligation of the two molecules such that one region of each molecule initially present is now ligated to a region of the other initially present molecule (Sedivy, *Bio-Technol.* 6:1192-1196, 1988). Homologous recombination is a sequence-specific process by which cells can transfer a "region" of DNA from one DNA molecule to another. As used herein, a "region" of DNA is intended to generally refer to any nucleic acid molecule. The region can be of any length from a single base to a substantial fragment of a chromosome, and can, but needs not, include coding regions for one or more proteins.

For homologous recombination to occur between two DNA molecules, the molecules can possess a "region of homology" with respect to one another. Such a region of homology is usually at least two base pairs long, but is more customarily 2-20 Kb long. Two DNA molecules possess such a "region of homology" when one contains a region whose sequence is so similar to a region in the second molecule that base pairing and homologous recombination can occur. Recombination is usually catalyzed by enzymes that are naturally present in both prokaryotic and eukaryotic cells.

The transfer of a region of DNA can be envisioned as occurring through a multi-step process. If either of the two participant nucleic acid molecules is circular, then a recombination event results in the integration of the circular molecule into the other participant nucleic acid molecule. Importantly, if a particular region is flanked on both sides by regions of homology (which can be the same, but can also be different), then two recombinational events can occur, thus resulting in the exchange of a region of DNA between two DNA molecules. Recombination can be "reciprocal," and thus result in an exchange of DNA regions between two recombining DNA molecules. Alternatively, it can be "nonreciprocal" (also referred to as "gene conversion") and result in both recombining nucleic acid molecules having the same nucleotide sequence.

For homologous recombination, constructs are prepared where the gene of interest is flanked on one or both sides with DNA homologous with the DNA of the target region. The homologous DNA is generally within 100 Kb, but can be within 50 Kb, 25 Kb, or, in some embodiments, about 2.5 Kb or 1.5 Kb or more of the target gene. The homologous DNA can include the 5'-upstream region comprising any enhancer sequences, transcriptional initiation sequences, the region 5' of these sequences, or the like. The homologous region can include a portion of the coding region, where the coding region of a gene can include an open reading frame or combination of exons and introns. The homologous region can comprise all or a portion of an intron, where all or a portion of one or more exons also can be present.

Alternatively, the homologous region can comprise the 3'-region, so as to comprise all or a portion of the transcription termination region of a gene, or the region 3' thereof. The homologous regions can extend over all or a portion of a target gene, or be outside the target gene but include all or a portion of the transcriptional regulatory regions of the structural gene. In many embodiments, the homologous sequence will be joined to the gene of interest, proximally or distally. Usually, a sequence other than the wild-type sequence normally associated with the target gene will be used to separate the homologous sequence from the gene of interest on at least one side of the gene of interest. Some portion of the sequence can be the 5' or 3' sequence associated with the gene of interest (the target).

In order to prepare the subject recombining constructs, it is necessary to know the sequence that is targeted for homologous recombination. While a sequence of 14 bases complementary to a sequence in a genome can provide for homologous recombination, normally the individual flanking sequences will be at least about 150 bp, and can be 12 Kb or more, but usually not more than about 8 Kb. The sizes of the flanking regions are determined by the size of the known sequence, the number of sequences in the genome which can have homology to the site for integration, whether mutagenesis is involved and the extent of separation of the regions for mutagenesis, the particular site for integration, or the like. Suitable methods for homologous recombination are described, for example, in PCT Publication No. WO 02/14495 A2.

In one embodiment, a targeting vector is utilized for functionally disrupting an endogenous $\gamma_C$ or TSLP receptor gene in a cell includes:
 a) a nonhomologous replacement portion;
 b) a first homology region located upstream of the nonhomologous replacement portion, the first homology region having a nucleotide sequence with substantial identity to a first $\gamma_C$ or TSLP receptor gene sequence; and
 c) a second homology region located downstream of the nonhomologous replacement portion, the second homology region having a nucleotide sequence with substantial identity to a second $\gamma_C$ or TSLP receptor gene sequence, the second $\gamma_C$ or TSLP receptor gene sequence having a location downstream of the first $\gamma_C$ or TSLP receptor gene sequence in a naturally occurring endogenous $\gamma_C$ or TSLP receptor gene.

Thus, the nonhomologous replacement portion is flanked 5' and 3' by nucleotide sequences with substantial identity to a $\gamma_C$ or a TSLP receptor gene sequences. A nucleotide sequence with "substantial identity" to a $\gamma_C$ or a TSLP receptor gene sequence is intended to describe a nucleotide sequence having sufficient homology to a $\gamma_C$ or a TSLP receptor gene sequence to allow for homologous recombination between the nucleotide sequence and an endogenous $\gamma_C$ or TSLP receptor gene sequence in a host cell. Typically, the nucleotide sequences of the flanking homology regions are at least 90%, more preferably at least 95%, even more preferably at least 98% and most preferably 100% identical to the nucleotide sequences of the endogenous $\gamma_C$ or TSLP receptor gene to be targeted for homologous recombination. In one embodiment, the flanking homology regions are isogenic with the targeted endogenous allele (e.g., the DNA of the flanking regions is isolated from cells of the same genetic background as the cell into which the targeting construct is to be introduced). Additionally, the flanking homology regions of the targeting vector are of sufficient length for homologous recombination between the targeting vector and an endogenous $\gamma_C$ or a TSLP receptor gene in a host cell when the vector is introduced into the host cell. Typically, the flanking homology regions are at least 1 kilobase in length and more preferably are least several kilobases in length.

Chimeric or transgenic animals are prepared, for example, by introducing a TSLP receptor or a $\gamma_C$ construct, as described herein, into a precursor pluripotent cell, such as an ES cell, or equivalent, as described above, and in Robertson, E. J., in: *Current Communications in Molecular Biology*, Capecchi, M. R. (ed.), Cold Spring Harbor Press, Cold Spring Harbor, N.Y., 1989, pp. 39-44. The term "precursor" is intended to denote only that the pluripotent cell is a precursor to the desired ("transfected") pluripotent cell that is prepared in accordance with the teachings of the present disclosure. The pluripotent (precursor or transfected) cell can be cultured in vivo, in a manner known in the art (Evans et al., *Nature* 292:154-156, 1981) to form a chimeric or transgenic animal.

Any ES cell can be used in accordance with the present disclosure. For instance, in some embodiments, primary isolates of ES cells are used. Such isolates can be obtained directly from embryos such as the CCE cell line disclosed by Robertson, E. J., in: *Current Communications in Molecular Biology*, Capecchi, M. R. (ed.), Cold Spring Harbor Press, Cold Spring Harbor, N.Y., 1989, pp. 39-44), or from the clonal isolation of ES cells from the CCE cell line (Schwartzberg, et al., *Science* 246:799-803, 1989). Such clonal isolation can be accomplished according to the method of E. J. Robertson (in: *Teratocarcinomas and Embryonic Stem Cells: A Practical Approach* (E. J. Robertson, Ed.), IRL Press, Oxford, 1987). The purpose of such clonal propagation is to obtain ES cells that have a greater efficiency for differentiating into an animal. Examples of ES cell lines that have been clonally derived from embryos are the ES cell lines, AB1 (hprt+) or AB2.1 (hprt−).

The ES cells can be cultured on stromal cells (such as STO cells (especially SNC4 STO cells) and/or primary embryonic fibroblast cells) as described by E. J. Robertson (in: *Teratocarcinomas and Embryonic Stem Cells: A Practical Approach*, (E. J. Robertson, Ed.), IRL Press, Oxford, 1987, pp. 71-112). The stromal (and/or fibroblast) cells serve to eliminate the clonal overgrowth of abnormal ES cells. The cells can be cultured in the presence of leukocyte inhibitory factor ("lif") (Gough et al., *Reprod. Fertil. Dev.* 1:281-288, 1989; Yamamori et al., *Science* 246:1412-1416, 1989). Since the gene encoding lif has been cloned (Gough et al., *Reprod. Fertil. Dev.* 1:281-288, 1989), it is also possible to transform stromal cells with this gene, by methods known in the art, and to then culture the ES cells on transformed stromal cells that secrete lif into the culture medium.

ES cell lines can be derived or isolated from any species (for example, chicken, etc.), including cells derived or isolated from mammals such as rodents (i.e. mouse, rat, hamster, etc.), rabbits, sheep, goats, fish, pigs, cattle and primates such as humans. In one embodiment, the mammal is a mouse.

Transformed ES cells thereafter can be injected into blastocysts. Blastocysts containing the targeted ES cells are implanted into pseudo-pregnant females and allowed to develop to term. The ES cells thereafter colonize the embryo and can contribute to the germ line of the resulting chimeric animal (Jaenisch, *Science* 240:1468-1474, 1988). Chimeric offspring are identified, for instance, by coat-color markers, and those showing chimerism are selected for breeding offspring. Those offspring that carry the mutant allele can be identified by coat color or other markers, and the presence of the mutant allele reaffirmed by DNA analysis of blood samples.

A "double knock-out" can be generated by introducing two constructs into a single ES cell, one designed to undergo homologous recombination with the endogenous (wild-type) $\gamma_C$ gene (or another gene of interest, such as Rag2), and one designed to undergo homologous recombination with the endogenous (wild-type) TSLP receptor gene. Alternatively, one line of mice can be generated that are homozygous for a $\gamma_C$ gene deletion (knock-out), or for the deletion of another gene of interest (for example, Rag2, see below). An additional line of mice can be generated that are homozygous for a TSLP receptor gene deletion (knock-out). These two lines of mice can then be mated to produce mice that have both the other gene of interest (such as $\gamma_C$ or Rag2) and the TSLP receptor genes deleted.

In another embodiment, a line of mice can be generated that are homozygous for a $\gamma_C$ gene deletion. These animals are mated, and blastocysts are collected. Embryonic stem cells are then prepared from the $\gamma_C^{-/-}$ mice, and a construct is introduced into these cells designed to undergo homologous recombination with the TSLP receptor gene. Resultant offspring are mated, and $\gamma_C^{-/-}$TSLP receptor (R)$^{-/-}$ mice are selected. In another embodiment, a line of mice can be generated that are homozygous for a TSLP receptor gene deletion. These animals are mated, and blastocysts are collected from the TSLPR$^{-/-}$ mice. Embryonic stem cells are then prepared from the TSLPR$^{-/-}$ mice, and a construct is introduced into these cells designed to undergo homologous recombination with the $\gamma_C$ gene. Similar methods could be used to produce other double knock-out mice homozygous for a TSLP receptor deletion, and for a deletion of another gene of interest, such as, but not limited to, Rag-2.

In addition to using homologous recombination in ES cells to produce gene knock-outs, a recombining site/recombinase system can be used to generate knock-outs gene (Rajewsky, *J. Clin. Invest.* 98:600-603, 1996). The Cre enzyme is a member of a large family of recombinases that recognizes specifically recombining sites (e.g. loxP, a sequence motif of 34 base pairs) and can induce recombination at these sites. If a DNA segment is flanked by two loxP sites in the same orientation, Cre excises that segment from the DNA, leaving a single LoxP behind. By appropriately positioning the two loxP sites, this system can be used to generate deletions, such as a deletion in a TSLP receptor, TSLP or $\gamma_C$ gene.

Thus, in one embodiment, a transgenic mouse is produced that includes a loxP flanked (floxed) gene, such as a TSLP receptor, TSLP or $\gamma_C$ gene. Mice are also produced that include a promoter, such as a tissue specific (e.g. an immunoglobulin promoter) or an inducible promoter (e.g. a temperature sensitive promoter), operably linked to Cre gene in their genome. Mice including the floxed gene are then mated to the mice including the Cre gene. Under appropriate conditions, the expression of Cre is induced, and recombination occurs at the recombining sites, resulting in deletion of the floxed gene, such as the TSLP, TSLP receptor or $\gamma_C$ gene.

In one embodiment, $\gamma_C^{-/-}$TSLPR$^{-/-}$ mice exhibit decreased cellularity of the thymus. In one embodiment, the cellularity of the thymus is decreased at least about 40%, 50%, 60%, 70%, 80%, 90%, 95%, or 99% as compared to a control. In one embodiment, a control is a $\gamma_C^{+/+}$TSLPR$^{+/+}$ (wild-type) animal. In another embodiment, a control is a standard value. In another embodiment, $\gamma_C^{-/-}$TSLPR$^{-/-}$ mice exhibit decreased numbers of CD4$^+$ T cells. Thus, the number of CD4$^+$ T cells is decreased by at least about 50%, such as at least about 60%, 70%, 80%, 90%, 95%, or 99%, as compared to a control.

In an additional embodiment, TSLPR$^{-/-}$ mice exhibit decreased response to an antigen, such as an antigen known to induce an inflammatory response, and/or induce the production of IgE. For example, TSLPR$^{-/-}$ mice exhibit a decreased inflammatory response following administration of ovalbumin (OVA).

In one embodiment, $\gamma_C^{-/-}$TSLPR$^{-/-}$ mice are used to test agents designed to affect T cell proliferation. Thus, an agent is administered to $\gamma_C^{-/-}$TSLPR$^{-/-}$ mice, and its effect on the number of CD4$^+$ T cells and/or the cellularity of the thymus is assessed. In one example, the agent increases T cell proliferation.

Thus, a transgenic mouse is disclosed whose somatic and germ cells comprise a disrupted thymic stromal lymphopoietin receptor (TSLP) gene (the disruption being sufficient to inhibit the interaction of TSLP with its receptor). These mice show a decreased response to the administration of an inflammatory antigen, such as an antigen known to induce asthma. A transgenic mouse is disclosed whose somatic and germ cells comprise a disrupted thymic stromal lymphopoietin receptor (TSLP) gene (the disruption being sufficient to inhibit the interaction of TSLP with its receptor) and a disrupted $\gamma_c$ gene (the disruption being sufficient to reduce signaling through the $\gamma_c$). The disrupted IL-21 receptor and disrupted $\gamma_c$ genes are introduced into the mouse or an ancestor of the mouse at an embryonic stage. A mouse homozygous for the disrupted TSLP receptor gene and homozygous for the disrupted $\gamma_c$ gene has diminished thymic cellularity. A transgenic mouse is also disclosed whose genome is heterozygous for an engineered disruption in a TSLP receptor gene and whose genome is heterozygous for an engineered disruption in an $\gamma_c$ gene. The engineered TSLP receptor gene and the engineered $\gamma_c$ gene in a homozygous state inhibits production of a functional TSLP receptor and a functional $\gamma_c$, such that the transgenic mouse has reduced cellularity of the thymus as compared to a wild-type mouse.

The disclosure is illustrated by the following non-limiting Examples.

EXAMPLES

Example 1

Materials and Methods

Generation of TSLPR$^{-/-}$ mice: TSLPR genomic DNA was obtained from a P1 clone prepared from 129sv mice (Genome Research). The targeting construct was designed to delete all exons of the TSLPR gene and replace them with the neomycin resistance gene (Neo). The targeting construct had 6 kb (Bgl II to Nhe I) and 3 kb (Pvu II) 5' and 3' flanking regions, respectively, of the Neo gene. Embryonic stem (ES) cells were electroporated with 50 µg of linearized targeting construct. Positive and negative selection of transfected cells was conducted using G418 (350 µg/ml; Life Technology, Carlsbad, Calif.) and gancyclovir (2 µM; Sigma, St. Louis, Mo.), respectively. Of 800 ES clones screened, those that had undergone homologous recombination were identified by Southern blotting, using probes located 5' and 3' to the targeting construct. Mice were mated once with wild-type C57BL/6. The mice were genotyped using three PCR primers:

TABLE 2

| Genotyping Sequences | | |
|---|---|---|
| Name | Sequence | Identifier |
| A | 5'-AACCTCTCCCACAAGAAGTCCAGAAGT-3' | SEQ ID NO: 6 |
| Neo (N) | 5'-ATCGCCTTCTATCGCCTTCTT-3' | SEQ ID NO: 7 |
| B | 5'-AGACTTTACCTGATTCCTGCCTTG-3' | SEQ ID NO: 8 |

Primers A and B amplify a 250 bp segment of the TSLPR gene. Primers N and B identify the targeted gene and give a 650 bp product. The probes for Southern blots were generated using Taq Gold kit (Applied Biosystems, Foster City, Calif.) under the following conditions: 94° C. for 2 minutes, 25 cycles of 94° C. for 30 seconds, 58° C. for 45 seconds and 45° C. for 45 second, then 72° C. for 7 minutes prior to cooling to 4° C. Genotyping PCR reactions were performed under the same conditions but for 33 cycles instead of 25 and using "Ready to go PCR beads" (Amersham, Piscataway, N.J.). RT-PCR was used to determine TSLPR mRNA expression. RNA samples were extracted from thymi using Trizol (Promega, Madison, Wis.) following the manufacturer's directions and 1 µg of total RNA was used per reaction. Internal upstream (5'-GCGAGGGCGGGGCTGCTGGAG-3', SEQ ID NO: 9) and downstream (5'-CCTGGCTG-GCGGGGCTGTGGC-3', SEQ ID NO: 10) primers were amplified using RNA PCR kit (Applied Biosystems, Foster City, Calif.) according to manufacturer's instructions, and Southern blots were performed using genomic DNA digested as described above. Probes were labeled, hybridized, and washed using QuickHyb protocol (Stratagene, La Jolla, Calif.) according to the manufacturer's recommendations. TSLPR$^{-/-}$ mice generated from two different ES clones showed no apparent differences. Unless indicated otherwise, all mice analyzed were 6-8 weeks of age littermates and generally sex-matched. No sex related differences were observed between WT and TSLPR KO mice.

To generate TSLPR/$\gamma_c$ double KO mice, TSLPR KO females were mated to $\gamma_c$ KO males. As $\gamma_c$ is on the X-chromosome, TSLPR$^{+/-}\gamma_c^{+/-}$ female and TSLPR$^{+/-}\gamma_c^{-/Y}$ male F1 progeny were then mated. TSLPR/$\gamma_c$ double KO and $\gamma_c$ KO littermate progeny were then analyzed.

Cytokine injections: Two week old WT or $\gamma_c$ KO mice received daily intraperitoneal injections with 0.1 ml of PBS alone or containing murine IL-7 (0.5 µg) or murine TSLP (0.5 µg) for 1 and 3 weeks, so that mice were 3 and 5 weeks old at the time of the analysis.

Treatment with IL-7 neutralizing mAb: Eight to ten week old WT and TSLPR KO females were irradiated with 600 cGy of whole body irradiation. Mice were injected 3 times a week for 4 weeks with 1 mg of a control mAb or M25 anti-IL-7 neutralizing mAb (Bhatia et al., *J Exp Med* 181:1399-1409, 1995).

Flow cytometric analyses: Single cell suspensions were prepared from thymus, spleen and bone marrow. Cells were washed with FACS buffer (phosphate buffered saline pH 7.4, 0.5% bovine serum albumin (BSA), 0.02% sodium azide). One million cells were treated with Fc-block (PharMingen, San Diego, Calif.) for 15 minutes before being incubated with the indicated fluorochrome-conjugated antibodies (all from PharMingen) for 20 minutes. Cells were then washed twice with FACS buffer and analyzed.

Measurement of IgM levels: Sera from 3-week old $\gamma_c$ KO and TSLPR/$\gamma_c$ double KO mouse littermates were analyzed for resting IgM levels using a sandwich enzyme linked immunosorbent assay (ELISA). Briefly, 100 µl (2 µg/ml in coating buffer; 0.15 M sodium carbonate, 0.35 M sodium bicarbonate pH 9.5, 0.02% sodium azide) of anti-mouse IgM capture antibody (PharMingen) was used to coat 96 well-plate (EIA plates, Costar, Somerset, N.J.) overnight at 4° C. Wells were coated with blocking buffer (PBS supplemented with 10% fetal bovine serum [FBS]) for 1 hour at room temperature. Sera were diluted at 1:1000 in blocking buffer and incubated overnight at 4° C. Wells were washed in PBS containing 0.1% Tween and then incubated with a 1:2000 dilution of secondary HRP-conjugated anti-IgM (PharMingen) for 1 hour at RT. The assay was ended by adding the substrate mixture (PharMingen) and measuring absorbance at 450 nm.

Proliferation and survival assays: To isolate CD4$^+$ and CD8$^+$ single positive T cells, thymocytes were first treated with anti-CD8$^+$ or anti-CD4$^+$ paramagnetic beads, respectively, and the cells that bound these beads were removed by passing the samples through the autoMACS system (Miltenyi Biotec). The non-bound cells (negative eluted fraction) were then treated with CD4$^+$ and CD8$^+$ paramagnetic beads to separate CD4$^+$ and CD8$^+$ cells, respectively, from the double negative cells. Mature splenic CD4$^+$ and CD8$^+$ T cells were isolated using their respective paramagnetic beads. Fresh thymocytes and splenocytes were cultured for 48 hours in RPMI 1640 medium containing 10% FBS, 2 mM L-glutamine, and antibiotics, on 96 well flat-bottom plates (2×10$^5$ cells/well) that were not coated or coated with anti-CD3ε (2 µg/ml, PharMingen). Cells were additionally incubated with IL-7 (100 ng/ml) or TSLP (100 ng/ml) as indicated. Wells were pulsed with 1 µCi of [$^3$H] thymidine (6.7 Ci/mmol, NEN, Boston, Mass.) for the last 9 hours of culture. Proliferation was also examined using CFSE labeling (5 µM; Sigma, St. Louis, Mo.) for 10 minutes at 37° C. For in vivo proliferation, 0.8 mg of 5-Bromo-2'-deoxyuridine (BrdU) (Sigma-Aldrich, St. Louis, Mo.) was injected 16 and 10 hours before sacrifice. Levels of BrdU were determined using PE-conjugated antibodies (Tough et al., *J Exp Med* 179:1127-1135, 1994). To examine the survival of thymocytes, cells were also isolated and cultured as described above for 1 week and the number of live cells was determined by trypan blue exclusion.

Adoptive transfer of T cells: $\gamma_c$ KO mice were irradiated with 600 cGy of whole body irradiation. Eight hours later, the mice were injected with a single cell suspension of 8×10$^6$ cells splenic CD4$^+$ or CD8$^+$ T cells labeled with CFSE (10 minutes, 37° C.) that had been isolated using anti-CD4$^+$ or anti-CD8$^+$ paramagnetic beads (Miltenyi Biotec), respectively, from either WT or TSLPR KO mice. Recipient mice were analyzed on days 3 and 7 and host spleens were extracted and analyzed by flow cytometry.

Example 2

Generation of Mice Lacking TSLPR

In order to generate TSLPR KO mice, a targeting vector was used that was designed to replace the TSLP coding region with the neomycin resistance cassette (FIG. 1A). A total of 4 clones out of 800 showed homologous recombination as determined using both 3' and 5' probes (FIG. 1B). Two clones were microinjected into blastocysts to generate chimeric mice and heterozygous offspring corresponding to each clone were intercrossed to generate TSLPR$^{-/-}$ mice, as confirmed by PCR genotyping, and evaluation of TSLPR mRNA expression (FIG. 1C). Breeding of TSLPR$^{+/-}$ mice produced wild-type, heterozygous, and KO offspring in normal Mendelian ratios. TSLPR$^{-/-}$ mice were indistinguishable from wild-type littermates in growth, development, breeding, and viability. The inactivation of TSLP signaling was confirmed by the lack of a greater response of TSLPR KO splenocytes to treatment with anti-CD3+ TSLP than anti-CD3 alone, as opposed to the greater response seen in wild-type (WT) splenocytes when anti-CD3 and TSLP were combined (FIG. 1D).

Example 3

TSLPR KO Mice Exhibit Normal Lympho-hematopoietic Development

Thymus, spleen, and bone marrow were similar in size and cell number, and no differences in histology were observed in TSLPR KO mice versus their wild-type littermates. Analysis of TSLPR KO thymi showed that the double negative (DN), double positive (DP), and CD4$^+$ and CD8$^+$ single positive T cells were present at normal distributions (FIG. 1E). Furthermore, mature T cells in the spleen were also present at the expected ratios.

B220 versus anti-CD3 staining in the spleen was normal, as was the CD4:CD8 ratio T cell ratio (FIG. 1 F, upper panels). Moreover, levels of both B220$^+$ IgM$^+$ immature cells and B220$^+$IgM$^-$ pre-B and pro-B cells (both percent and absolute numbers) were similar in TSLPR KO and WT mice in both spleen (FIG. 1 F, lower panels) and bone marrow (FIG. 1 G). Surface levels of CD3, TCR β, TCR γδ, CD4, CD5, CD8, CD11c, CD21, CD23, CD43, CD44, CD62L, B220, IgM, IgD, DX5, Gr1, TER119, $\gamma_c$, HSA, and BP-1, as well as IL-7Rα, were comparable to those found in wild-type mice. Thus, although TSLP has been reported to affect fetal lymphoid development, no overt defects were found in adult lymphopoiesis in TSLPR KO mice. It is possible that TSLP serves a redundant role and that other cytokines, especially the closely related IL-7, could compensate for the absence of TSLP signal. No difference was observed between WT and TSLPR KO mice in the number of colony forming units (CFU-B and CFU-GM assays) from BM cultures in vitro. Although TSLPR is expressed in various tissues including brain, liver, and lung (Pandey et al., *Nat Immunol* 1:59-64, 2000), suggesting a possible role of TSLP in the physiological functions of these organs, histopathological analysis of these organs in TSLPR KO mice revealed no obvious abnormalities.

Example 4

TSLP and IL-7 Exhibit Overlapping Actions in vivo

Figure 9:
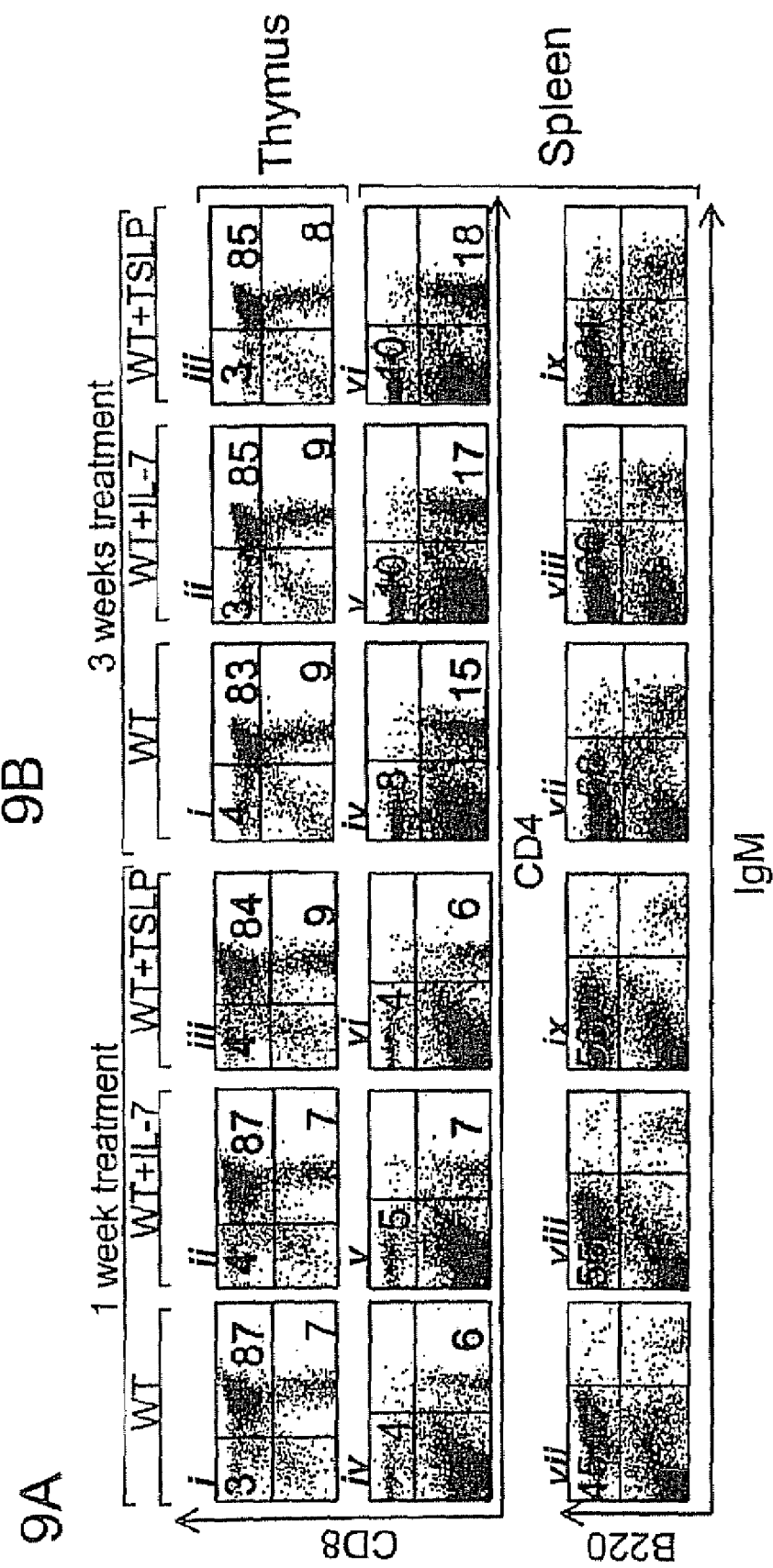
FIGS. 9A-9B are a set of plots showing the effect of TSLP on lymphopoiesis in WT mice. Flow cytometric analysis of thymus and spleen 1 (FIG. 9A) and 3 weeks (FIG. 9B) after injection of WT mice with PBS, IL-7, or TSLP.

Because TSLP and IL-7 share IL-7Rα as a receptor component, the actions of these cytokines was compared. Both IL-7 and TSLP similarly increased thymic and splenic cellularity in WT mice after one week of daily injections (FIG. 2A, left half of panel), with CD4 and CD8 T cell populations present in normal ratios (FIG. 9A, ii and iii versus i; v and vi versus iv); thus, thymic and splenic T cell populations were all increased. FIG. 9 shows the effect of TSLP on lymphopoiesis in WT mice. Shown are the flow cytometric analysis of thymus and spleen 1 and 3 weeks after injection of WT mice with PBS, IL-7, or TSLP. Thymocytes were stained with anti-CD4 versus anti-CD8; splenocytes were stained with anti-CD4 versus anti-CD8 and anti-B220 versus anti-IgM.

Figure 2:
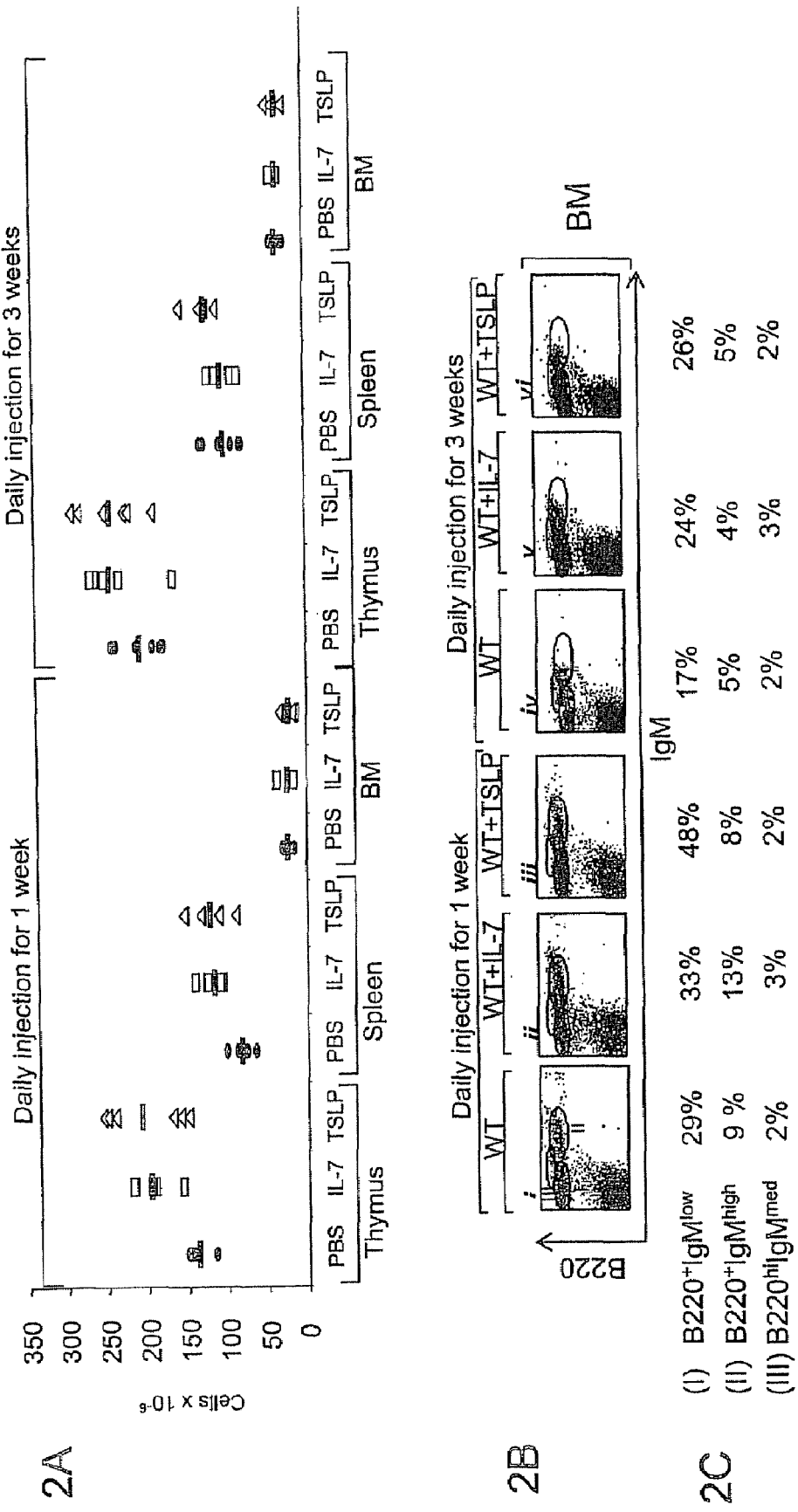
FIGS. 2A-2C are a graph, plot and a table showing that TSLP can expand lymphocyte populations in WT mice.

In the spleen, TSLP and IL-7 had similar abilities to increase B cells (FIG. 9A, viii and ix versus vii), while TSLP was more potent in expanding immature B220$^+$IgM$^{low}$ cells in the BM (FIG. 2B, ii and iii versus i; see percentages for the different fractions of B cells in FIG. 2C). After three weeks of treatment of wild-type mice with TSLP or IL-7, the increase in thymic and splenic cellularity was no longer statistically significant (FIG. 2A, right half of panel), and the CD4$^+$/CD8$^+$ T cell ratio remained constant (FIG. 9B, ii and iii versus i and v and vi versus iv), but the increase in B cells was still evident in the spleen (FIG. 9B, viii and ix versus vii) and BM (FIG. 2B, v and vi versus iv; see percentages for the different fractions of B cells in FIG. 2C). The consistent absolute decrease in B cells in WT animals between 1 and 3 weeks of treatment presumably at least in part reflects an age-dependent regulatory mechanism of B cell expansion, as a decrease was even seen in the untreated control animals (FIG. 2 C). These results indicate that both TSLP and IL-7 can promote lymphocyte expansion. The normal levels of lymphocytes in TSLPR KO mice presumably are likely in part or entirely explained by the continued action of IL-7.

Example 5

Figure 3:
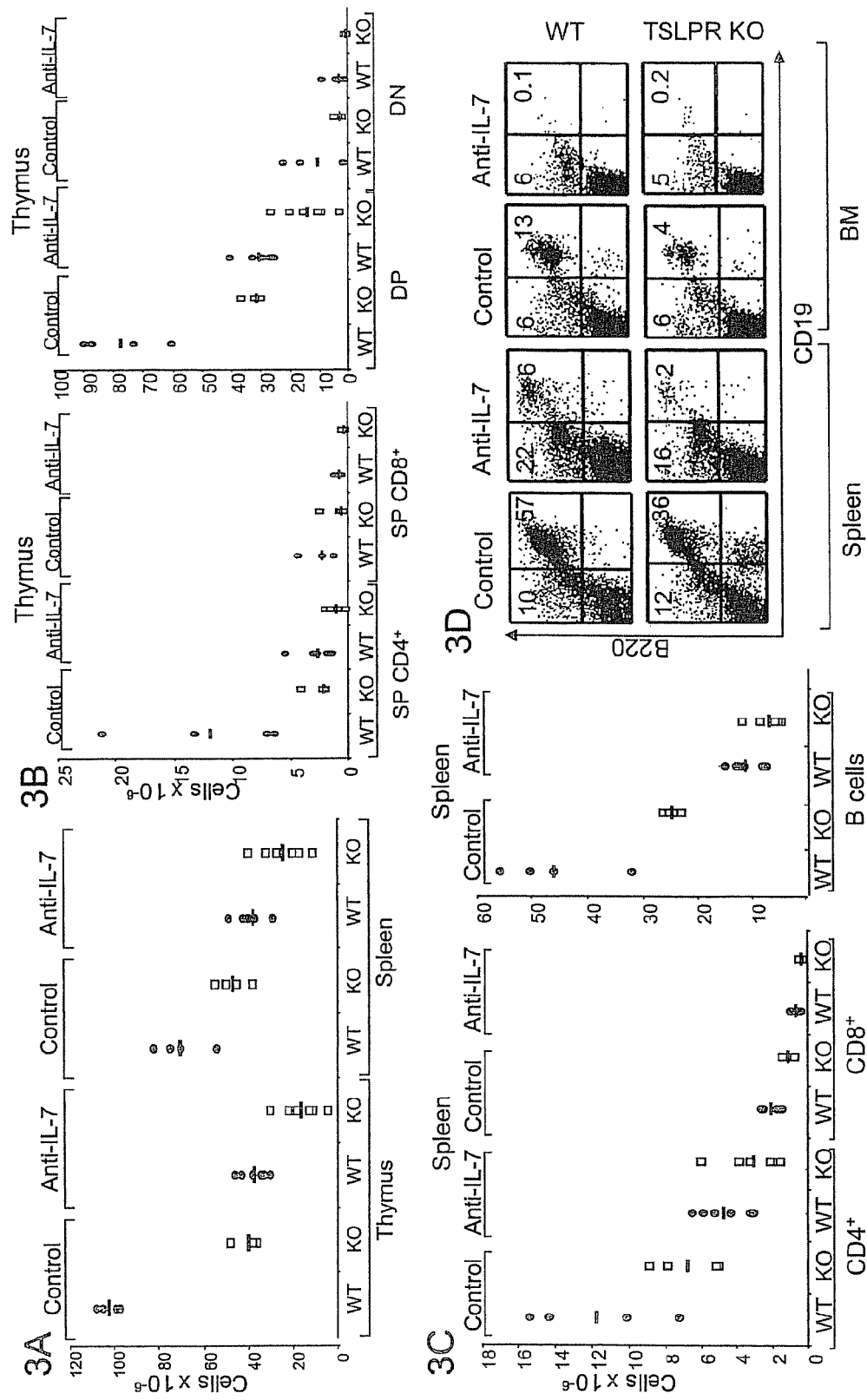
FIGS. 3A-3D are a set of graphs and plots showing that TSLP is critical for optimal lymphopoiesis in the presence and absence of IL-7. WT and TSLPR KO mice were sublethally irradiated and injected three times a week for four weeks with 1 mg of control or M25 anti-IL-7 mAbs.

TSLP Signaling is Required for Efficient Recovery of Lymphocyte Populations Following Sub-lethal Irradiation To further examine the role of TSLP in lymphopoiesis, WT and TSLPR KO mice were sub-lethally irradiated and their ability to recover cellular populations was evaluated. In these experiments, either a control mAb or neutralizing mAb to IL-7 was included. Irradiated WT animals treated with the control mAb recovered most of their thymic and splenic cellularites within 4 weeks, whereas TSLPR KO mice did not (FIG. 3 A). Similarly, CD4$^+$ and CD8$^+$ T cell sub-populations in the thymus (FIG. 3 B) and spleen (FIG. 3 C) were lower in TSLPR KO mice than in WT littermates. B cell recovery in TSLPR KO mice was also less efficient than in WT mice (FIG. 3C), and flow cytometric analysis of B cells showed that B220$^+$ CD19$^+$ B cells were greatly diminished in the spleens in TSLPR KO mice (FIG. 3D). These results establish a critical role for TSLP in mediating optimal T and B cell lymphopoiesis in mice.

Reconstitution was examined in mice in which a neutralizing mAb to IL-7 was injected (1 mg three times a week for 4 weeks) (Bhatia et al., *J Exp Med* 181:1399-1409, 1995). As expected, treatment with the anti-IL-7 mAb reduced lymphopoiesis in WT mice (FIG. 3A). Importantly, however, recovery was even more impaired in TSLPR KO mice treated with anti-IL-7 mAb, including impaired thymic and splenic cellularity (FIG. 3A), with CD4$^+$ and CD8$^+$ T cell sub-populations in the thymus (FIG. 3 B) and spleen (FIG. 3C) being lower in TSLPR KO mice than in WT littermates. No significant differences in the percentages of DN1, DN2, DN3, and DN4 cells were observed. B cell recovery in TSLPR KO mice was also less efficient than in WT mice in the presence of anti-IL-7 mAb (see bone marrow and spleen in FIGS. 3C and 3D). B220$^+$ CD19$^+$ B cells were nearly eliminated in the BM in both WT and TSLPR KO mice treated with anti-IL-7 (FIG. 3D, far right panels). These results establish a critical role for TSLP in mediating optimal T and B cell lymphopoiesis in mice. Because recovery is less in the absence of signaling by TSLP+IL-7 as compared to the absence of only IL-7, the data presented herein indicate a critical IL-7-independent role for TSLP in recovering from lymphopenia.

Example 6

Figure 4:
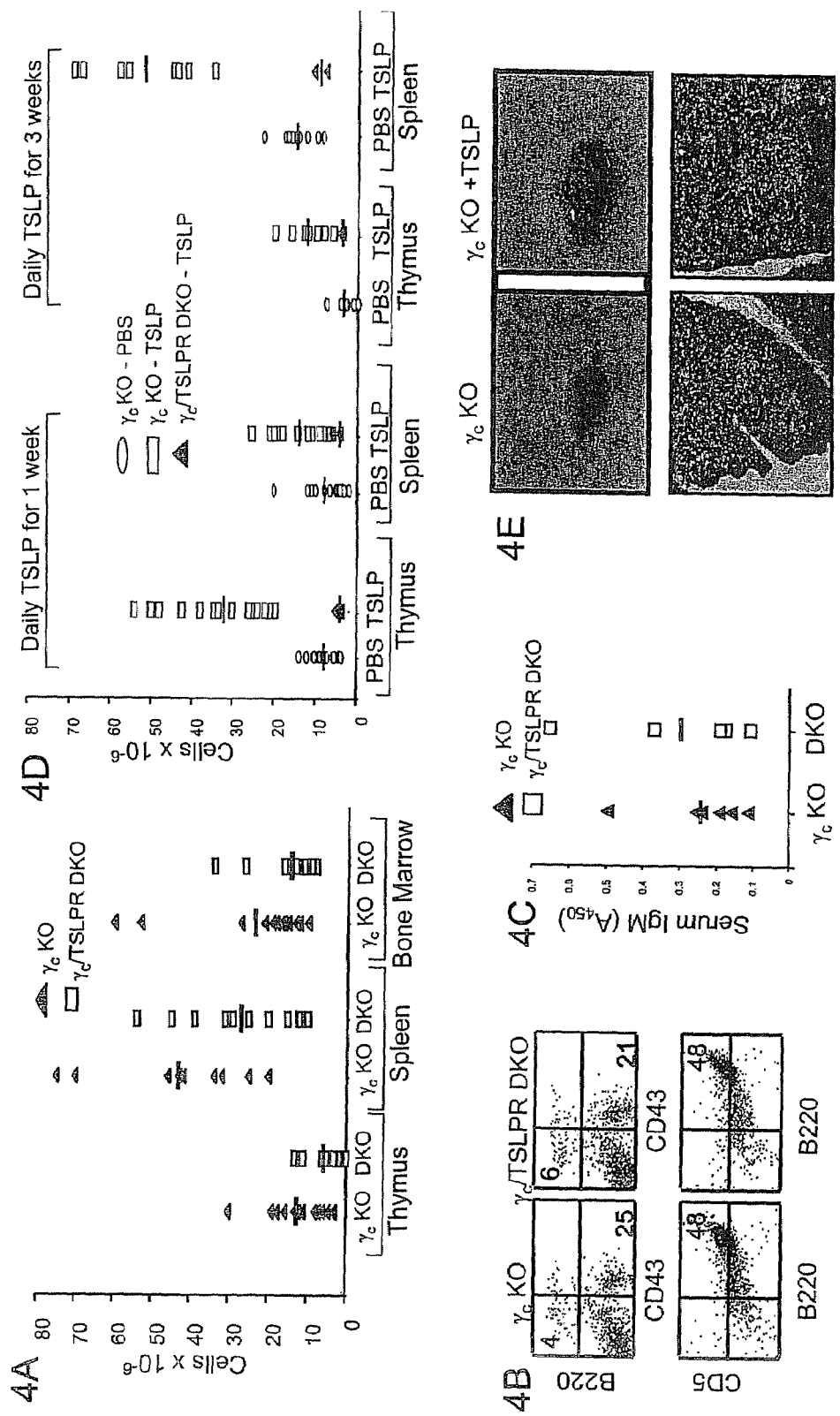
FIGS. 4A-4E are graphs, plots and digital images showing a comparison of the lymphoid development in $\gamma_c$ KO mice versus $\gamma_c$/TSLPR DKO mice.

TSLPR/$\gamma_c$ Double KO Mice Exhibit Greater Defects than Do $\gamma_c$ KO Mice $\gamma_c$ KO mice have defective T and B cell development. To further investigate a possible distinctive role of TSLP in lymphoid development, TSLPR KO mice were crossed to $\gamma_c$ KO mice to generate F2 progeny lacking both receptor chains (see Methods). $\gamma_c$ KO mice have defective T and B cell development. A greater defect in $\gamma_c$/TSLPR double KO mice than in $\gamma_c$ single KO mice would suggest a role for TSLP in contributing to the residual lymphoid development that is present in $\gamma_c$ deficient mice and in humans with XSCID. Indeed, the low thymic cellularity observed in $\gamma_c$ KO mice (DiSanto et al., *Proc Natl Acad Sci USA* 92:377-381, 1995; Cao et al., *Immunity* 2:223-238, 1995) was further diminished in double KO littermates (FIG. 4A). However, CD4$^+$ and CD8$^+$ single positive, CD4$^+$CD8$^+$ double positive (DP), and CD4$^-$CD8$^-$ double negative T cells (DN1, DN2, DN3 and DN4) were all present at ratios comparable to thymi of $\gamma_c$ deficient mice. Similarly, although total BM cellularity was greatly reduced, a similar distribution of B cell sub-populations was present in BM (FIG. 4B) and spleen as were seen in $\gamma_c$ KO mice. Specifically, B220 versus CD43 profiles were similar in both $\gamma_c$ KO and the $\gamma_c$/TSLPR double KO mice (FIG. 4B, upper panels), as was expression of HSA, BP1, and IgM (data not shown). Peritoneal CD5$^+$ B1 cells were also present in similar numbers in both $\gamma_c$ KO and the $\gamma_c$/TSLPR double KO mice (FIG. 4B, lower panels). Consistent with this, $\gamma_c$/TSLPR double KO mice did not have lower serum IgM levels than those found in $\gamma_c$ KO mice (FIG. 4C). Thus, TSLP does not appear to regulate numbers of B1 cells nor affect IgM production.

Example 7

TSLP Expands Both B and T Cells in $\gamma_c$ KO Mice

As an alternative approach to elucidate a possible role for TSLP in lymphoid physiology, the effect of TSLP on $\gamma_c$ KO mice was evaluated. There is a sharing of IL-7Rα by the receptors for both of these cytokines and the potential for overlapping actions between TSLP and IL-7. It was possible that these $\gamma_c$ KO mice that lack IL-7 signaling and have diminished thymocytes could exhibit hyper-responsiveness to TSLP. Two week old $\gamma_c$ KO mice received daily 0.5 µg i.p. injections of phosphate buffered saline (PBS) or TSLP for 1 or 3 weeks. Strikingly, after 1 week, TSLP treatment increased thymic cellularity 5-10 fold (p<0.01) (FIG. 4D, open rectangles versus ovals), consistent with increased thymic size (FIG. 4E, upper panels). Histological analysis showed that thymi from $\gamma_c$ KO mice injected with PBS had a thin cortex whereas the thymi of TSLP-injected mice had a wider corte (FIG. 4E. lower panels).

Figure 5:
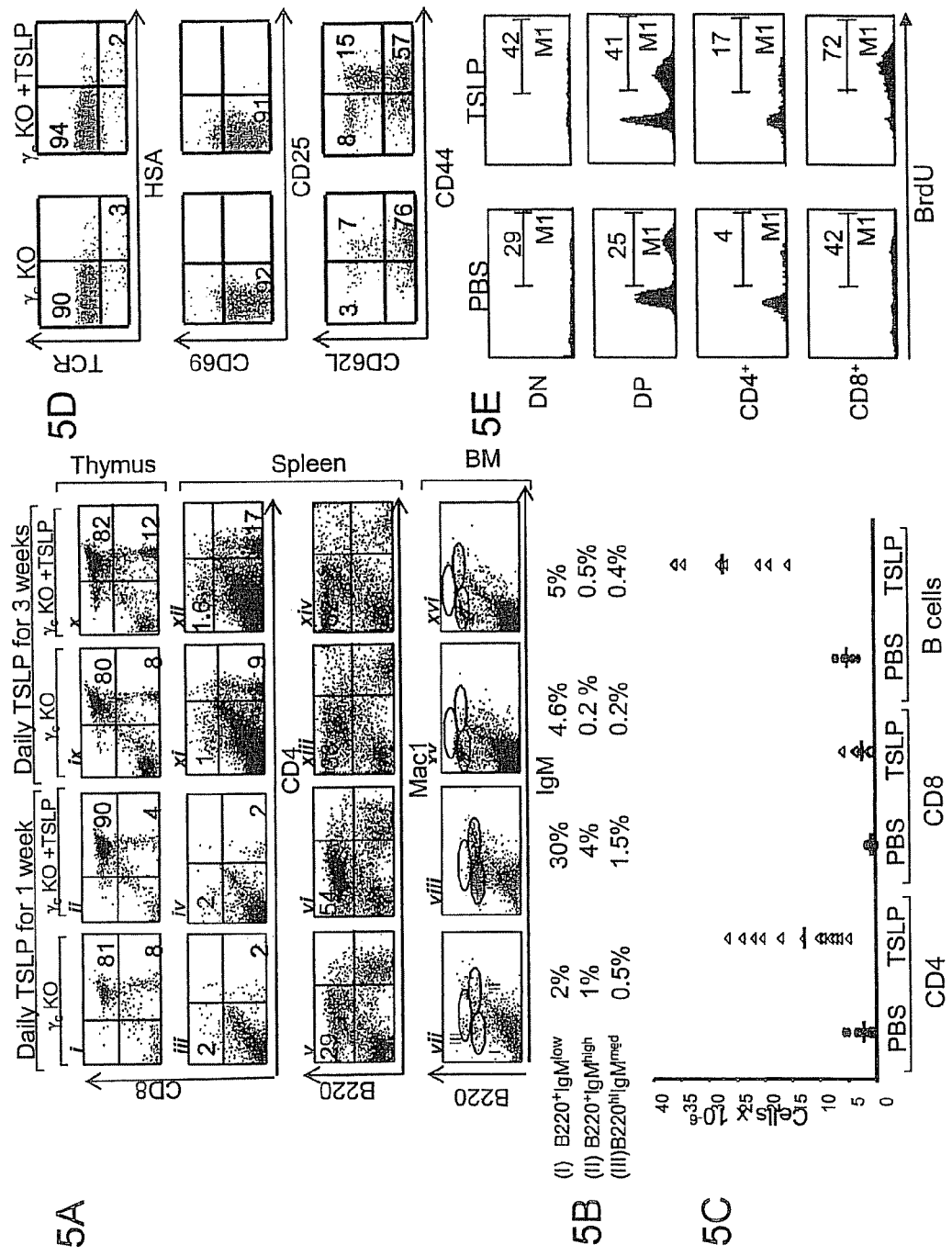
FIGS. 5A-5E are a set of images showing TSLP can increase lymphoid subpopulations in $\gamma_c$ deficient mice.

In addition to increased thymic cellularity, the fraction of DP cells increased so that this was the most expanded thymic population (FIG. 5A, ii versus i). $\gamma_c$ KO mice injected with TSLP for 3 weeks still showed higher total thymic cellularity than untreated mice (FIG. 4D, p<0.01) albeit less so than at 1 week, with more CD4$^+$ SP T cells present (FIG. 5A, x versus ix). TSLP treatment for one week also increased the total number of splenocytes (p<0.01) (FIG. 4D), mainly by increasing B cells (FIG. 5A, vi versus v). After three weeks of TSLP, splenic cellularity further increased (p<0.01) (FIG. 4D). As expected, this resulted in part from the expansion of B cells (FIG. 5A, xiv versus xiii). The increase in B cells in the spleen was also evident in the bone marrow. Although the total BM cellularity in $\gamma_c$ KO mice was not increased by TSLP, TSLP dramatically increased the B cell sub-populations within 1 week (FIG. 5A, viii versus vii), with immature B cells being the most affected, increasing from approximately 2% to 30% of the total number of cells (see % of B220$^+$ IgM$^{low}$ cells in FIG. 5B). More mature stages also increased three to four fold. However, these changes in B cell populations were transient, and at three weeks of TSLP injection these cells diminished to the BM B lymphocyte cellularity seen in the untreated mice (FIG. 5A, xvi versus xv and FIG. 5B).

In addition to the increased B cells noted above, the increased splenic cellularity was also partially due to an increase in CD4$^+$ T cells (FIG. 5A, xii versus xi and FIG. 5C). Consistent with the age-dependent increase in CD4$^+$ T cells that occurs in $\gamma_c$ KO mice (Cao et al., *Immunity* 2:223-238, 1995), control $\gamma_c$ KO mice that were injected with PBS for 3 weeks versus one week showed an age-dependent increase in the percentage of CD4$^+$ T cells (FIG. 5A, xi versus iii). Approximately 5.4 fold more CD4$^+$ splenic T cells were found in TSLP-treated $\gamma_c$ KO mice than in untreated mice (12.7×10$^6$ versus 2.4×10$^6$), whereas the absolute and relative increase in mature splenic CD8$^+$ T cell numbers was less marked in TSLP-treated versus control animals (3.8 fold, 2.4×10$^6$ versus 0.63×10$^6$) (FIG. 5C). Almost all of the CD4$^+$ T cells in $\gamma_c$ KO mice were TCR$^{high}$ HSA$^{low}$ and did not express the activation markers CD25 and CD69 and this was unaffected by TSLP treatment (FIG. 5D, upper and middle panels). CD4$^+$ T cells in $\gamma_c$ KO mice primarily have a CD62$^{low}$ CD44$^{high}$ memory phenotype (Nakajima et al., *J Exp Med* 185:189-195, 1997). Interestingly, TSLP most increased the number of CD62L$^{high}$ CD44$^{high}$ cells (FIG. 5D, lower panels), a population that has been identified as central memory cells (Sprent and Surh, *Curr Opin Immunol* 13:248-254, 2001).

Example 8

TSLP Induces Thymocyte Proliferation and Cooperates with Anti-CD3 to Preferentially Expand CD4$^+$ T Cells Thus, an increase in the number of CD4$^+$ T cells was observed, particularly in the spleen but also in the thymus. To further examine the effect of TSLP on T cells, the effect of TSLP injection on the in vivo proliferation of thymocytes was examined. γc KO mice treated with PBS or TSLP for 1 week were injected with BrdU 10 or 16 hours before sacrifice. TSLP increased BrdU incorporation in all subpopulations of thymocytes (FIG. 5E). Interestingly, $\gamma_c$ KO CD4$^+$ SP thymocytes had the lowest basal level of BrdU incorporation and were the most responsive to TSLP treatment, increasing their proliferation approximately four fold. Thus, TSLP enhanced the proliferation of all thymocyte subpopulations.

Figure 6:
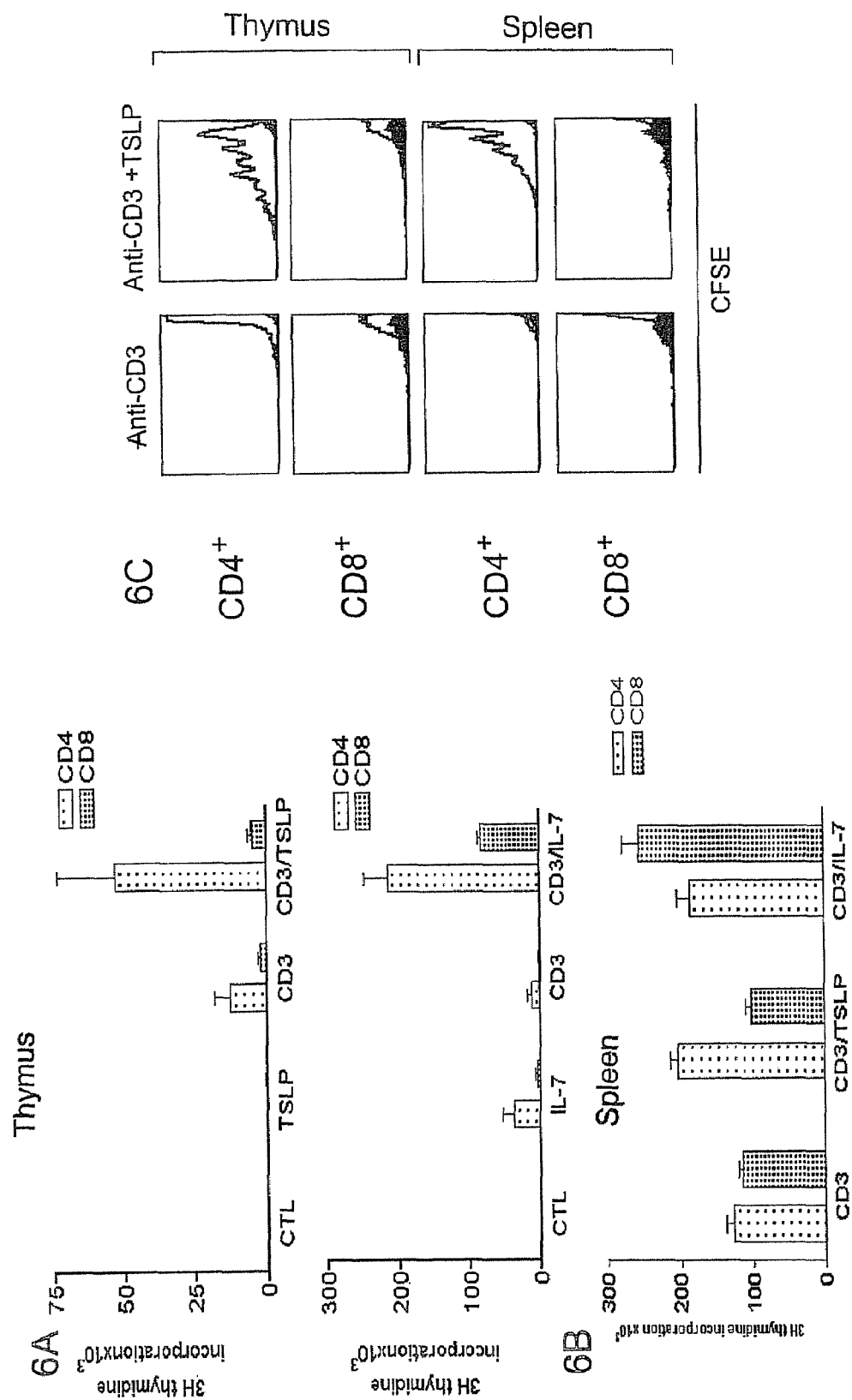
FIGS. 6A-6C are a set of bar graphs and plots showing that TSLP preferentially expands $CD4^+$ T cells. For the results shown in FIG. 6A and FIG. 6B, cells were treated with medium, IL-7 (100 ng/ml), or TSLP (100 ng/ml) and/or anti-CD3ε antibodies (2 μg/ml).
Figure 7:
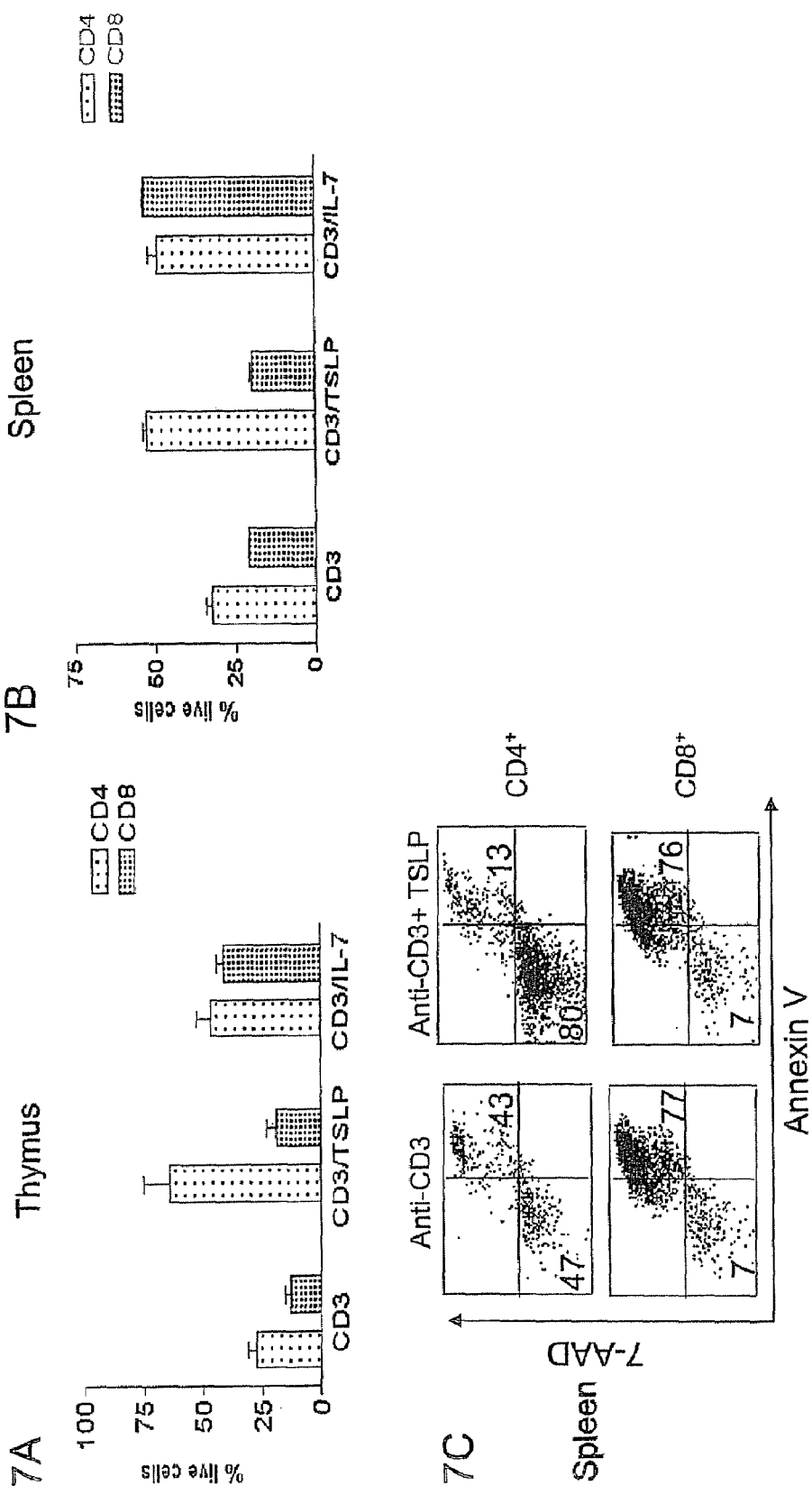
FIGS. 7A-7C are a set of bar graphs and plots showing that TSLP promotes survival of CD4$^+$ T cells.

To clarify the mechanism by which TSLP promotes thymocyte expansion, single positive WT thymocytes were treated in vitro with anti-CD3ε with or without IL-7 or TSLP. TSLP alone had no significant effect on the proliferation of either CD4$^+$ or CD8$^+$ SP thymocytes. However, when combined with anti-CD3ε, TSLP markedly increased the proliferation of CD4$^+$ SP thymocytes while its effect on CD8$^+$ SP thymocytes was much less (FIG. 6A, upper panel), suggesting that TSLP favors the expansion of CD4$^+$ thymocytes. In contrast, IL-7 enhanced proliferation of both CD4$^+$ and CD8$^+$ SP thymocytes alone or in combination with anti-CD3ε (FIG. 6A, lower panel), and overall, IL-7 was more potent then TSLP even for CD4$^+$ cells (note the difference in scale in the upper and lower panels of FIG. 6A). The ability of TSLP to influence the survival of SP thymocytes was also examined in vitro. Correspondingly, TSLP preferentially enhanced the survival of CD4$^+$ thymocytes, whereas IL-7 had similar effects on viability of CD4$^+$ and CD8$^+$ thymocytes (FIG. 7A). TSLP and IL-7 were equally potent in increasing the survival of DN and DP thymocytes.

Consistent with its effect on CD4$^+$ SP thymocytes, TSLP treatment preferentially enhanced TCR-induced proliferation (FIG. 6B) and survival (FIG. 7B and FIG. 7C) of CD4$^+$ splenic T cells as compared to CD8$^+$ T cells. Examining the proliferation of thymic and splenic CD4$^+$ cells using CFSE staining showed a dramatic dilution of CFSE staining in response to TSLP in both (FIG. 6C). Correspondingly, the percent of viable cells was increased (FIGS. 7A and 7B) and the percent of Annexin V$^+$/7-AAD$^+$ cells (FIG. 7 C) was decreased by TSLP.

As compared to CD4$^+$ T cells from WT mice, CD4$^+$ T cells from TSLPR KO mice exhibited less expansion during the 7 day period after injection into irradiated $\gamma_c$ KO mice (FIG. 8A), indicating that TSLP signaling is critical for an efficient expansion of CD4$^+$ lymphocytes even in an environment where IL-7 is not limiting and where endogenous CD4 cells expansion could occur. CFSE staining on day 3 showed the typical four to five divisions in WT CD4$^+$ T cells (FIG. 8B, upper left panel); however, TSLPR KO CD4$^+$ T cells persisted but had undergone fewer cell divisions (FIG. 8B, upper right panel). In contrast, CD8$^+$ T cells from WT and TSLPR KO mice were similar in their CFSE profiles. Taken together, these results indicate that TSLP preferentially enhances both the expansion and survival of CD4$^+$ T cells both in vitro and in vivo.

TSLP was discovered as a cytokine that could support the ability of pre-B cells to differentiate into more mature IgM$^+$ B cells, whereas IL-7 promotes development only to an IgM$^-$ stage (Friend et al., *Exp Hematol* 22:321-328, 1994). Colonies emerging from murine B220$^+$IgM$^-$ bone marrow cells develop into IgM$^+$ cells after 7 days of culture in TSLP. In contrast, TSLP was previously shown to play only a minimal role in murine T-lymphopoiesis by inducing proliferation of double negative thymocytes, but only in an IL-1-dependent manner (Sims et al., *J Exp Med* 192:671-680, 2000).

To clarify TSLP function, TSLPR deficient mice have been studied the effects of TSLP have been examined in vivo and in vitro. Despite ubiquitous expression, TSLPR is not required for the physical development and fertility of mice. In addition, TSLPR KO mice exhibit normal myeloid, lymphoid, dendritic cell and NK cell numbers, at least in part due to the continuous action of IL-7. To examine the role of TSLP in lymphopoiesis, TSLPR KO mice were crossed to $\gamma_c$ KO mice. Inactivating TSLP signaling in $\gamma_c$ KO mice further reduced the cellularity of the thymus, spleen, and BM, suggesting that TSLP can promote T and B cell expansion. Nevertheless, the existence of lymphocytes in these double KO mice indicates that other growth factors also contribute.

Cellular recovery following sub-lethal irradiation of TSLPR versus WT mice was evaluated. The defective cellular restoration in TSLPR KO mice suggests that TSLP is of use recovery from lymphopenia. Moreover, the defect was also more severe in TSLPR than WT mice injected with neutralizing antibodies to IL-7, indicating that TSLP has at least some actions that are independent of IL-7. Interestingly, however, in Jak3/TSLPR double KO mice, a decrease was observed in B cells in the spleen but not in the BM and saw no change in T cells. In contrast, in the above-described analysis of $\gamma_c$/TSLPR double KO mice, total cellularity declined with marked decreases in both B and T cells, findings that are consistent with a role for TSLP in $\gamma_c$-independent expansion of both of these lineages.

TSLP promoted B cell maturation in $\gamma_c$ mice to the B220+ IgM+ stage. It also enhanced B-cell maturation in WT mice to an almost identical level as IL-7, similar to what was reported in neonatal wild-type mice injected with TSLP (Sims et al, *J Exp Med* 192:671-680, 2000). Interestingly, B progenitor cells in the BM of $\gamma_c$ KO mice expanded and matured when animals were injected daily with TSLP for 1 week, but the effect was transient and no longer observed after three weeks of TSLP. TSLP had less of an effect in WT mice. Our findings in $\gamma_c$ KO mice could also reflect changing potentials of the progenitor population in these young animals.

Figure 8:
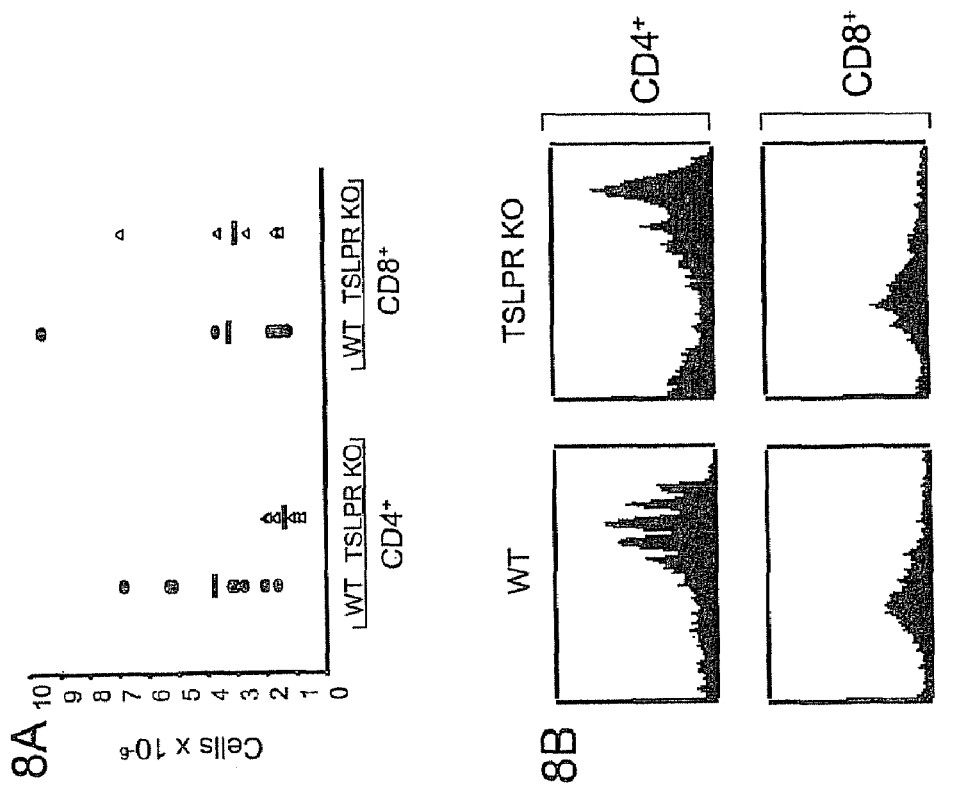
FIGS. 8A-8B are a graph and a set of plots showing that TSLP mediates efficient expansion of CD4$^+$ T cells. CD4$^+$ T cells were isolated from WT or TSLPR KO mice and labeled with CFSE before being injected into irradiated $\gamma_c$ KO mice.

A distinctive action of IL-7 is its ability to increase survival of immature thymocytes and provide a proliferative signal in the pre-T cell stage after TCR-β rearrangement (Zlotnik et al., *Curr Opin Immunol* 7:206-213, 1995). IL-7 is also essential for γδ TCR generation (Moore et al., *J Immunol* 157:2366-2373, 1996). Although TSLP could not rescue γδ T cell development when it was injected into $\gamma_c$ KO mice, like IL-7, TSLP could promote the survival and proliferation of T cells as well as in B cells from WT mice. Strikingly, TSLP can preferentially increase TCR-mediated proliferation of CD4+CD8- thymocytes and CD4+ peripheral T cells in vitro (FIG. 6), and the absence of TSLP signaling hinders the expansion of these cells in vivo in the adoptive transfer experiment (FIG. 8). The modest effect of TSLP on CD4+ T cell expansion seen in wild-type mice (FIG. 2) could be related to the presence of IL-7, which in addition to its effect on CD8+ T cells homeostasis, can also promote CD4+ T cell survival (Seddon et al., *Nat Immunol* 4:680-686, 2003). Without being bound by theory, it is also possible that the T cell compartment is already "filled", allowing less expansion and/or that it is less responsive as cells have already received signals from $\gamma_c$-dependent cytokines so that a potentially redundant signal from TSLP would have little effect. Interestingly, two other $\gamma_c$ cytokines, IL-7 and IL-15, preferentially induce an expansion of CD8+ T cells rather than CD4+ T cells (Kieper et al., *J Exp Med* 195:1533-1539, 2002; Schluns et al., *Nat Rev Immunol* 3:269-279, 2003; Lodolce et al., *Immunity* 9:669-676, 1998).

Like IL-7 and IL-15, TSLP activates Stat5a and Stat5b (Isaksen et al., *J Immunol* 163:5971-5977, 1999; Isaksen et al., *J Immunol* 168:3288-3294, 2002). Stat5a and Stat5b transgenic mice show an increase in CD8+ T cells (Kelly et al., *J Exp Med* 198:79-89, 2003; Kelly et al., *J Immunol* 170:210-217, 2003) which suggests that Stat5 by itself is unlikely to be mediating the TSLP effect on CD4+ T cell expansion. Unlike IL-7, TSLP had no effect on the in vitro proliferation of thymocytes unless combined with TCR activation. Since the differentiation of CD4+CD8+ thymocytes into single positive cells is based on MHC-specificity of their TCR signal and the strength of the TCR engagement (Germain et al., *Nat Rev Immunol* 2:309-322, 2002), it is conceivable that TSLP provides a selective co-stimulatory signal that favors the CD4+CD8- intermediate stage by enhancing the activation of these cells. Moreover, TSLP could compete with IL-7 for the IL-7Rα subunit, thus hindering the ability of IL-7 to promote CD8+ T cell expansion in WT mice. Interestingly, IL-7 has been suggested to be important as a survival factor for CD4 memory cells (Seddon et al., *Nat Immunol* 4:680-686, 2003). The results described above in the murine system with purified CD4+ and CD8+ SP thymocytes as well as splenic T cells suggest a direct effect of TSLP on CD4+ T cells. Thus, TSLP and IL-7, both of which share IL-7Rα, likely are important for CD4+ T cell homeostasis.

Thus, evidence is provided herein that demonstrates that TSLP plays a role in T cell expansion both in vitro and in vivo, particularly of CD4+ T cells. TSLP could play a role in CD4+ T cell homeostasis. This preferential action of TSLP for CD4+ versus CD8+ T cells likely explains the relative augmentation in CD4+ T cells in $\gamma_c$ KO mice.

Example 9

Materials and Methods for Example 10

Mice: TSLPR KO mice are described above. DO11.10 transgenic Rag $2^{-/-}$ mice on B10.D2 and Balb/c backgrounds (purchased from Taconic) were crossed to TSLPR KO mice on F1 129/BL/6 or Balb/c (F4) genetic backgrounds. WT Balb/c animals were from the Jackson Laboratory.

TSLP effect on naïve versus memory CD4 T cells: CD4+CD62L+CD44$^{low}$ (naïve), CD4+CD62L+CD44$^{high}$ (central memory), and CD4+CD62L-CD44$^{high}$ (effector memory) phenotype T cells were isolated by cell sorting and were >99% pure. RNA was extracted from freshly sorted cells using Trizol (Invitrogen). Purified cells were also suspended at ($2\times10^5$ cells/well) and activated with anti-CD3ε (2 μg/ml, Pharmingen) with or without TSLP (100 ng/ml, R and D) for 48 hours before being pulsed with 1 μCi of [$^3$H] thymidine (6.7 Ci/mmol, NEN, Boston, Mass.) for the final 16 hours of culture.

Immunization and antigen-recall response: Mice were immunized by intra-peritoneal injection of 200 μg of ovalbumin (OVA) (Pierce, Rockford, Ill.) in 100 μl of PBS that had been emulsified with an equal volume of Aluminum Hydroxide (ALUM) as adjuvant. Mice were sacrificed 12 or 60 days after immunization. For assessing an antigen recall response, purified CD4+ T cells ($1\times10^5$ cells/well) were cultured with an equal number of splenic antigen presenting cells (APCs) or total splenocytes ($2\times10^5$ cells/well) that were treated with mitomycin C (50 μg/ml in PBS for 15 minutes at 37° C.) and washed 3 times. These cells were then incubated in 96 well flat-bottom plates for 48 hours in RPMI 1640 medium containing 10% FBS, 2 mM L-glutamine, and antibiotics, and with 0, 10, 50 or 200 μg/ml of OVA. Wells were pulsed with 1 μCi of [$^3$H] thymidine (6.7 Ci/mmol, NEN, Boston, Mass.) for the final 16 hours of culture. Where indicated, APCs included B cells, macrophages, and dendritic cells (DC), after depleting CD4+ T cells, CD8+ T cells, and natural killer (NK) cells by positive selection. Wild-type (WT) and TSLPR KO mice expressing the DO11.10 transgene were treated with 100 μg of OVA emulsified in ALUM and analyzed the next day.

Dendritic cell function: TSLP was from R&D Biosystems and tested negative for endotoxin by the LAL (*Limulus Amebocyte* Lysate) test (BioWhittaker, MD). To examine the effect of TSLP on murine DC, total splenic CD11c+ DC were isolated by sorting (>99% purity) from Balb/c WT mice and cultured for 24 hours at $1\times10^6$ cells/ml with OVA$^{323-339}$ peptide (5 μg/ml) (Bachem, King of Prussia, Pa.) with or without TSLP (100 ng/ml). The cells were lysed in Trizol for RNA isolation or were washed, treated with mitomycin C (50 μg/ml, Sigma), washed three times, and incubated with DO11.10 RAG $2^{-/-}$ CD4+ T cells at 1:10 ratio. Cells were either cultured for 48 hours to allow measuring proliferation using [$^3$H] thymidine incorporation or for four days to examine intracellular levels of IFN-δ and IL-4 secretion, as described below.

"Mix and match" experiments were performed using CD4+ T cells purified by positive selection using specific magnetic beads (Miltenyi Biotec). CD4+ T cells and CD11c+ DC were isolated by positive selection using labeled magnetic beads (Miltenyi Biotec) in the presence of 1% Fc block (PharMingen). The resulting CD4+ T cells were >90% pure and DC were >80% pure. They were incubated together (1:10 ratio) at various combinations (for example, WT CD4+ T cells with WT or TSLPR KO DC and TSLPR KO CD4+ T cells with WT or TSLPR KO DC) as indicated. All DC were treated with mitomycin C before being incubated with CD4+ T cells. Wells were pulsed with 1 µCi of [$^3$H] thymidine (6.7 Ci/mmol, NEN, Boston, Mass.) for the final 16 hours before harvesting.

Flow cytometric analyses: Single cell suspensions were prepared from thymus and spleen. Cells were washed with FACS buffer (phosphate buffered saline pH 7.4 containing 0.5% bovine serum albumin (BSA) and 0.02% sodium azide). One million cells were treated with Fc-block for 15 minutes before being incubated with the indicated fluorochrome-conjugated antibodies (all from PharMingen) for 20 minutes. Cells were then washed twice with FACS buffer and analyzed. All antibodies used were from PharMingen except KJ1-26 mAb, which was from Caltag Laboratories (Burlingame, Calif.).

Culture under polarizing conditions: Purified CD4+ T cells were activated with anti-CD3 (2 µg/ml) and anti-CD28 (1 µg/ml) and cultured in conditions favoring Th1 (1 ng/ml IL-12 and 10 µg/ml anti-IL-4) or Th2 (1 ng/ml IL-4 and 20 µg/ml anti-IFN-γ) in the presence or absence of TSLP (100 ng/ml). IL-2 (100 U/ml) was added on day 2 and cells were allowed to expand for 1 week.

Intracellular staining for IFNγ and IL-4 levels: Cultured cells were activated with PMA (10 ng/ml) and ionomycin (1 µg/ml) (both from Sigma) for 5 hours in the presence of Golgi Block (PharMingen). Cells were washed and stained for either anti-CD4 (PharMingen) and/or for the DO11.10 specific transgene with KJ1-26. Intracellular staining was performed using Cytofix/Cytoperm kit and anti-IFN-δ and IL-4 (all from PharMingen) according to the manufacturer's instructions.

Sensitization and airway challenge to mice: OVA (100 µg) was emulsified at a 1:1 ratio in ALUM in 200 µl and injected intraperitoneally on days 0 and 7 to sensitize mice. On day 13, mice were challenged intratracheally with 50 µg of OVA in 30 µl PBS. On day 14, 50 µg of OVA in 25 µl PBS was administered intranasally. Control mice were treated similarly with PBS instead of OVA. On day 16, mice were sacrificed, bled, and bronchoalveolar lavage (BAL) was performed using 0.5 ml of PBS. Cells from BAL fluid were isolated by cytospin and leukocytes identified by staining using Wright/Giemsa. Lungs were either used for extracting RNA or for generating tissue sections for microscopic analysis. Lung tissue sections were stained with either Periodic-Acid Schiff (PAS) or Wright/Giemsa (Volu-Sol, UT). Serum levels of OVA-specific immunoglobulin were measured by ELISA (PharMingen). Inflammation was scored on a scale of 0 to 4 as follows: (0) Normal lungs, no goblet cell hyperplasia; (1) Minor perivascular inflammation around large blood vessels; (2) Moderate perivascular and peribronchial inflammation, minimal evidence of goblet cell hyperplasia; (3) Increased perivascular and peribronchial inflammation with increased goblet cell hyperplasia beginning in smaller airways; (4) Severe formation of perivascular, peribronchial, and interstitial inflammation as well as goblet cell hyperplasia in both small and large airways.

Adoptive transfer of CD4+ T cells: WT and TSLPR KO mice backcrossed to Balb/c background for four generations were designated as donors and recipients and immunized by intraperitoneal injections of OVA (100 µg) emulsified at a 1:1 ratio in ALUM in 200 µl on days 0 and 7. On day 13, recipient mice were sensitized intratracheally with 50 µg of OVA in 30 µl PBS, followed 4 hours later by i.v. transfer of 8×10$^6$ CD4' T cells extracted from spleen and lymph nodes of donor mice. On day 14, 50 µg of OVA in 25 µl PBS was administered intranasally. Mice were sacrificed and analyzed the next day for signs of lung inflammation, using the criteria presented above.

Real time PCR: RNA was extracted from single cell suspensions or from lung tissue using Trizol (Invitrogen). RNA was reverse transcribed using the RNA PCR gold kit (Applied Biosystems). Levels of IL-2, IL-4, IL-5, IL-10, IL-13, IFN-γ, TSLP, and TSLPR mRNA relative to 18S rRNA were measured by RT-PCR using "Gene expression assays" readymade primers from Applied Biosystems.

Example 10

Further Analysis of the Effect of TSLP

Figure 10:
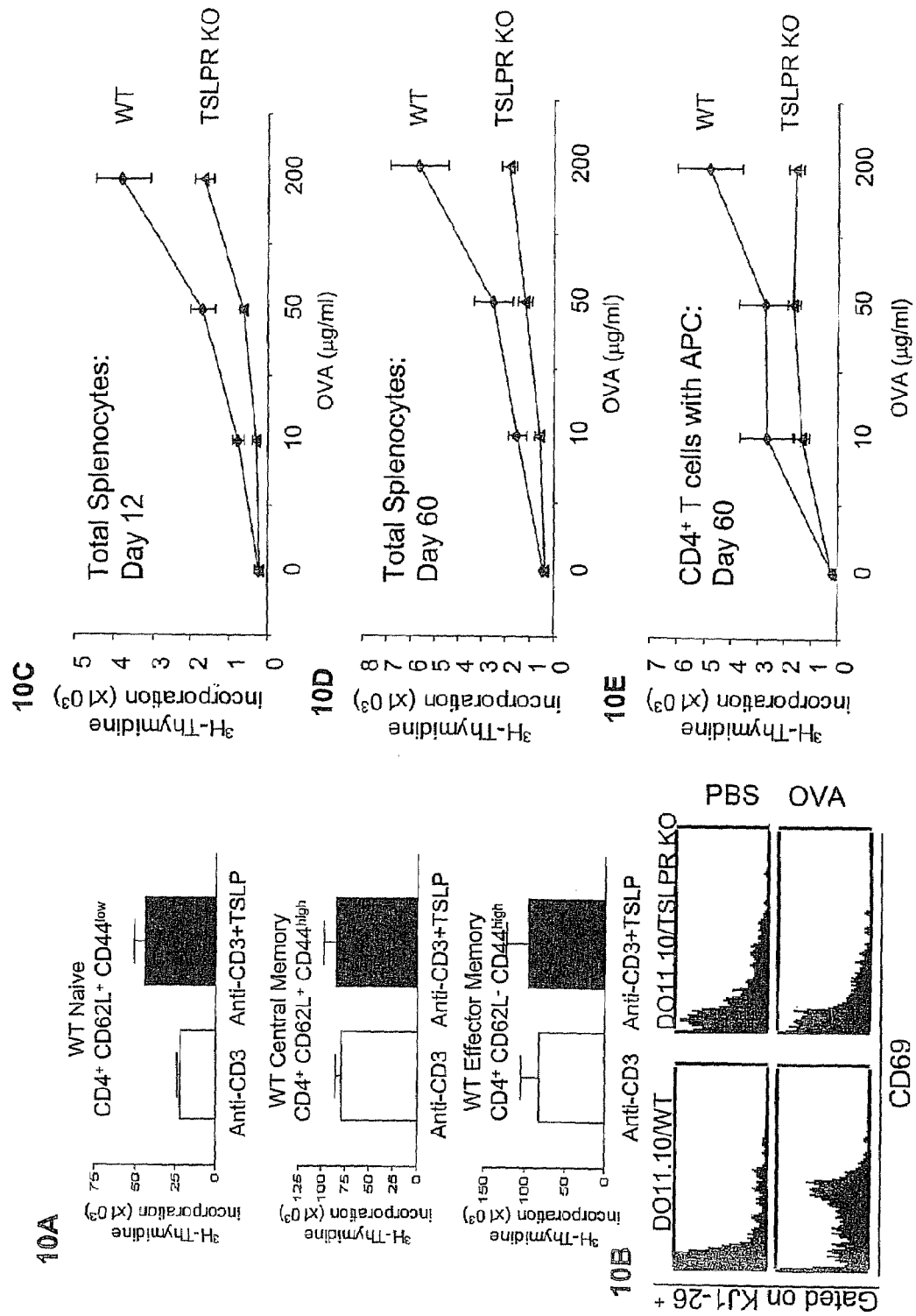
FIGS. 10A-10E are a set of graphs and plots showing TSLP promotes the proliferation of naive CD4$^+$ T cells. For the results shown in the bard graph shown in FIG. 10A, purified naive (CD4$^+$CD62L$^+$CD44$^-$), central memory (CD4$^+$CD62L$^+$CD44$^+$), and effector memory (CD4$^+$CD62L$^-$CD44$^+$) T cells from WT Balb/c mice were activated for 48 hours with 2 μg/ml anti-CD3 with or without 100 ng/ml TSLP and then pulsed with $^3$H thymidine for 16 hours. TSLP significantly increased the proliferation of naive CD4$^+$ T cells (p=0.01) (upper panel) but did not significantly affect memory CD4$^+$ T cells proliferation (middle and lower panels). Lower concentrations of anti-CD3 (0.2-0.5 μg/ml) had a similar preferential effect on naive CD4$^+$ T cells (data not shown). For the results shown in the plots shown in FIG. 10B, WT and TSLPR KO mice expressing the DO11.10 transgene were injected with OVA and ALUM (i.p.) and analyzed the next day. DO11.10/WT but not DO11.10/TSLPR KO mice expressed high levels of CD69. For the results shown in the graphs of FIGS. 10C, 10D and 10E, WT and TSLPR KO mice (not expressing the DO11.10 transgene) were immunized with ovalbumin (OVA) (200 μg) and ALUM. Animals were sacrificed on day 12 (FIG. 10C) or 60 (FIG. 10D) and splenocytes were cultured with OVA (0, 10, 50, and 200 μg/ml). Splenocytes from TSLPR KO mice displayed significantly lower proliferation in response to secondary encounter with antigen at all concentrations tested (p<0.05 for all). For the results graphed in FIG. 10E, CD4$^+$ T cells purified from mice 60 days after immunization were incubated with APC (splenocytes that were depleted of T and NK cells) in the presence of different doses of OVA. CD4$^+$ T cells from TSLPR KO mice displayed significantly lower proliferation in response to the OVA (200 μg/ml) in vitro (p<0.01) than CD4$^+$ T cells from WT mice. Shown are means ±SEM for 5 experiments.

To better understand the function of TSLP in immune responses and to clarify the CD4+ T cell population(s) on which it acts, the effect on naïve (CD62L+CD44$^{low}$), central memory (CD62L+ CD44$^{hi}$) and effector memory (CD62L− CD44+) CD4+ T cell populations was examined. TSLP significantly enhanced the anti-CD3 induced proliferation of naïve CD4+ T cells from Balb/c mice, but had little effect on the expansion of memory phenotype CD4+ T cells (FIG. 10A).

To further analyze the effect of TSLP in vivo, TSLPR KO mice were crossed to DO11.10 transgenic (Tg) mice and analyzed mice that expressed the TCR transgene and either expressed (DO11.10/WT) or lacked (DO11.10/TSLPR KO) the TSLPR gene. Splenic CD4+ T cells from these animals were examined; DO11.10/WT and DO11.10/TSLPR KO CD4+ T cells expressed little if any CD69, an early T-cell activation marker (FIG. 10B, upper panels). However, injection of mice with ovalbumin (OVA) significantly induced CD69 on DO11.10/WT CD4+ T cells but not DO11.10/ TSLPR KO (FIG. 10B, lower panels), indicating that the absence of TSLP signaling diminishes the activation of naïve CD4+ T cells by antigen in vivo.

The role of TSLP in TCR-driven generation of memory T cells from naïve CD4+ T cells was examined. WT and TSLPR KO mice on a Balb/c WT background (that do not express the DO11.10 transgene) were immunized with OVA. As evaluated by an in vitro antigen recall assay, splenocytes isolated from TSLPR KO mice 12 or 60 days after immunization had a lower proliferative response to secondary exposure to the antigen than did splenocytes from WT mice (FIGS. 10C and 10D). CD4+ T cells were isolated 60 days after immunization and cultured with antigen presenting cells (APC) at a 1:1 ratio in the presence of OVA. CD4+ T cells from TSLPR KO mice showed much weaker proliferation in response to secondary antigen exposure than did cells from WT littermates (FIG. 10E). These results suggest that TSLP is primarily involved in antigen-driven activation of naïve CD4+ T cells and its absence significantly diminishes the generation of memory T cells.

Example 11

TSLPR Plays a Role in the Activation of Dendritic Cells in Mice

Figure 11:
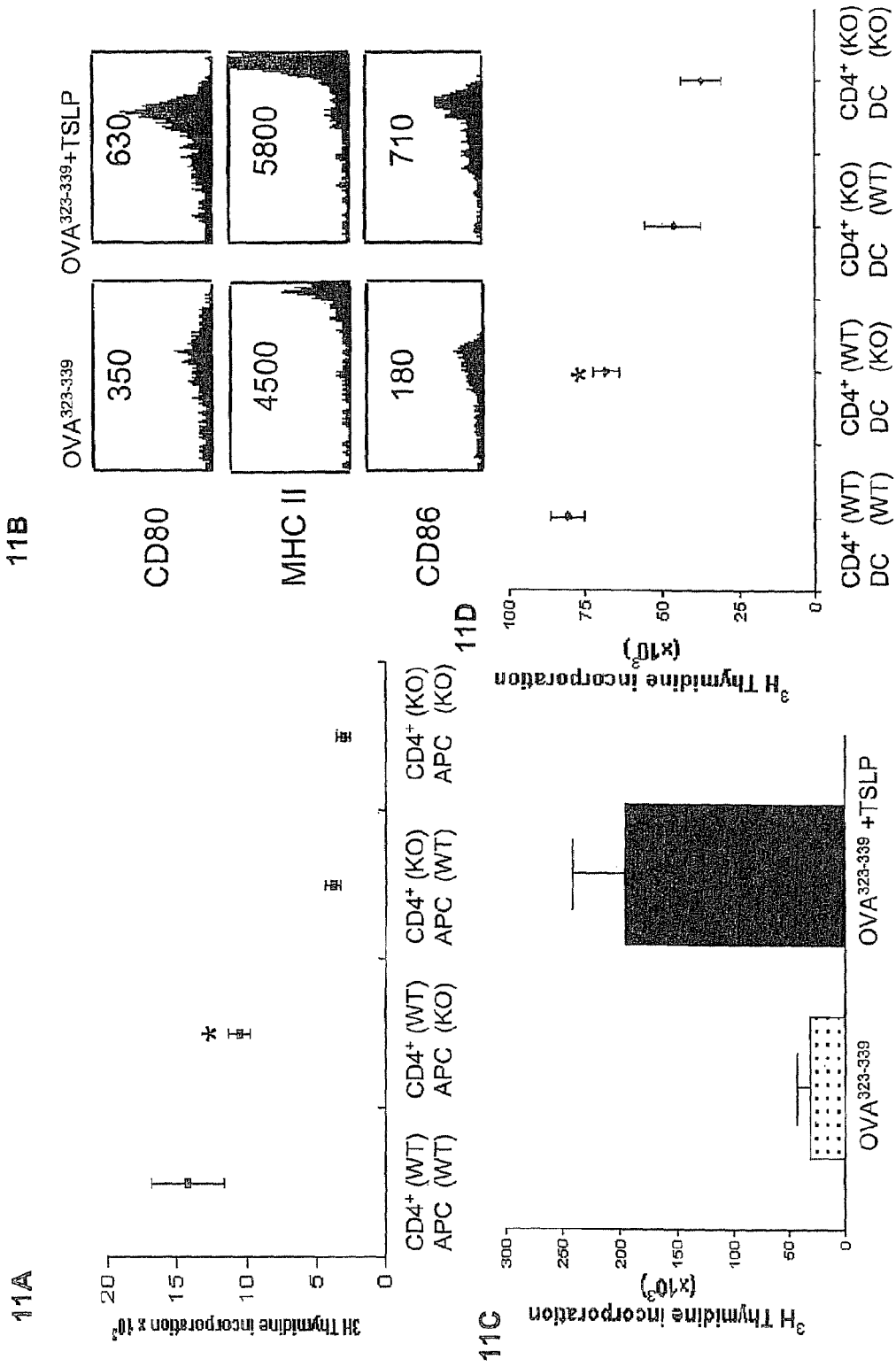
FIGS. 11A-11D are a set of images showing that TSLP activates murine DC.

The effect of TSLP on the contribution of APCs to the expansion of CD4+ T cells in response to secondary stimulation was examined in vitro. WT and TSLPR KO mice were immunized with OVA, sacrificed at day 60, and splenic CD4+ T cells were purified and incubated at a 1:1 ratio with APCs in the presence of OVA. WT CD4+ T cells cultured with WT APCs proliferated the most. Replacement of WT APCs with TSLPR KO APC mildly (but significantly) reduced T-cell proliferation (FIG. 11A). TSLPR KO CD4+ T cells showed the weakest proliferative response to antigen, and this was not significantly increased by introducing WT APC (FIG. 11A). Thus, TSLP has an essential role for CD4+ T cells, but the decreased proliferation of WT CD4+ T cells when TSLPR KO APC were used suggests that TSLP signaling is required for the optimal activity of APCs as well.

In view of the findings above, the role of murine TSLP on WT DC was investigated. It was confirmed that WT DC express TSLPR mRNA using RT-PCR. When WT splenic CD11c+ DC were activated with $OVA^{323-339}$ peptide for 24 hours, the addition of TSLP moderately increased the cell surface expression of CD80, CD86, and MHC II (FIG. 11B). As compared to untreated DC, TSLP-treated DC also significantly enhanced peptide-mediated proliferation of DO11.10 TCR transgenic CD4+ T cells when the DC and T cells were incubated in a 1:10 ratio (FIG. 11C).

To further examine the effect of TSLP on the ability of DC to activate naïve cells, splenic CD4+ T cells and DC were isolated from non-immunized DO11.10/WT and DO11.10/TSLPR KO mice, and cultured DC with CD4+ T cells at a 1:10 ratio in the presence of 5 μg/ml of $OVA^{323-339}$ peptide. As expected, DO11.10/WT CD4+ T cells cultured with WT DC showed the highest levels of proliferation. This was slightly but significantly reduced when DO11.10/WT CD4+ T cells and DO11.10/TSLPR KO DC were used (FIG. 11D). The weak expansion seen when TSLPR KO CD4+ T cells were incubated with TSLPR KO DC was not significantly enhanced when WT DC were used. These results indicate that TSLP activates murine DC, but that the presence of TSLPR on CD4+ T cells is more critical than its presence on DC for optimal proliferation to the $OVA^{323-339}$ peptide, consistent with the results shown in FIG. 11A.

Example 12

TSLP-treated DC Reduce IFN-γ Production by CD4+ T Cells

Figure 12:
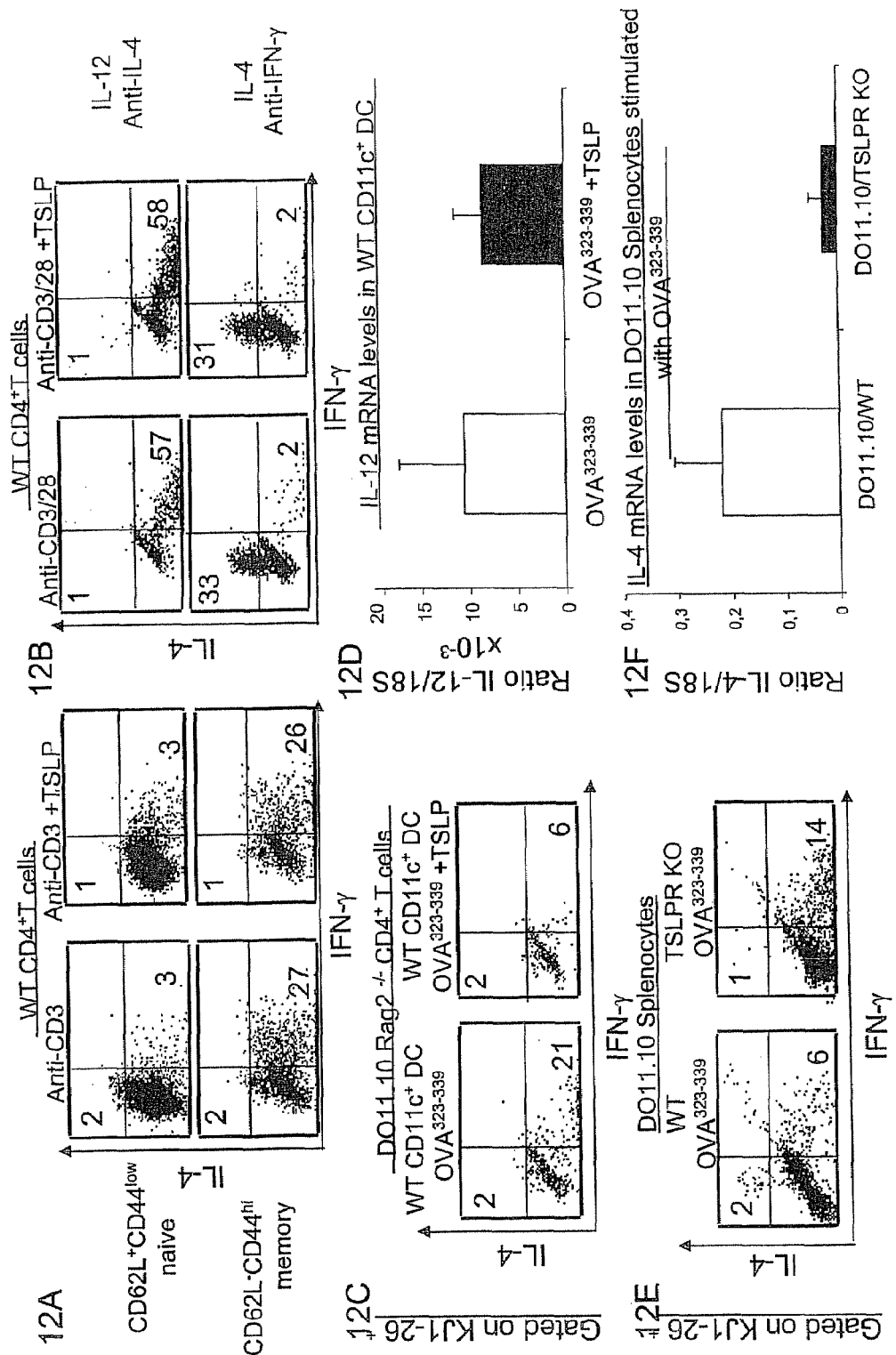
FIGS. 12A-12F are a set of images showing that DC activated with TSLP negatively regulates IFN-δ production by naive CD4$^+$ T cells. Cells were cultured before being treated with PI, and the intracellular levels of IFN-δ and IL-4 were measured by intracellular staining. For the plots shown in FIG. 12A, naive and memory CD4$^+$ T cells were isolated (>99% pure) from WT animals and treated with anti-CD3 with or without TSLP for 4 days. The addition of TSLP had no effect on the levels of IFN-δ and IL-2 produced by CD4$^+$ T cells. For the plots shown in FIG. 12B, purified CD4$^+$ T cells were activated with anti-CD3/anti-CD28 under Th1 (IL-12 and anti-IL-4) or Th2 (IL-4 and anti-IFN-γ) polarizing conditions with or without TSLP. IL-2 was added on day 2, and cells were allowed to grow for 1 week. TSLP did not affect the IFN-δ or IL-4 production by these polarized cells. For the plots shown in FIG. 12C, sorted splenic CD11c$^+$ DC were incubated with 5 µg/ml of OVA$^{323\text{-}339}$ peptide alone or with TSLP before being washed, treated with mitomycin C, and cultured with purified CD4$^+$ T cells from DO11.10 RAG2$^{-/-}$ mice at a 1:10 ratio from non-immunized animals. TSLP-treated DC reduced the levels of IFN-δ production by KJ1-26$^+$CD4$^+$ T cells, whereas the levels of IL-4 were not affected.

Because TSLPR is critical for naive CD4+ T-cell proliferation, it was next examined whether TSLP could influence the cytokines produced by CD4+ T cells in response to TCR stimulation. Naive $CD4^+CD62L^+CD44^{low}$ and effector memory $CD4^+CD62L^-CD44^{hi}$ splenic T cells were purified from WT Balb/c mice and activated the cells with anti-CD3 in the presence or absence of TSLP. On day 4, cells were stimulated with PMA+ionomycin for 5 hours and intracellular levels of IFN-δ and IL-4 were determined. TSLP did not affect the level of IFN-δ or IL-4 in naive or memory CD4+ T cells under neutral conditions (FIG. 12A). Furthermore, when cells were activated using Th1 or Th2 polarizing conditions, the addition of TSLP did not affect the levels of either cytokine (FIG. 12B).

It was next examined whether TSLP could indirectly influence the differentiation of CD4+ T cells by its action on DC. Sorted WT splenic CD11c+ DC were pre-incubated with $OVA^{323-339}$ in the presence or absence of TSLP before being washed and incubated with congenic DO11.10 Tg CD4+ T cells (on a $RAG2^{-/-}$ background). Treatment of DC with TSLP+$OVA^{323-339}$ reduced the levels of IFN-δ production in $KJ1-26^+CD4^+$ DO11.10 Tg T cells (FIG. 12C). Under these conditions, the levels of IL-12 produced by DC were below the level of detection sensitivity by ELISA. Real time PCR showed treatment of DC with $OVA^{323-339}$+TSLP versus $OVA^{323-339}$ alone tended to decrease IL-12 mRNA levels but the difference was not statistically significant (FIG. 12D). IFN-δ and IL-4 production was examined in TSLPR KO mice. Splenocytes from WT and TSLPR KO mice expressing the DO11.10 transgene were cultured in vitro in the presence of $OVA^{323-339}$. After 4 days of culture, $KJ1-26^+CD4^+$ T cells from DO11.10/TSLPR KO mice consistently produced more IFN-δ than the analogous T cells from DO11.10/WT mice (FIG. 12E). Changes in the level of IL-4 production were difficult to evaluate by intracellular staining because it was so low in WT mice (FIG. 12E). IL-4 levels were measured by RT-PCR (FIG. 3F). It was found that splenocytes from DO11.10/TSLPR KO mice produced significantly lower levels of IL-4 than DO11.10/WT mice. These results suggest that TSLP can indirectly influence cytokine production by CD4+ T cells by modulating the activity of DC.

Example 13

TSLPR KO Mice Fail to Develop a Lung Inflammatory Response to OVA Antigen

Figure 13:
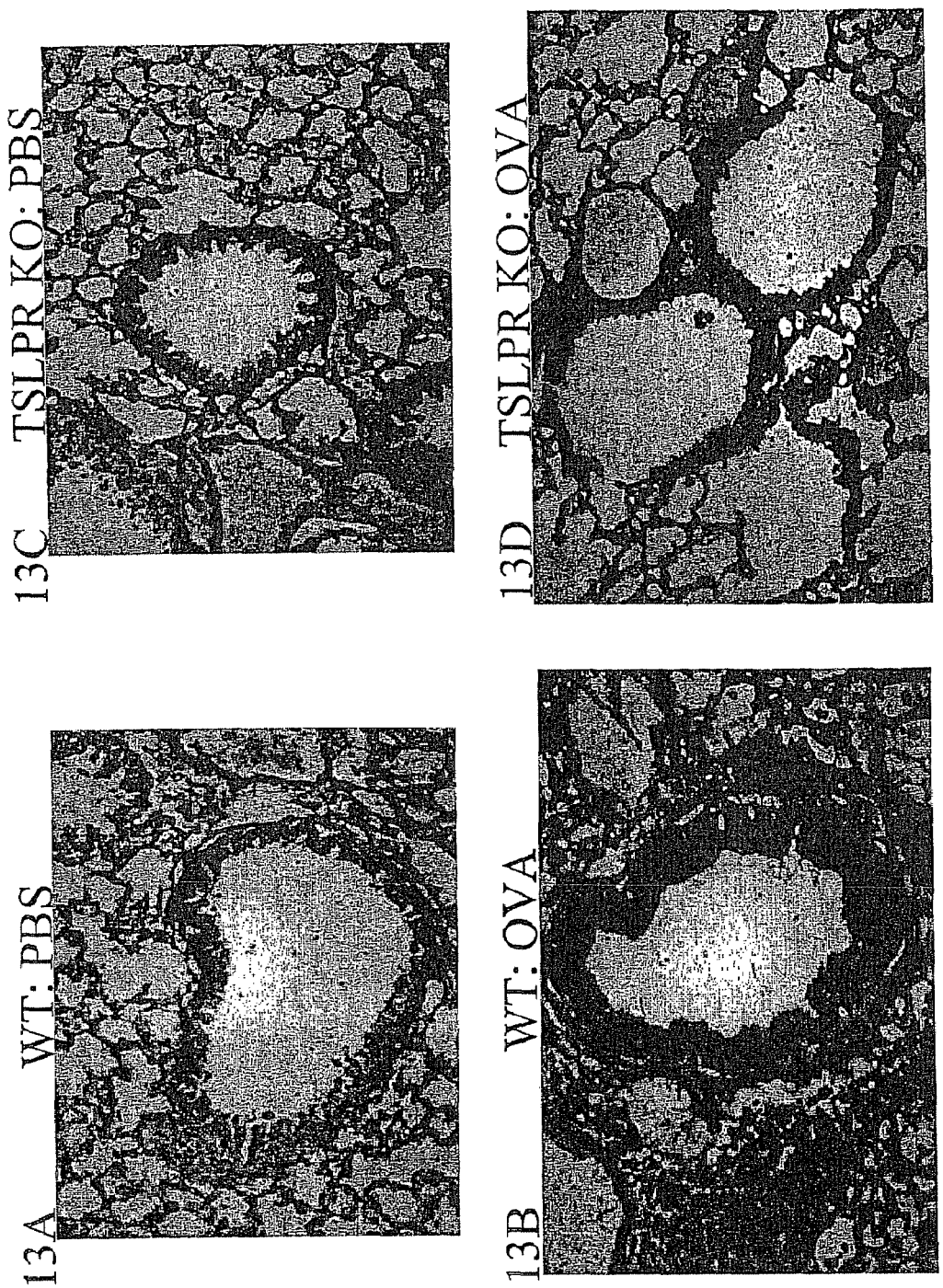
FIGS. 13A-D are a set of digital images showing that TSLPR KO mice fail to mount an inflammatory response. PAS-stained lung tissue sections (40× magnification) of Balb/c WT and TSLPR KO mice that were sensitized (i.p.) and challenged (i.t. and i.n.) with OVA or PBS (i.p.). Upper panels display no obvious differences in the lung morphology between WT and TSLPR KO animals in the resting state. WT mice receiving OVA displayed perivascular, peribronchiolar cuffing, and goblet cell hyperplasia (lower left panel), whereas TSLPR KO mice treated with OVA showed no obvious inflammation (lower right panel).

Because of the ability of TSLP to regulate the immune response of CD4+ T cells, the ability of TSLPR KO mice to control an inflammatory response was examined, using the OVA-induced allergic inflammatory response in the lung (Keane-Myers et al., *J Immunol* 161:919-926, 1998). WT and TSLPR KO (F4 Balb/c) mice were immunized twice intraperitoneally i.p.) with OVA and challenged by intratracheal (i.t.) and intranasal (i.n.) administration of OVA. As expected in this model, WT mice receiving OVA had perivascular inflammation and showed marked peribronchiole cuffing with inflammatory cells, as evidenced by inflammatory cells forming rings around both the vasculature and bronchioles (FIG. 13B versus FIG. 13A). PAS staining of the mucoid components in goblet cells revealed that WT mice also exhibited goblet cell hyperplasia. These mice scored 3-3.5 out of 4 on the inflammation scale and showed infiltration of eosinophils and neutrophils (Table 3) as compared with control WT animals. In sharp contrast, TSLPR KO mice treated with OVA had profoundly fewer cellular infiltrates in the lungs and little to no goblet cell hyperplasia in the bronchi after antigen challenge (FIG. 13D versus 13C) and very few inflammatory cells (Table 3). There were no obvious differences between control WT and TSLPR KO mice treated with PBS (FIG. 13C versus 13A, upper panels and FIG. 17 (which is Table 3).

Figure 14:
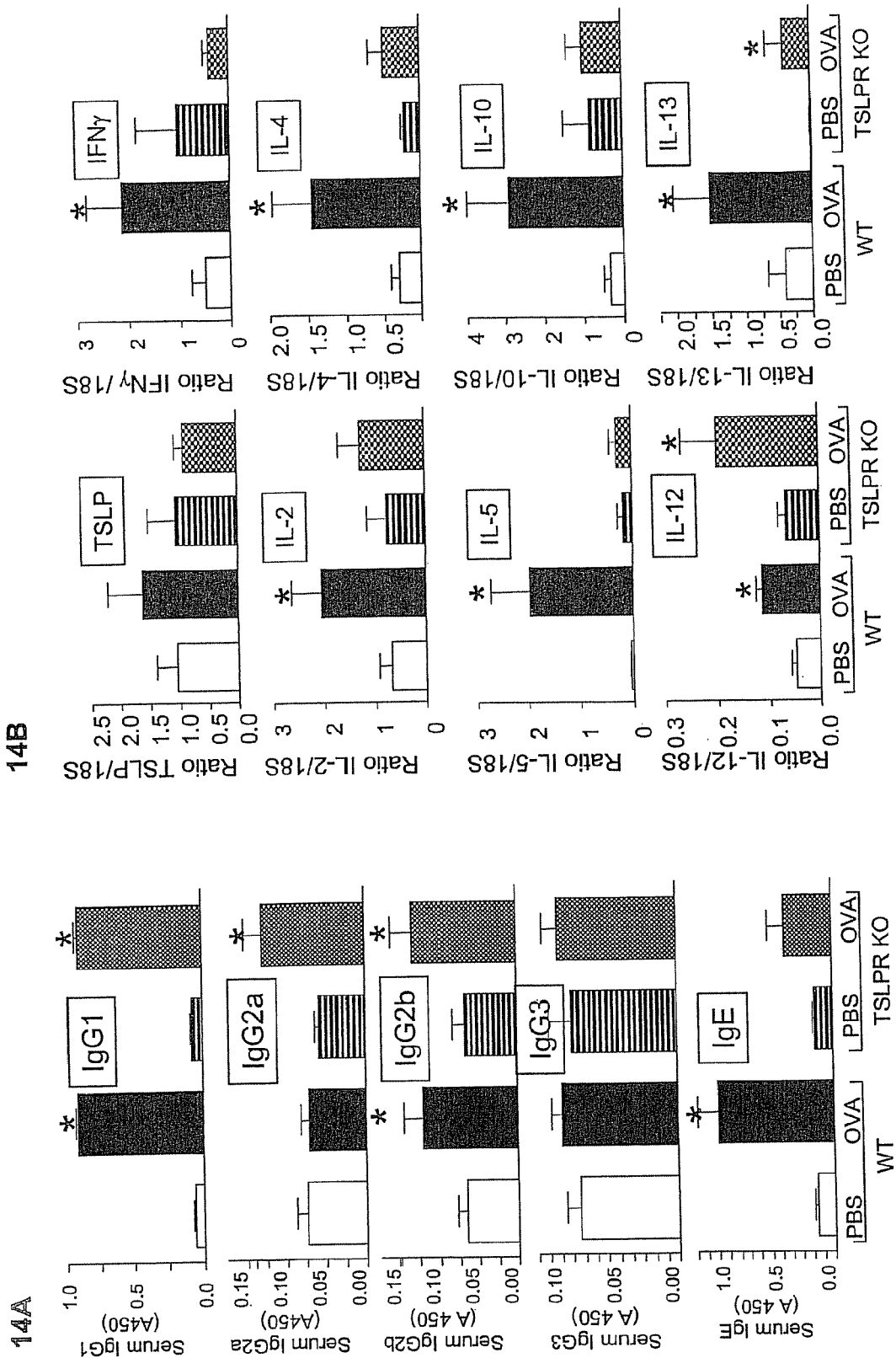
FIGS. 14A-14B are a set of bar graphs showing the absence of TSLPR inhibits allergic/inflammatory immunoglobulin and cytokine profiles in the lungs. Balb/c WT and TSLPR KO mice were sensitized (i.p.) and challenged (i.t. and i.n.) with OVA or PBS (i.p.).

Corresponding to the TSLPR KO mice having a defective "allergic" response, WT and TSLPR KO mice had significantly lower levels of IgE and higher IgG2a than did WT mice (FIG. 14A). Levels of OVA-specific IgG1, IgG2b, and IgG3 were normal (FIG. 14A). Furthermore, unlike WT mice, TSLPR KO mice sensitized to OVA and subsequently challenged with OVA did not show a statistically significant increase in IL-2, IL-4, IL-5, IL-10, IL-13, and IFN-δ mRNA as compared to PBS-treated mice (FIG. 14B). These findings are consistent with the greatly diminished infiltration of inflammatory cells in TSLPR KO animals. Interestingly, OVA induced an increase in IL-13 mRNA, as evaluated by RT-PCR, in the lungs of TSLPR KO mice, but only to levels seen in PBS-treated WT controls (FIG. 14B). They also displayed a significant increase in IL-12 mRNA (FIG. 14B). These results indicate that TSLP is essential for mounting an optimal pulmonary inflammatory response to OVA.

Figure 15:
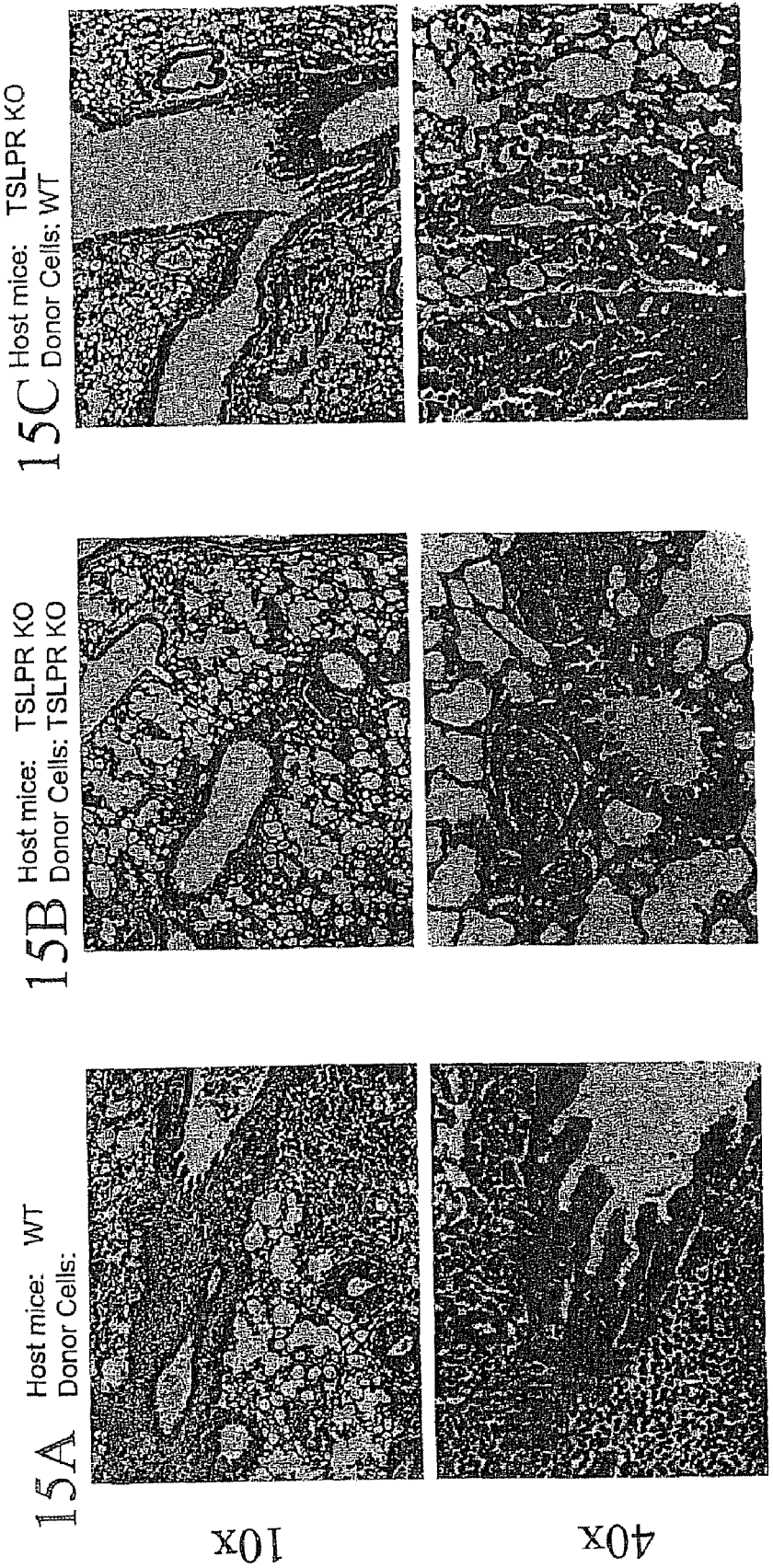
FIGS. 15A-15C are a set of digital images showing TSLPR KO mice succeed in mounting an inflammatory response in the lung after receiving WT CD4$^+$ T cells. Donor and recipient mice (F4 Balb/c) were sensitized with OVA (i.p.). Recipient mice were challenged with OVA (i.t.) 4 hours before receiving $8\times10^6$ of total CD4$^+$ T cells. CD4$^+$ T cells from WT donor were transferred to WT (positive control) and TSLPR KO (test subject) mice while CD4$^+$ T cells from TSLPR KO mice were given to TSLPR KO mice to act as negative control. All mice were treated the next day with OVA (i.n.) and sacrificed 24 hours later. Shown are the PAS staining of lung tissue sections at 10× and 40× magnification. The WT positive control displayed perivascular, peribronchiolar cuffing, and goblet cell hyperplasia (FIG. 15A) while TSLPR KO mice showed no signs of lung inflammation (FIG. 15B). However, TSLPR KO mice that were supplemented with CD4$^+$ T cells (FIG. 15C) exhibited inflammatory cells infiltration combined with peribronchiolar cuffing, and goblet cell hyperplasia in the large and medium airways.
Figure 16:
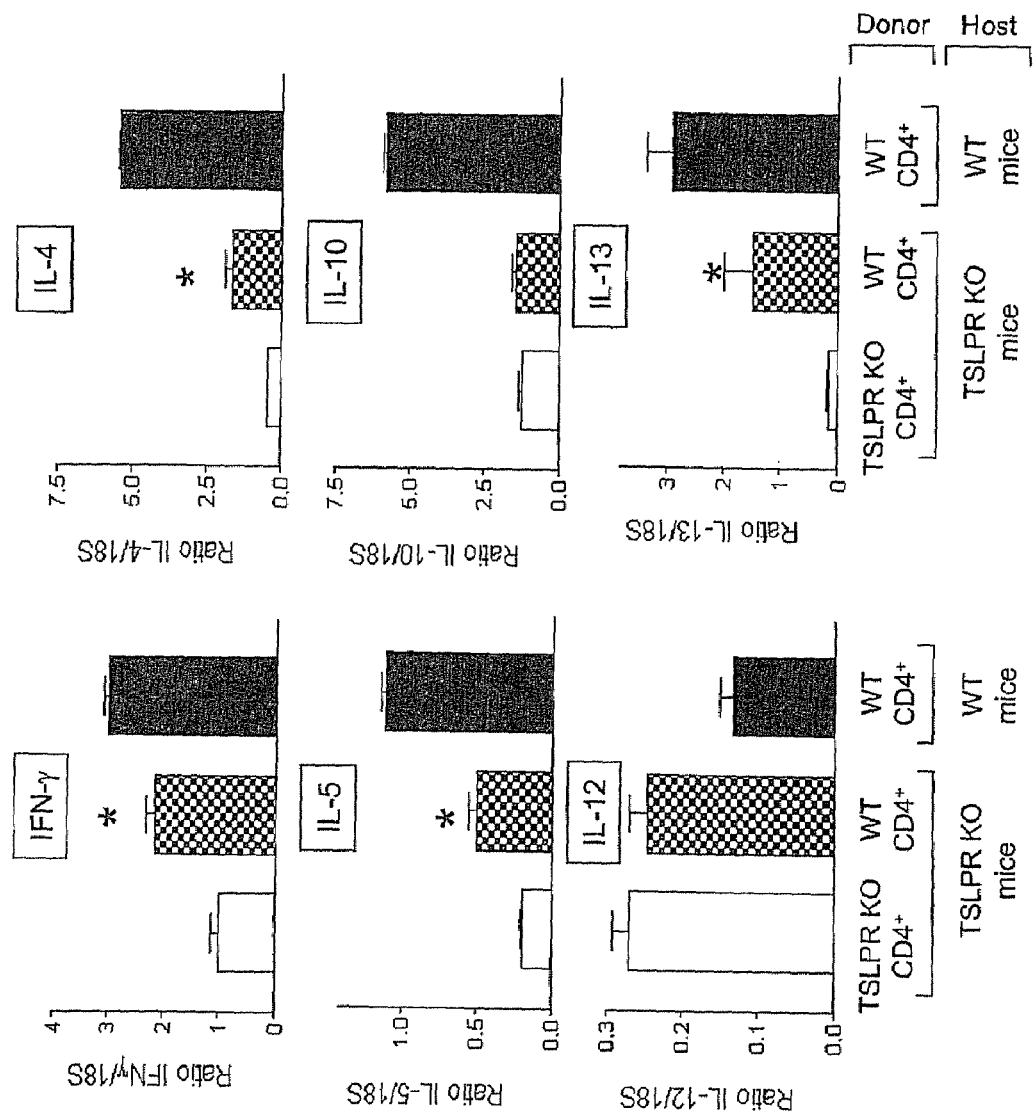
FIG. 16 is a set of bar graphs showing inflammatory cytokine levels in TSLPR KO mice supplemented with WT CD4$^+$ T cells. CD4$^+$ T cells were extracted from immunized donors and transferred to host mice 4 hours after OVA challenge (i.t). CD4$^+$ T cells from WT donors were transferred to WT (positive control) and TSLPR KO (test subject) mice while CD4$^+$ T cells from TSLPR KO mice were given to TSLPR KO mice to act as negative control. All mice were treated the next day with OVA (i.n.) and sacrificed 24 hours later. RNA was isolated from lung tissues and cytokine levels were determined by RTPCR. * indicates statistical significance $p<0.05$ between TSLPR KO mice that received WT CD4$^+$ T cells and those that did not.

The greatly diminished inflammatory response in the lungs of TSLPR KO mice may have resulted from the weak activation of $CD4^+$ T cells observed or could be due to a developmental defect in the TSLPR KO lungs. To help clarify the mechanism, WT mice were immunized twice with OVA and total $CD4^+$ T cells were extracted from spleen and LN and transferred (i.v.) into similarly immunized TSLPR KO mice. These mice were challenged by intratracheal (i.t.) and intranasal (i.n.) administration with OVA. Similarly, $CD4^+$ T cells from WT and TSLPR KO were transferred into WT and TSLPR KO animals to act as positive and negative controls, respectively. An examination of the lungs revealed severe inflammation and infiltration of eosinophils and neutrophils in WT animals receiving WT $CD4^+$ T cells (scoring 3.5 out of 4) (FIG. 15A), while TSLPR KO supplemented with TSLPR KO $CD4^+$ T cells showed little to no inflammation (0-0.5 out of 4) (FIG. 15B), consistent with the results above in Table 3 and FIG. 13. TSLPR KO mice that received WT $CD4^+$ T cells developed goblet cell hyperplasia and peribronchiole cuffing, mostly in the large airways but with some in the medium airways as well. They also showed infiltration of eosinophils and neutrophils scoring 2.2 out of 4 (range 1.5 to 2.75) on the inflammation scale. Thus, the TSLPR KO host can at least partially support an inflammatory response if WT $CD4^+$ T cells were provided. This was accompanied by a significant increase in the levels of IFN-γ, IL-4, IL-5, and IL-13 mRNA in the TSLPR KO mice that received WT $CD4^+$ T cells as compared to those that received TSLPR KO $CD4^+$ T cells (FIG. 16). These results further confirm the critical role that TSLP plays in the activation of $CD4^+$ T cells and is consistent with a role for this cytokine in the development of the inflammatory response.

The work presented herein demonstrates that TSLP preferentially enhances the proliferation and expansion of TCR-stimulated naïve phenotype $CD4^+$ T cells. Moreover, as shown with DO11.10 transgenic mice, TSLP is critical for the proper activation of $CD4^+$ T cells (e.g. expression of CD69) and their transition from naive/resting to activated effector cells.

Memory phenotype $CD4^+$ T cells express TSLPR mRNA but showed no significant proliferative response to TSLP. The decrease in the responsiveness of splenocytes from immunized TSLPR KO mice, as compared to WT animals, to secondary exposure to antigen may be attributed to the weak initiation phase of the immunization process, with fewer cells differentiating into effector and memory cells. It appears that naive cells are poised to respond to TSLP activation.

Murine DC can promote the clonal-specific expansion of naive $CD4^+$ T cells. Although murine DC express TSLPR, this effect of DC on $CD4^+$ T cells was only slightly reduced in the absence of TSLP signaling. In contrast, the action of TSLP on $CD4^+$ T cells was much more critical. Although TSLP had no direct effect on the levels of IFN-δ and IL-4 produced by $CD4^+$ T cells under neutral or polarizing conditions, indirectly however, TSLP-treated DC diminished the production of IFN-γ by $CD4^+$ T cells, and correspondingly, more IFN-δ and less IL-4 were produced by DO11.10/ TSLPR KO splenocytes than by DO11.10/WT cells. Thus, the greatest effect of TSLP on DC may be to augment the differentiation and cytokine production (rather than directly affecting the proliferation of naive $CD4^+$ T cells).

The critical role that TSLP plays in mounting an inflammatory response was revealed by the diminished response of TSLPR KO mice in an antigen-induced lung inflammation model. Specifically, TSLPR KO mice failed to develop an inflammatory response when challenged with OVA, and levels of cytokines known to be associated with an allergic immune response (IL-4, IL-5, and IL-10) were not increased. TSLP was slightly elevated in the lungs of WT animals sensitized with OVA, but this difference did not achieve statistical significance Interestingly, the lungs of TSLPR KO mice produced very little IL-13 at rest, although levels increased in response to OVA but only to levels normally observed in un-sensitized WT animals. Serum immunoglobulin levels in these animals indicate that a limited immune response is active in TSLPR KO mice since OVA-specific IgG1 and IgG2b were present; however, there was an increase in IgG2a and a decrease in IgE, corresponding to the more predominant Th1 phenotype in the absence of TSL. This could potentially result from higher levels of IFN-δ produced in the TSLPR KO $CD4^+$ T cells. Since IL-13 is a mediator of asthma that affects eosinophilic infiltration, mucus secretion, and airway hyper-responsiveness in the lungs (for example, see Wills-Karp et al., *Science* 282:2258-2261, 1998), the reduced IL-13 in the lungs of TSLPR KO mice might explain the absence of inflammation and IgE in these animals. Similarly, the absence of inflammatory $CD4^+$ T cells from the lungs could explain the lack of IL-5 and subsequently the absence of eosinophils in affected tissues.

The transfer of WT $CD4^+$ T cells to TSLPR KO mice had a profound effect on the ability of these mice to mount an inflammatory response. TSLPR KO lungs showed goblet cell hyperplasia and peribronchiole cuffing accompanied by the infiltration of inflammatory cells, consistent with the increase in IFN-γ, IL-4, IL-5 and IL-13. Thus, the lungs of TSLPR KO are structurally normal and the micro-environment within them can allow the development of an inflammatory response when functional preactivated $CD4^+$ T cells are available. However, the inflammation in TSLPR KO mice that received WT $CD4^+$ T cells did not reach as severe a level as is observed in WT animals. This might be explained by the fact that WT mice possess more $CD4^+$ T cells, as only a fraction of the WT $CD4^+$ T cells that were transferred to TSLPR KO animals are expected to be OVA responsive. In addition, the observed high levels of IL-12 in the lungs of TSLPR KO animals activated with OVA could further contribute to limiting the extent of the inflammatory response in these animals.

In conclusion, the studies disclosed herein reveal that TSLP plays a key role in promoting the proliferation of the naïve population of $CD4^+$ T cells. Although DC activation by TSLP may contribute to this process, the effect of TSLP on $CD4^+$ T cells appears to be the more important site of action. TSLP had little if any direct effect on cytokine production by $CD4^+$ T cells but can influence IFN-δ production via actions on DC. The role of TSLP in an in vivo allergic inflammatory model was investigated. Unexpectedly, profoundly reduced inflammation in the lungs of TSLPR KO mice was found. These data indicate that TSLP signaling is crucial for generation of an inflammatory reaction in the lung and establish TSLP as a potential target for modulating inflammation.

Example 14

Exemplary Embodiments

The experiments disclosed above document that TSLP modulates the activity of dendritic cells and naïve T cells. In addition, it is demonstrated herein that TSLP diminishes the generation a memory cells. Thus, methods are provided for altering the activity of dendritic cells, naïve T cells, and for diminishing the generation of memory cells, by administering TSLP, or an agonist thereof, to a subject. Alternatively, a nucleic acid encoding TSLP, or an agonist thereof, can be administered. Thus, a method is provided for enhancing and/or inducing an immune response in a subject, by administering a therapeutically effective amount of TSLP, or a nucleic acid encoding TSLP to the subject.

In one example, a method is provided for inducing proliferation of CD4+ T cells. The method includes contacting isolated CD4+ T cells with an effective amount of a TSLP polypeptide or a therapeutically effective amount of nucleic acid encoding the TSLP polypeptide, thereby inducing proliferation of the T cells. The T cells can be from any mammal, including, but not limited to a human. The method can include contacting isolated mammalian CD4+ T cells with an effective amount of the TSLP polypeptide, or a nucleic acid encoding the TSLP polypeptide. Several TSLP polypeptides of use are disclosed above. These TSLP polypeptides include an amino acid sequence set forth as one of SEQ ID NOs: 1-5, amino acids 29 to 159 of SEQ ID NO: 1, or amino acids 35 to 159 of SEQ ID NO: 1.

In another example, a method is provided for treating a subject with an immunodeficiency, such as an immunodeficiency that is the result of an infection with an immunodeficiency virus (for example, HIV) or that is the result of a genetic disorder (such as XSCID). The subject can also acquire the immunodeficiency as a result of an environmental exposure of the administration of an agent, such as radiation or chemotherapy. The method includes contacting isolated CD4+ T cells (either autologous or heterologous CD4+ cells) with a therapeutically effective amount of a TSLP polypeptide and administering the CD4+ T cells contacted with the TSLP polypeptide to the subject. The subject can be any mammalian subject, such as a human subject. Thus, in one example, a method is provided for treating a subject with an immunodeficiency, by administering to the subject a therapeutically effective amount of a TSLP polypeptide, or a therapeutically effective amount of nucleic acid encoding the TSLP polypeptide, thereby treating the subject.

In a further example, a method is provided for enhancing an immune response in a subject. The method includes (a) contacting the population of isolated CD4+ cells (either autologous or heterologous) with a composition comprising TSLP ex vivo, thereby expanding CD4+ T cells; and (b) introducing the CD4+ T cells into the subject. The method can include contacting the population of cells with at least one composition comprising an antigen, but does not necessarily include this step. The antigen can be a viral antigen, a bacterial antigen, or an antigen from a parasite. It should be noted that the subject can be any subject, including but not limited to a human subject. For example, the subject can be infected with an immunodeficiency virus, such as HIV-1 or HIV2, or can have an immunodeficiency that is a result of a genetic disorder, such as SCID. The subject can also have acquired an immunodeficiency as a result of an environmental exposure or administration of an agent, such as radiation or a chemotherapeutic agent.

In yet another example, a method is provided for treating a subject with an inflammatory disorder, such as IgE-mediated disorder. The method includes administering to the subject a therapeutically effective amount of a thymic stromal derived lymphopoietin (TSLP) antagonist. In one example, the IgE-mediated disorder is asthma. In other examples, the disorder is allergic rhinitis, allergic dermatitis, or allergic conjunctivitis. The TSLP antagonist can be an antibody that binds TSLP or the TSLP receptor, such as a humanized antibody, and can be administered by any means, such as by inhalation, intranasal, and/or intratrachael administration. In addition to the TSLP antagonist the subject can be treated with therapeutically effective amount of an anti-infective agent, an anti-inflammatory agent, a bronchodilator, an enzyme, an expectorant, a leukotriene antagonist, a leukotriene formation inhibitor, or a mast cell stabilizer.

Example 15

Rhino-Conjunctivitis Model System

Adult mice (6-8 weeks in age, of either sex) are sensitized by intraperitoneal injection of 50 micrograms of ragweed mixed 1:1 with aluminum hydroxide on days 0 and 7. Mice are challenged by eye drops and intranasally with ragweed in PBS 5 microliters (1 mg) in the eye and 30 microliters (50 µg) in the nose on days 14 and 15. Animals are sacrificed on day 17.

One group of animals are treated with a TSLP antagonist 24 hours prior to antigen challenge (day 13). For example, mice are treated 24 hours prior to challenge with an antibody that binds TSLP. An exemplary amount is 1 mg i.p. Control animals are treated with isotype control antibody, and a group is treated with PBS.

Mice are then assessed for an inflammatory response. For example, eyes with lids attached are isolated from the animals. The nasal passages are also removed. Histology is performed, such as periodic Schiff's staining (PAS) to identify goblet cells. Hemotoxylin and eosin and Wright's Giemsa stain are can also be used. Mast cell degranulation, eosinophil infiltration and goblet cell hyperplasia are assessed. Mice administered the TLSP antagonist show reduced mast cell degranulation and/or reduced eosinophil infiltration and/or reduced goblet cell hyperplasia.

It will be apparent that the precise details of the methods or compositions described may be varied or modified without departing from the spirit of the described invention. We claim all such modifications and variations that fall within the scope and spirit of the claims below.

The invention claimed is:

1. A method for inducing proliferation of human naïve CD4+ T cells, comprising
   (a) isolating a population of cells comprising human naïve CD4+ T cells and
   (b) contacting the population with (i) an antigen selected from the group consisting of a viral antigen, a bacterial antigen, or an antigen from a parasite, and (iii) an effective amount of a human thymic stromal derived lymphopoietin (TSLP) polypeptide,
   thereby inducing proliferation of the T cells.

2. The method of claim 1, wherein the TSLP polypeptide comprises the amino acid sequence selected from the group consisting of SEQ ID NO: 1, SEQ ID NO: 4, SEQ ID NO: 5, amino acids 29 to 159 of SEQ ID NO: 1, and amino acids 35 to 159 of SEQ ID NO: 1.

3. A method of inducing or enhancing an immune response in a human subject, comprising
   (a) contacting isolated human naïve CD4+ T cells with (i) a therapeutically effective amount of a human thymic stromal derived lymphopoietin (TSLP) polypeptide, and (ii) an antigen, thereby expanding the CD4+ T cells; and
   (b) administering the CD4+ T cells contacted with the TSLP polypeptide and the antigen to the subject,
   thereby inducing or enhancing an immune response in the subject.

4. The method of claim 3, wherein the TSLP polypeptide comprises the amino acid sequence selected from the group consisting of SEQ ID NO: 1, SEQ ID NO: 4, SEQ ID NO: 5, amino acids 29 to 159 of SEQ ID NO: 1, and amino acids 35 to 159 of SEQ ID NO: 1.

5. The method of claim 3, wherein the subject has an immunodeficiency.

6. The method of claim 5, wherein the immunodeficiency is the result of an infection with an immunodeficiency virus.

7. The method of claim 6, wherein the immunodeficiency virus is a human immunodeficiency virus (HIV).

8. The method of claim 5, wherein the subject has an immunodeficiency as a result of a genetic disorder.

9. The method of claim 5, wherein the immunodeficiency is a result of treatment with radiation, a chemotherapeutic agent, or a combination thereof.

* * * * *

SEQUENCE LISTING

<160> NUMBER OF SEQ ID NOS: 11

<210> SEQ ID NO 1
<211> LENGTH: 159
<212> TYPE: PRT
<213> ORGANISM: Homo sapiens

<400> SEQUENCE: 1

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 2
<211> LENGTH: 140
<212> TYPE: PRT
<213> ORGANISM: Mus musculus

<400> SEQUENCE: 2

Met Val Leu Leu Arg Ser Leu Phe Ile Leu Gln Val Leu Val Arg Met
1               5                   10                  15

Gly Leu Thr Tyr Asn Phe Ser Asn Cys Asn Phe Thr Ser Ile Thr Lys
            20                  25                  30

Ile Tyr Cys Asn Ile Ile Phe His Asp Leu Thr Gly Asp Leu Lys Gly
        35                  40                  45

Ala Lys Phe Glu Gln Ile Glu Asp Cys Glu Ser Lys Pro Ala Cys Leu
    50                  55                  60

Leu Lys Ile Glu Tyr Tyr Thr Leu Asn Pro Ile Pro Gly Cys Pro Ser
65                  70                  75                  80

Leu Pro Asp Lys Thr Phe Ala Arg Arg Thr Arg Glu Ala Leu Asn Asp
                85                  90                  95

His Cys Pro Gly Tyr Pro Glu Thr Glu Arg Asn Asp Gly Thr Gln Glu
            100                 105                 110

Met Ala Gln Glu Val Gln Asn Ile Cys Leu Asn Gln Thr Ser Gln Ile
        115                 120                 125

Leu Arg Leu Trp Tyr Ser Phe Met Gln Ser Pro Glu
130                 135                 140

<210> SEQ ID NO 3
<211> LENGTH: 360
<212> TYPE: PRT
<213> ORGANISM: Rattus norvegicus

<400> SEQUENCE: 3

Met Arg Ala Val Thr Trp Ala Ile Val Ala Met Leu Leu Pro Arg Val
1               5                   10                  15

Leu Gly Ala Ile Pro Thr Arg Thr Pro Arg Thr Gly Gly Val Gly Asp

```
                    20                  25                  30
Thr Leu Ser Val Ala Ile Val Cys His Asp Leu Glu Ser Val Glu Val
            35                  40                  45

Thr Trp Gly Pro Gly Ser Ala His His Gly Leu Ser Ala Asn Leu Ser
        50                  55                  60

Leu Glu Phe Arg Tyr Gly Asn Gln Val Pro Gln Pro Cys Pro His Tyr
65                  70                  75                  80

Phe Leu Leu Asp Ser Val Arg Ala Gly Cys Val Leu Pro Met Gly Lys
                85                  90                  95

Gly Leu Leu Glu Val Val Leu Arg Glu Gly Gly Ala Lys Leu Phe
            100                 105                 110

Ser Arg Lys Lys Lys Ala Ser Ala Trp Leu Arg Pro Arg Pro Pro Trp
        115                 120                 125

Asn Val Thr Leu Ser Trp Val Gly Asp Thr Val Ala Val Ser Cys Pro
        130                 135                 140

Ser His Ser Tyr Pro Gly Leu Glu Tyr Glu Val Gln His Arg Asp Asp
145                 150                 155                 160

Phe Asp Pro Glu Trp Gln Ser Thr Ser Ala Pro Phe Cys Asn Leu Thr
                165                 170                 175

Val Gly Gly Leu Asp Pro Gly Arg Cys Tyr Asp Phe Arg Val Arg Ala
            180                 185                 190

Thr Pro Gln Asp Phe Tyr Tyr Gly Pro Glu Ala Arg Pro Ser Lys Trp
        195                 200                 205

Thr Gly Val Ala Ser Leu Gln Gly Val Gly Pro Thr Gly Ser Cys Thr
        210                 215                 220

Gly Pro Thr Leu Pro Arg Thr Pro Gly Thr Pro Thr Pro Pro Leu Ala
225                 230                 235                 240

Leu Ala Cys Gly Leu Ala Val Ala Leu Leu Thr Leu Val Leu Leu Leu
                245                 250                 255

Ala Leu Leu Arg Met Arg Arg Val Lys Glu Ala Leu Leu Pro Gly Val
            260                 265                 270

Pro Asp Pro Arg Gly Ser Phe Pro Gly Leu Phe Glu Lys His His Gly
        275                 280                 285

Asn Phe Gln Ala Trp Ile Ala Asp Ser Gln Ala Ala Val Pro Thr Val
        290                 295                 300

Pro Glu Gln Asp Lys Asp Asp Val Ile Arg Pro Gln Thr Lys Gly
305                 310                 315                 320

Val Glu Thr Gln Glu Asp Asp Val Ile Ala Pro Gly Ser Pro Cys
                325                 330                 335

Leu Gly Gly Gly Ala Leu Met Ser Val Gly Gly Ala Ser Phe Leu Met
            340                 345                 350

Gly Asp Ser Gly Tyr Thr Thr Leu
        355                 360

<210> SEQ ID NO 4
<211> LENGTH: 60
<212> TYPE: PRT
<213> ORGANISM: Homo sapiens

<400> SEQUENCE: 4

Met Lys Thr Lys Ala Ala Leu Ala Ile Trp Cys Pro Gly Tyr Ser Glu
1               5                   10                  15

Thr Gln Ile Asn Ala Thr Gln Ala Met Lys Lys Arg Arg Lys Arg Lys
            20                  25                  30
```

```
Val Thr Thr Asn Lys Cys Leu Glu Gln Val Ser Gln Leu Gln Gly Leu
        35                  40                  45

Trp Arg Arg Phe Asn Arg Pro Leu Leu Lys Gln Gln
 50                  55                  60

<210> SEQ ID NO 5
<211> LENGTH: 159
<212> TYPE: PRT
<213> ORGANISM: Homo sapiens

<400> SEQUENCE: 5

Met Lys Cys Leu Gly Gln Ser Lys Lys Glu Val Ser Phe Arg Lys
 1               5                  10                  15

Ile Phe Ile Leu Gln Leu Val Gly Leu Val Leu Thr Tyr Asp Phe Thr
                20                  25                  30

Asn Cys Asp Phe Glu Lys Ile Lys Ala Ala Tyr Leu Ser Thr Ile Ser
            35                  40                  45

Lys Asp Leu Ile Thr Tyr Met Ser Gly Thr Lys Ser Thr Glu Phe Asn
 50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
                100                 105                 110

Tyr Ser Glu Thr Gln Ile Asn Ala Thr Gln Ala Met Lys Lys Arg Arg
            115                 120                 125

Lys Arg Lys Val Thr Thr Asn Lys Cys Leu Glu Gln Val Ser Gln Leu
        130                 135                 140

Gln Gly Leu Trp Arg Arg Phe Asn Arg Pro Leu Leu Lys Gln Gln
145                 150                 155

<210> SEQ ID NO 6
<211> LENGTH: 27
<212> TYPE: DNA
<213> ORGANISM: Artificial
<220> FEATURE:
<223> OTHER INFORMATION: oligonucleotide primer

<400> SEQUENCE: 6
aacctctccc acaagaagtc cagaagt                                          27

<210> SEQ ID NO 7
<211> LENGTH: 21
<212> TYPE: DNA
<213> ORGANISM: Artificial
<220> FEATURE:
<223> OTHER INFORMATION: oligonucleotide primer

<400> SEQUENCE: 7
atcgccttct atcgccttct t                                                21

<210> SEQ ID NO 8
<211> LENGTH: 24
<212> TYPE: DNA
<213> ORGANISM: Artificial
<220> FEATURE:
<223> OTHER INFORMATION: oligonucleotide primer

<400> SEQUENCE: 8
agactttacc tgattcctgc cttg                                             24
```

```
<210> SEQ ID NO 9
<211> LENGTH: 21
<212> TYPE: DNA
<213> ORGANISM: Artificial
<220> FEATURE:
<223> OTHER INFORMATION: oligonucleotide primer

<400> SEQUENCE: 9
gcgagggcgg ggctgctgga g                                              21

<210> SEQ ID NO 10
<211> LENGTH: 21
<212> TYPE: DNA
<213> ORGANISM: Artificial
<220> FEATURE:
<223> OTHER INFORMATION: oligonucleotide primer

<400> SEQUENCE: 10
cctggctggc ggggctgtgg c                                              21

<210> SEQ ID NO 11
<211> LENGTH: 743
<212> TYPE: DNA
<213> ORGANISM: Homo sapiens

<400> SEQUENCE: 11
gcagccagaa agctctggag catcagggag actccaactt aaggcaacag catgggtgaa    60
taagggcttc ctgtggactg gcaatgagag gcaaaacctg gtgcttgagc actggcccct   120
aaggcaggcc ttacagatct cttacactcg tggtgggaag agtttagtgt gaaactgggg   180
tggaattggg tgtccacgta tgttcccttt tgccttacta tatgttctgt cagtttcttt   240
caggaaaatc ttcatcttac aacttgtagg gctggtgtta acttacgact tcactaactg   300
tgactttgag aagattaaag cagcctatct cagtactatt tctaaagacc tgattacata   360
tatgagtggg accaaaagta ccgagttcaa caacaccgtc tcttgtagca atcggccaca   420
ttgccttact gaaatccaga gcctaacctt caatcccacc gccggctgcg cgtcgctcgc   480
caaagaaatg ttcgccatga aaactaaggc tgccttagct atctggtgcc caggctattc   540
ggaaactcag ataaatgcta ctcaggcaat gaagaagagg agaaaaagga aagtcacaac   600
caataaatgt ctggaacaag tgtcacaatt acaaggattg tggcgtcgct tcaatcgacc   660
tttactgaaa caacagtaaa ccatctttat tatggtcata tttcacagcc caaaataaat   720
catctttatt aagtaaaaaa aaa                                           743
```